US008986750B2

(12) United States Patent (10) Patent No.: US 8,986,750 B2
Zhong et al. (45) Date of Patent: Mar. 24, 2015

(54) USE OF A TRADITIONAL CHINESE MEDICINE COMPOSITION FOR MANUFACTURING A HEALTH FOOD OR MEDICAMENT FOR PREVENTING AND ALLEVIATING PHYSICAL FATIGUE

(75) Inventors: Hongguang Zhong, Nanchang (CN); Minzhi Yi, Nanchang (CN); Jianzhong Lu, Nanchang (CN); Yiguang Li, Nanchang (CN); Li Ma, Nanchang (CN); Yongjin Guo, Nanchang (CN); Jinzhen Xu, Nanchang (CN); Yibin Lv, Nanchang (CN); Meixiang Yao, Nanchang (CN)

(73) Assignee: Jiangzhong Pharmaceutical Co., Ltd., Nanchang, Jiangxi Province (CN)

( * ) Notice: Subject to any disclaimer, the term of this patent is extended or adjusted under 35 U.S.C. 154(b) by 78 days.

(21) Appl. No.: 13/824,375

(22) PCT Filed: Sep. 16, 2011

(86) PCT No.: PCT/CN2011/079731
§ 371 (c)(1),
(2), (4) Date: May 29, 2013

(87) PCT Pub. No.: WO2012/034534
PCT Pub. Date: Mar. 22, 2012

(65) Prior Publication Data
US 2013/0243748 A1 Sep. 19, 2013

(30) Foreign Application Priority Data

Sep. 17, 2010 (CN) .......................... 2010 1 0285082
Sep. 17, 2010 (CN) .......................... 2011 1 0208867
Sep. 17, 2010 (CN) .......................... 2011 1 0208869
Sep. 17, 2010 (CN) .......................... 2011 1 0208871
Sep. 17, 2010 (CN) .......................... 2011 1 0208872
Jul. 25, 2011 (CN) .......................... 2011 1 0208873

(51) Int. Cl.
*A61K 36/00* (2006.01)
*A61K 36/074* (2006.01)
*A61K 36/738* (2006.01)
*A61K 36/068* (2006.01)
*A61K 36/258* (2006.01)
*A61K 36/344* (2006.01)
*A61K 36/36* (2006.01)
*A61K 36/43* (2006.01)
*A61K 36/481* (2006.01)

(52) U.S. Cl.
CPC ............. *A61K 36/258* (2013.01); *A61K 36/068* (2013.01); *A61K 36/074* (2013.01); *A61K 36/344* (2013.01); *A61K 36/36* (2013.01); *A61K 36/43* (2013.01); *A61K 36/481* (2013.01); *A61K 36/738* (2013.01)
USPC .......................................... 424/725; 424/728

(58) Field of Classification Search
None
See application file for complete search history.

(56) References Cited

U.S. PATENT DOCUMENTS 7,608,286 B2 * 10/2009 Olalde Rangel .............. 424/725

FOREIGN PATENT DOCUMENTS

| CN | 1381266 A | * 11/2002 |
|---|---|---|
| CN | 1520879 A | 8/2004 |
| CN | 1772005 A | * 5/2006 |
| CN | 101181529 A | * 5/2008 |
| CN | 101292742 A | 10/2008 |
| CN | 101612181 A | 12/2009 |
| CN | 102108329 A | 2/2011 |
| CN | 101999663 A | 4/2011 |
| JP | 63-133969 | 6/1988 |
| JP | 05-123135 | 5/1993 |
| JP | 05-124974 | 5/1993 |
| JP | 05-139982 | 6/1993 |
| JP | 10-117770 | 5/1998 |
| JP | 2001-302535 | 10/2001 |
| JP | 2002-145792 | 5/2002 |
| JP | 2002-173441 | 6/2002 |
| JP | 2002-275086 | 9/2002 |
| JP | 2003-292452 | 10/2003 |
| JP | 2005-000095 | 1/2005 |
| JP | 2005-089397 | 4/2005 |
| JP | 2009-298701 | 12/2009 |
| WO | 2009/133998 A | 11/2009 |

OTHER PUBLICATIONS

Outlook Weekly, "Producing a restorative better than Cordyceps," Issue No. 37, Sep. 13, 2010.
Liu Zhi Gang, et al., "Laboratory studies on the blood lipid-reducing function of the composite powder for oral liquid Shenlingcao," Chinese Journal of Ethnomedicine and Ethnopharmacy, vol. 8, pp. 1-2 (2009).
Office Action dated Oct. 7, 2014, Japanese Patent Application No. 2013-528508 (including translation).

* cited by examiner

*Primary Examiner* — Qiuwen Mi
(74) *Attorney, Agent, or Firm* — Michael Fedrick; Loza & Loza, LLP

(57) ABSTRACT

The present invention provides a use of traditional Chinese medicine composition for manufacturing a health food or medicament for preventing and alleviating physical fatigue. The composition consists of 5-90 parts by weight of Radix Panacis Quinquefolii, 5-160 parts by weight of *Ganoderma*, 1-90 parts by weight of fermented *Cordyceps sinensis* powder and/or 1-120 parts by weight of *Cordyceps*, and these ingredients are made from Chinese crude drugs or from Chinese crude drug extracts in amounts equivalent to those of the Chinese crude drugs. The composition may further contain 5-90 parts by weight of Flos Rosae Rugosae. The present invention also relates to the use of said composition in the manufacture of prophylactic or therapeutic health foods or medicaments for reducing blood lipids, for resisting oxidation, and for enhancing anoxia endurance. The medicine composition of the present invention can be prepared into any conventional dosage forms by adding any pharmaceutically acceptable auxiliary agents.

7 Claims, No Drawings

USE OF A TRADITIONAL CHINESE MEDICINE COMPOSITION FOR MANUFACTURING A HEALTH FOOD OR MEDICAMENT FOR PREVENTING AND ALLEVIATING PHYSICAL FATIGUE

CROSS-REFERENCE TO RELATED APPLICATIONS

This application is the U.S. national stage of International Patent Application No. PCT/CN2011/079731, filed on Sep. 16, 2011, which claims the benefit of priority under 35 U.S.C. §119 from the following Chinese patent applications: Chinese Patent Application No. 201110208871.9, filed on Sep. 17, 2010; Chinese Patent Application No. 201110208867.2, filed on Sep. 17, 2010; Chinese Patent Application No. 201110208869.1, filed on Sep. 17, 2010; Chinese Patent Application No. 201110208872.3, filed on Sep. 17, 2010; Chinese Patent Application No. 201010285082.0, filed on Sep. 17, 2010; and Chinese Patent Application No. 201110208873.8, filed on Jul. 25, 2011. The disclosures of the foregoing applications are incorporated herein by reference in their entirety.

TECHNICAL FIELD

The present invention relates to a traditional Chinese medicine (TCM) composition as a health food or medicament for alleviating physical fatigue, and use thereof in the field of health foods or medicaments.

BACKGROUND ART

Among the health foods capable of resisting oxidation, resisting fatigue, reducing blood lipids, and enhancing anoxia endurance that have been disclosed in the Chinese patent documents, some products comprise such ingredients as Radix Panacis Quinquefolii, *Ganoderma* or extract thereof, *Cordyceps* or extract thereof, or fermented *Cordyceps sinensis* powder. For example, Chinese Patent Application No. 02115148.2 discloses a health tea having *Ganoderma* and Radix Et Rhizoma Herba Rhodiolae as major ingredients and capable of enduring anoxia, resisting fatigue, resisting aging, improving sleep, and benefiting "Qi" and body; Chinese Patent Application No. 96100057.0 discloses a health preserving tea made from *Ganoderma* and Fructus Crataegi as major materials and capable of enhancing immunity, reducing blood lipids, and regulating blood pressure; and Chinese Patent Application No. 99117565.4 discloses a health tea made from *Cordyceps, Ganoderma*, Radix Et Rhizoma Ginseng, and Fructus Lycii as major materials and producing the effects of resisting fatigue, resisting aging, reducing blood lipids and blood sugar, and promoting blood circulation. Until now there has not been such a health food or medicament that is prepared according to a formulation comprising three materials, i.e., (i) Radix Panacis Quinquefolii, (ii) *Ganoderma*, and (iii) fermented *Cordyceps sinensis* powder or *Cordyceps*, or according to a formulation comprising four materials composed of the above three materials and (iv) Flos Rosae Rugosae, used for resisting oxidation, resisting fatigue, reducing blood lipids, and enhancing anoxia endurance.

SUMMARY OF THE INVENTION

The objective of the present invention is to provide a traditional Chinese medicine composition (TCM composition) as a health food or medicament which is remarkably effective in alleviating physical fatigue. Another objective of the present invention is to provide a novel use of the traditional Chinese medicine-containing composition in the field of health foods or medicaments.

The present invention selects and combines Radix Panacis Quinquefolii/Radix Et Rhizoma Ginseng, *Ganoderma*, and fermented *Cordyceps sinensis* powder to allow these drugs to exert a synergistic effect, so as to more effectively perform their function of alleviating physical fatigue. According to the channel tropism of the three drugs Radix Panacis Quinquefolii/Radix Et Rhizoma Ginseng, *Cordyceps*, and *Ganoderma*, it can be seen that the heart, liver, spleen, lung, and kidney channels are all involved so as to achieve overall regulation of the Five Zang Viscera. Radix Panacis Quinquefolii has a pungent, sweet, and slightly bitter taste and a warm nature, the most significant effects of which are to activate Qi flowing, resolve stagnation, harmonize the blood, and relieve pain. Radix Et Rhizoma Ginseng has a sweet and slightly bitter taste and a slightly warm nature. *Ganoderma* nourishes physical strength, strengthens and consolidates body resistance. *Cordyceps* has a sweet taste and a plain nature, and is involved in the lung and kidney channels to benefit the kidney and invigorate the lung, whereby assisting *Ganoderma* to strengthen and consolidate body resistance together with Radix Panacis Quinquefolii or Radix Et Rhizoma Ginseng.

In order to achieve better efficacy, Flos Rosae Rugosae may be added to the medicine of the present invention in addition to the above drugs to exert a synergistic effect, as Flos Rosae Rugosae has a color that helps harmonize the blood, a fragrance that helps activate Qi flowing, and effects of dispersing stagnated liver Qi, resolving stagnation, and promoting blood circulation, and thus leads to harmonization, promotion, and balance. When Flos Rosae Rugosae is used as an adjuvant, a combination of the four drugs is provided and results in overall regulation of the Five Zang Viscera, mutual complement between warm and cool natures, benefiting of both Qi and blood, supplementation without causing dryness, nourishment without causing greasy feelings, plain supplementation coupled with moderate regulation, mild impacts, a stronger effect of relieving physical fatigue, and eventually better efficacy. In order to achieve even better efficacy, *Cordyceps* may be further added in the composition to produce the strongest effect of relieving physical fatigue and the best efficacy.

According to the present invention, various combinations of the above drugs having the amounts of various components which fall within the following ranges based on parts by weight will have an excellent effect of relieving physical fatigue.

The composition of the present invention comprises the materials of 5-150 parts of Radix Panacis Quinquefolii and/or Radix Et Rhizoma Ginseng, 5-160 parts of *Ganoderma*, and 1-120 parts of *Cordyceps* and/or 1-90 parts of fermented *Cordyceps sinensis* powder, or water/alcohol extracts of these materials, as the active ingredients, and pharmaceutically acceptable additives;

wherein, the materials are preferably 10-90 parts of Radix Panacis Quinquefolii and/or Radix Et Rhizoma Ginseng, 20-90 parts of *Ganoderma*, and 3-90 parts of *Cordyceps* and/or 3-60 parts of fermented *Cordyceps sinensis* powder; more preferably 10-50 parts of Radix Panacis Quinquefolii and/or Radix Et Rhizoma Ginseng, 10-50 parts of *Ganoderma*, and 10-70 parts of *Cordyceps* and/or 10-50 parts of fermented *Cordyceps sinensis* powder; and most preferably 30 parts of Radix Panacis Quinquefolii and/or Radix Et Rhizoma Ginseng, 40 parts of *Ganoderma*, and 6.7 parts of *Cordyceps* and/or 20 parts of fermented *Cordyceps sinensis* powder.

Furthermore, the medicament of the present invention may comprises the materials of 5-150 parts of Radix Panacis Quinquefolii and/or Radix Et Rhizoma Ginseng, 5-160 parts of *Ganoderma*, 1-120 parts of *Cordyceps* and/or 1-90 parts of fermented *Cordyceps sinensis* powder and 5-90 parts of Flos Rosae Rugosae, or water/alcohol extracts of these materials, as the active ingredients, and pharmaceutically acceptable additives;

wherein, the materials are preferably 10-90 parts of Radix Panacis Quinquefolii and/or Radix Et Rhizoma Ginseng, 20-90 parts of *Ganoderma*, 3-90 parts of *Cordyceps* and/or 3-60 parts of fermented *Cordyceps sinensis* powder, and 10-60 parts of Flos Rosae Rugosae; more preferably 10-50 parts of Radix Panacis Quinquefolii and/or Radix Et Rhizoma Ginseng, 10-50 parts of *Ganoderma*, 10-70 parts of *Cordyceps* and/or 10-50 parts of fermented *Cordyceps sinensis* powder, and 10-40 parts of Flos Rosae Rugosae; and most preferably 30 parts of Radix Panacis Quinquefolii and/or Radix Et Rhizoma Ginseng, 40 parts of *Ganoderma*, 6.7 parts of *Cordyceps* and/or 20 parts of fermented *Cordyceps sinensis* powder, and 30 parts of Flos Rosae Rugosae.

The composition of the present invention may further comprises additional materials that do not compromise the efficacy of the present invention or water/alcohol extracts of these additional materials as the active ingredients, and pharmaceutically acceptable additives; wherein the additional material may be, for example, one of 3-300 parts of Radix Pseudostellariae, 10-120 parts of Folium Ginseng, 3-160 parts of Radix Codonopsis, 3-200 parts of Radix Astragali, and 5-150 parts of Semen Cuscutae, or any combination thereof.

The present invention further relates to use of the above composition in the manufacture of a prophylactic or therapeutic health food or medicament for alleviating physical fatigue.

The present invention further relates to use of the above composition in the manufacture of a prophylactic or therapeutic health food or medicament for reducing blood lipids.

The present invention further relates to use of the above composition in the manufacture of a prophylactic or therapeutic health food or medicament for resisting oxidation.

The present invention further relates to use of the above composition in the manufacture of a health food or medicament for enhancing anoxia endurance.

The present invention relates to use of a medicine composition composed of 10-50 parts by weight of Radix Panacis Quinquefolii, 10-50 parts by weight of *Ganoderma*, and 10-50 parts by weight of fermented *Cordyceps sinensis* powder, in the manufacture of a prophylactic or therapeutic health food or medicament for alleviating physical fatigue.

The present invention further relates to use of a medicine composition composed of 10-50 parts by weight of Radix Panacis Quinquefolii, 10-50 parts by weight of *Ganoderma*, and 10-50 parts by weight of fermented *Cordyceps sinensis* powder, in the manufacture of a prophylactic or therapeutic health food or medicament for reducing blood lipids.

The present invention further relates to use of a medicine composition composed of 10-50 parts by weight of Radix Panacis Quinquefolii, 10-50 parts by weight of *Ganoderma*, and 10-50 parts by weight of fermented *Cordyceps sinensis* powder, in the manufacture of a prophylactic or therapeutic health food or medicament for resisting oxidation.

The present invention further relates to use of a medicine composition composed of 10-50 parts by weight of Radix Panacis Quinquefolii, 10-50 parts by weight of *Ganoderma*, 10-50 parts by weight of fermented *Cordyceps sinensis* powder, and 10-40 parts by weight of Flos Rosae Rugosae, in the manufacture of a prophylactic or therapeutic health food or medicament for alleviating physical fatigue.

The present invention further relates to use of a medicine composition composed of (i) 10-50 parts by weight of Radix Panacis Quinquefolii, (ii) 10-50 parts by weight of *Ganoderma*, (iii) 10-50 parts by weight of fermented *Cordyceps sinensis* powder, and (iv) 10-40 parts by weight of Flos Rosae Rugosae, in the manufacture of a prophylactic or therapeutic health food or medicament for reducing blood lipids.

The present invention further relates to use of a medicine composition composed of 10-50 parts by weight of Radix Panacis Quinquefolii, 10-50 parts by weight of *Ganoderma*, 10-50 parts by weight of fermented *Cordyceps sinensis* powder, and 10-40 parts by weight of Flos Rosae Rugosae, in the manufacture of a prophylactic or therapeutic health food or medicament for resisting oxidation.

The term "*Ganoderma*", as used herein, refers to the dry sporocarp of plant species *Ganoderma lucidum* (Leyss. ex Fr.) or *Ganoderma sinense* Zhao, Xu et Zhang of the genus *Ganoderma*, family Polyporaceae, phylum Basidiomycota. It has a sweet taste and a plain nature, is involved in the heart, lung, liver and kidney channels, and has the effects of nourishing physical strength and calming and tranquillizing the mind. The term "Radix Et Rhizoma Ginseng", as used herein, refers to the dry root and rootstock of the plant species *Panax ginseng* C. A. Mey. of the family Araliaceae. It may be various types of ginseng, such as garden ginseng, wild ginseng, dried fresh ginseng, dried fresh wild ginseng, sugar-processed ginseng, and red ginseng. In addition, Folium Ginseng (the dry leaves of the plant species *Panax ginseng* C. A. Mey. of the family Araliaceae) may be selected to substitute for Radix Panacis Quinquefolii or Radix Et Rhizoma Ginseng. The term "Radix Panacis Quinquefolii", as used herein, also known as American ginseng, huaqishen, yangshen, or guangdongshen, refers to the dry root of the plant species *Panax quinquefolium* L. of the family Araliaceae. It has a sweet and slightly bitter taste and a cool nature, is involved in the heart, lung and kidney channels, and has the effects of invigorating Qi, nourishing Yin, clearing heat, and promoting fluid production. The term "*Cordyceps*", as used herein, refers to a dry complex from a dead body of an insect larva of the family Hepialidae and a stroma of the fungal species *Cordyceps sinensis* (Berk.) sace. of the family Clavicipitaceae parasitizing on the larva.

The term "fermented *Cordyceps sinensis* powder", as used herein, refers to a product of strains that were originally isolated from the natural *Cordyceps* of *Cordyceps sinensis* (Berk.) sace and have been cultured under fermentation conditions, wherein the strains may be, for example, *Paecilongces hepialli* Chen et Dai, sp. nov, *Hirsutella sinensis* Liu, Guo, Yu et Zeng, sp. nov, *Cephalosporium sinensis* Chen sp. nov, *Mortiserella hepialid* C. T.&B. liu, *Paecilomyces sinensis* Chen, Xiao et Shi, sp. nov, *Tolypocladium sinensis* C. lan Li, *Cephalosporium sinens* Chen sp. nov, *Scytalidium hepialii* C. L. Li, *Chrysosporium sinens* Z. Q. liang, *Verticillium sinens* Wamg sp. nov, *Cephalosporium acremonium* Corda, *Icones Fungorum, Synnematium sinensis* Yin & Shen, *Isaria farinose* (Holmsk.) Fr. Systema Mycologicum, *Metarhizium anisopliae* (Metsch) Sorokin, *Hirsutella hepialid* Chen et Shen, *Sporothrix insectorum* de Hong & H. C. Evans, *Gliocladium roseum* (link) Thom, or *Mortierella* sp.

The term "Flos Rosae Rugosae", as used herein, refers to the dry flower bud of the plant species *Rosa rugosa* Thumb of the family Rosaceae. It has a pungent, sweet and slightly bitter taste and a warm nature, and represents a warm-natured drug. Its most significant effects are to activate Qi flowing, resolve stagnation, harmonize the blood, and relieve pain.

The term "Radix Codonopsis" refers to the dry root of the plant species *Codonopsis pilosula* (Franch.) Nannf., *Codonopsis pilosula* Nannf. var. modesta (Nannf.) L. T. Shen, or *Codonopsis tangshen* Oliv. of the family Campanulaceae.

The term "Semen Cuscutae" refers to the dry, mature seeds of the plant species *Cuscuta australis* or *Cuscuta chinensis* Lam. of the family Convolvulaceae. The term "Radix Astragali", as used herein, refers to the dry root of the plant species *Astragalus membranaceus* (Fisch) Bge. var. mongholicus (Bge) Hsiao or *Astragalus membranaceus* (Fisch) Bge. of the family Fabaceae.

The preparation process of the traditional Chinese medicine composition according to the present invention includes the steps of:

1) weighing the following Chinese crude drugs as raw materials: 5-150 parts of Radix Panacis Quinquefolii and/or Radix Et Rhizoma Ginseng, 5-160 parts of *Ganoderma*, 1-120 parts of *Cordyceps* and/or 1-90 parts of fermented *Cordyceps sinensis* powder, or 5-90 parts of Flos Rosae Rugosae;

2) extracting the above crude drugs with alcohol or water under reflux to obtain a liquid extract as active ingredients, and adding additives to produce various dosage forms.

Alternatively, the preparation process of the traditional Chinese medicine composition according to the present invention may include the steps of:

1) extracting Radix Panacis Quinquefolii, *Ganoderma*, *Cordyceps* and/or fermented *Cordyceps sinensis* powder, and Flos Rosae Rugosae by adding methanol or ethanol, and recovering methanol or ethanol from the liquid extract to provide Extract I;

2) vaporizing the alcohol from the residual drugs, and adding water to extract the residual drugs to afford Extract II;

3) combining Extract I and Extract II, filtering and concentrating the combined extracts to an appropriate level, adding a pharmaceutically common auxiliary agent to produce a desired formulation by conventional processes in pharmaceutics.

Alternatively, the preparation process of the traditional Chinese medicine composition according to the present invention may include the steps of:

1) raw materials preparation, in which the materials are prepared according to a formulation wherein the Radix Panacis Quinquefolii and *Ganoderma* are sliced and the fermented *Cordyceps sinensis* powder is put into a cloth bag;

2) extraction and concentration, in which the materials processed in step 1) are soaked in water for 1 h, and then decoted for 1-3 times (1-2 h each time) with heating, the liquid extracts are combined and filtered, the liquid filtrate is concentrated to an appropriate level, the liquid concentrate is left to cool down, the impurities therein are then removed by ultracentrifuge, and the resulting concentrate is ready for use;

3) formulation preparation, in which the concentrate obtained from step 2) is prepared, alone or with added pharmaceutically acceptable auxiliary agents, into a desired formulation by conventional processes in pharmaceutics.

The medicine composition of the present invention may be formulated into any conventional dosage forms, including but not limited to tablets, granules, capsules, oral liquid, syrups, pills and the like, by using conventional methods for traditional Chinese formulations and adding any pharmaceutically acceptable auxiliary agent(s). Furthermore, the active components in the composition of the present invention may be formulated into any conventional oral dosage form by using conventional methods for traditional Chinese formulations and adding various conventional auxiliary agents required for preparation of various dosage forms, such as disintegrating agents, lubricants, surfactants, diluents, excipients, adsorbing carriers, binders and the like.

According to the present invention, the medicine composition composed of Radix Panacis Quinquefolii and/or Radix Et Rhizoma Ginseng, *Ganoderma*, and *Cordyceps* shows better therapeutic effects than the composition composed of Radix Panacis Quinquefolii, *Ganoderma*, and fermented *Cordyceps sinensis* powder in terms of relieving physical fatigue, reducing blood lipids, resisting oxidation, and enhancing anoxia endurance.

According to the present invention, the medicine composition composed of Radix Panacis Quinquefolii and/or Radix Et Rhizoma Ginseng, *Ganoderma, Cordyceps*, and Flos Rosae Rugosae shows better therapeutic effects than the composition composed of Radix Panacis Quinquefolii, *Ganoderma*, fermented *Cordyceps sinensis* powder and Flos Rosae Rugosae in terms of relieving physical fatigue, reducing blood lipids, resisting oxidation, and enhancing anoxia endurance.

According to the present invention, the medicine composition composed of Radix Panacis Quinquefolii and/or Radix Et Rhizoma Ginseng, *Ganoderma, Cordyceps*, and fermented *Cordyceps sinensis* powder shows better therapeutic effects than the composition composed of Radix Panacis Quinquefolii, *Ganoderma*, and fermented *Cordyceps sinensis* powder in terms of relieving physical fatigue, reducing blood lipids, resisting oxidation, and enhancing anoxia endurance.

According to the present invention, the medicine composition composed of Radix Panacis Quinquefolii and/or Radix Et Rhizoma Ginseng, *Ganoderma, Cordyceps*, fermented *Cordyceps sinensis* powder and Flos Rosae Rugosae shows more significant therapeutic effects than the composition composed of Radix Panacis Quinquefolii, *Ganoderma*, fermented *Cordyceps sinensis* powder and Flos Rosae Rugosae in terms of relieving physical fatigue, reducing blood lipids, resisting oxidation, and enhancing anoxia endurance.

In order to provide better understanding of the spirit of the present invention, the animal experiments and the results thereof on the medicine composition composed of Radix Panacis Quinquefolii and/or Radix Et Rhizoma Ginseng, *Ganoderma*, and fermented *Cordyceps sinensis* powder will be used below to demonstrate the novel use of the composition in the field of health foods and medicaments for relieving physical fatigue, reducing blood lipids, resisting oxidation, and enhancing anoxia endurance. Addition of *Cordyceps*, or substitution of *Cordyceps* for fermented *Cordyceps sinensis* powder, resulted in improved therapeutic effects. Addition of Flos Rosae Rugosae in the compositions can produce a synergetic effect.

Similarly, addition of any one of Radix Et Rhizoma Ginseng, Radix Pseudostellariae, Radix Codonopsis, Radix Astragali, and Semen Cuscutae or any combination thereof can lead to the same pharmacologic actions, despite the difference in the amounts in use.

(I) The Following Set of Animal Experiments Demonstrated that the TCM Composition (Radix Panacis Quinquefolii, *Ganoderma*, and Fermented *Cordyceps Sinensis* Powder) According to the Present Invention Showed the Effect of Relieving Physical Fatigue without Causing any Toxic or Adverse Effects, Details of which Will Be Described Below.

1. Materials and Methods 1.1 Sources and Processing of Samples

TCM composition I (Radix Panacis Quinquefolii, *Ganoderma*, and fermented *Cordyceps sinensis* powder) according to the present invention was provided by Jiangzhong Pharmaceutical Co. Ltd. as composite powder for oral liquid. This sample is present as brown solid powder and to be prepared in distilled water to have a desired concentration before use.

1.2 Laboratory Animals and Experimental Environments

CL (clean) healthy male ICR mice, each weighing 18 to 22 g, were provided by the Laboratory Animal Center, Peking University Health Science Center (Animal Certification Number: Medicinal Animal SCXK (Beijing)-2006-0008). They were fed in a SPF animal room (Certificate for Animal Experimental environments (SPF): Medicinal Animal No. 01-2055) with a feeding environmental temperature of 21 to 23° C. and relative humidity of 50% to 60%.

1.3 Experimental Methods 1.3.1 Animal Grouping 160 male ICR mice were divided randomly into 4 groups (40 animals in each group) based on their body weights. A blank control group, and test groups on a low dose, a medium dose, and a high dose of TCM composition I (as composite powder for oral liquid) according to the present invention were set up. Each animal group was further divided into 4 subgroups (10 animals in each subgroup).

1.3.2 Dosage Design

The recommended daily intake dose per person of the oral liquid of TCM composition I according to the present invention is 200 ml/60 kg BW (body weight). Every 1000 ml oral liquid of TCM composition according to the present invention is formulated with 120 g total crude drugs, and 1 g dry composite powder for the oral liquid of TCM composition I according to the present invention is equivalent to 11.41 g total crude drugs. Therefore, the recommended daily intake dose per person of the composite powder for the oral liquid of TCM composition I according to the present invention can be calculated as 2.10 g/60 kg BW. Based on this dose, daily intake doses for mice are calculated as 0.175 g/kg BW for the low-dose group, 0.350 g/kg BW for the medium-dose group, and 1.050 g/kg BW for the high-dose group, equivalent to 5, 10, and 30 times the daily intake dose for human, respectively. The samples were prepared in distilled water to make intragastric administration liquids having corresponding concentrations (i.e. 0.0175 g/ml, 0.0350 g/ml, 0.1050 g/ml) for experimentation. The intragastric administration amount for mice is calculated based on a ratio of 0.1 ml/10 g BW. The test groups each received one of the three doses of the intragastric administration liquids made from the composite powder for the oral liquid of TCM composition I according to the present invention every day, while the control group received an equal volume of distilled water by intragastric administration. The intragastric administrations were conducted once a day and continued for 30 days. All mice groups were fed with common feed and allowed free access to feed and water. After 30 days, all subgroups of mice were subjected to a function test on relieving of physical fatigue.

1.3.3 Burdened Swimming Experiment 30 minutes after given the last test sample, the 10 mice of the first subgroup in every group were each loaded a piece of lead weighing 5% of their body weight at the base of their tails. Then each burdened mouse was put into a swimming tank (with a depth≥30 cm, and water temperature of 25° C.+1.0° C.) to swim. The duration from the beginning of swimming to the death of the mouse was recorded as the burdened swimming time of the mouse.

1.3.4 Serum Urea Nitrogen Measurement 30 minutes after given the last test sample, the 10 mice of the second subgroup in every group were allowed to swim without any burden in 30° C. water for 90 min. After a 60-minute rest, their eyeballs were taken out, and about 0.5 ml whole blood was collected and placed in a 4° C. fridge for about 3 h. When coagulated, the blood was centrifuged at 2000 rpm for 15 min, and the serum was isolated for urea nitrogen content determination. The serum urea nitrogen was measured in Olympus AU400 automated Chemistry Analyzer (Japan), using the reagents provided by Daiichi Pure Chemicals Co., Ltd., Japan.

1.3.5 Liver Glycogen Measurement 30 minutes after given the last test sample, the 10 mice of the third subgroup in every group were sacrificed. The livers were taken out, rinsed with saline solution, and blotted with filter paper. 100 mg liver was precisely weighed out, and 8 ml TCA was added thereto. The sample in each tube was homogenized for 1 min, the homogenate was poured into a centrifuge tube and centrifuged at 3000 rpm for 15 min, and the supernatant was transferred into another tube. 1 ml of the supernatant was transferred into a 10 ml centrifuge tube to which 4 ml 95% ethanol was further added and thoroughly mixed until no interface was present between the two liquids. The opening of the centrifuge tube was sealed with a sealing film, and the tube was upright placed overnight at room temperature. After complete deposition, the tube was centrifuged at 3000 rpm for 15 min, the supernatant was then carefully discarded, and the tube was placed upside down for 10 min. Thereafter 2 ml distilled water was added to dissolve glycogen, and the glycogen content in liver was measured by the anthrone method.

1.3.6. Lactic Acid Measurement 30 minutes after the last intragastric administration, a 20 μl blood sample was taken from the tail of each of the 10 mice of the fourth subgroup in every group. The mice were then allowed to swim without any burden in 30° C. water for 10 min. Another two 20 μl blood samples were further taken 0 min and 20 min after swimming, respectively. Each of the three blood samples taken was added to a 0.48 ml 1% NaF solution and thoroughly mixed until clarity. Subsequently, 1.5 ml protein precipitating agent was added and mixed by shaking until homogenated. The mixture was centrifuged at 3000 rpm for 10 min, the supernatant was taken for lactic acid content determination, and the area under curve (AUC) under the blood lactic acid curve at 3 time points was calculated.

$$AUC \text{ under the blood lactic acid curve} = \frac{1}{2} * (\text{blood lactic acid level before swimming} + \text{blood lactic acid level 0 min after swimming}) * 10 + \frac{1}{2} * (\text{blood lactic acid level 0 min after swimming} + \text{blood lactic acid level after 20-min rest after swimming}) * 20$$

1.3.7 Statistic Methods

The experimental data are expressed as $\bar{x} \pm s$. One-way analysis of variance was employed to compare the measured indicators at the end of the experiments between the dosed test groups and the blank control group for difference, and $P<0.05$ indicates the difference is significant.

2. Results 2.1 Body Weight Gain of the Animals

Compared to the blank control group, the mice groups that received various doses of the composite powder for oral liquid of TCM composition I according to the present invention showed no significant difference in body weight (Table 1).

TABLE 1

The effect of the composite powder for oral liquid of TCM composition I according to the present invention on the body weight gain of mice (g, x̄ ± s).

| | Group Name | Dose (g/kgbw) | Number of Animals | Initial Body Weight | Final Body Weight |
|---|---|---|---|---|---|
| The first subgroup | Blank control group | 0.000 | 10 | 20.28 ± 2.14 | 42.13 ± 4.67 |
| | Low-dose group | 0.175 | 10 | 20.44 ± 1.55 | 40.71 ± 3.55 |
| | Medium-dose group | 0.350 | 10 | 20.46 ± 1.96 | 42.97 ± 2.55 |
| | High-dose group | 1.050 | 10 | 19.78 ± 1.30 | 41.11 ± 3.76 |
| The second subgroup | Blank control group | 0.000 | 10 | 19.76 ± 1.28 | 41.80 ± 3.72 |
| | Low-dose group | 0.175 | 10 | 19.84 ± 0.90 | 42.00 ± 4.04 |
| | Medium-dose group | 0.350 | 10 | 18.95 ± 1.39 | 41.10 ± 3.67 |
| | High-dose group | 1.050 | 10 | 19.42 ± 1.42 | 41.69 ± 3.98 |
| The third subgroup | Blank control group | 0.000 | 10 | 19.48 ± 0.74 | 41.55 ± 1.77 |
| | Low-dose group | 0.175 | 10 | 18.62 ± 1.39 | 40.89 ± 2.03 |
| | Medium-dose group | 0.350 | 10 | 18.88 ± 1.58 | 41.33 ± 3.80 |
| | High-dose group | 1.050 | 10 | 18.89 ± 1.26 | 42.43 ± 3.39 |
| The fourth subgroup | Blank control group | 0.000 | 10 | 18.88 ± 1.09 | 40.53 ± 1.73 |
| | Low-dose group | 0.175 | 10 | 18.23 ± 1.38 | 41.17 ± 3.28 |
| | Medium-dose group | 0.350 | 10 | 18.44 ± 1.43 | 41.04 ± 2.02 |
| | High-dose group | 1.050 | 10 | 18.82 ± 1.18 | 40.69 ± 3.79 |

2.2 The mice groups that received the low, medium, and high doses of the composite powder for oral liquid of TCM composition I according to the present invention showed a burdened swimming time remarkably longer than that of the blank control group ($P<0.05$) (Table 2).

TABLE 2

The effect of the composite powder for oral liquid of TCM composition I according to the present invention on the burdened swimming time of mice (x̄ ± s).

| Group Name | Dose (g/kgbw) | Number of Animals | Burdened Swimming Time (min) |
|---|---|---|---|
| Blank control group | 0.000 | 10 | 3.53 ± 1.19 |
| Low-dose group | 0.175 | 10 | 4.88 ± 1.98* |
| Medium-dose group | 0.350 | 10 | 5.35 ± 1.17* |
| High-dose group | 1.050 | 10 | 6.23 ± 0.98* |

*indicates significant difference from the blank control group ($P < 0.05$)

2.3 Compared to the blank control group, the mice groups that received various doses of the composite powder for oral liquid of TCM composition I according to the present invention showed no significant difference ($P>0.05$) in serum urea nitrogen level after 90-min unburdened swimming (Table 3).

2.4 The mice groups that received various doses of the composite powder for oral liquid of TCM composition I according to the present invention showed a liver glycogen level remarkably higher than that of the blank control group, and the differences are significant ($P<0.05$) (Table 3).

TABLE 3

The effect of the composite powder for oral liquid of TCM composition I according to the present invention on the serum urea nitrogen and liver glycogen levels of mice (x̄ ± s).

| Group Name | Dose (g/kgbw) | Number of Animals | Urea Nitrogen (mmol/L) | Liver Glycogen (mg/g liver tissue) |
|---|---|---|---|---|
| Blank control group | 0.000 | 10 | 10.59 ± 1.32 | 15.82 ± 5.64 |
| Low-dose group | 0.175 | 10 | 10.03 ± 1.62 | 22.31 ± 7.63* |
| Medium-dose group | 0.350 | 10 | 10.60 ± 1.54 | 26.40 ± 7.28* |
| High-dose group | 1.050 | 10 | 10.08 ± 1.37 | 27.34 ± 6.35* |

*indicates significant difference from the blank control group ($P < 0.05$)

2.5 The mice groups that received various doses of the composite powder for oral liquid of TCM composition I according to the present invention all showed an AUC under the blood lactic acid curve at 3 time points remarkably smaller than that of the blank control group, and the differences are significant ($P<0.05$); and the mice groups that received the various doses showed blood lactic acid levels immediately after swimming and after a 20-min rest after swimming remarkably lower than those of the blank control group ($P<0.05$) (Table 4).

TABLE 4

The effect of the composite powder for oral liquid of TCM composition I according to the present invention on the blood lactic acid level of mice (mg/L, x̄ ± s).

| Group Name | Dose (g/kgbw) | Number of Animals | Before Swimming | 0 min After Swimming | 20 min After Swimming | AUC |
|---|---|---|---|---|---|---|
| Blank control group | 0.000 | 10 | 200.00 ± 54.75 | 577.21 ± 53.21 | 322.24 ± 54.77 | 12883.88 ± 1031.09 |
| Low-dose group | 0.175 | 10 | 216.95 ± 60.20 | 500.10 ± 78.64* | 259.17 ± 45.66* | 11177.91 ± 1660.26* |
| Medium-dose group | 0.350 | 10 | 184.77 ± 58.52 | 488.21 ± 81.47* | 224.69 ± 47.16* | 10493.86 ± 1842.34* |
| High-dose group | 1.050 | 10 | 194.56 ± 43.40 | 450.54 ± 83.26* | 207.90 ± 42.63* | 9809.88 ± 1490.42* |

*indicates significant difference from the blank control group ($P < 0.05$)

3. Conclusion

The daily intake dose of the composite powder for oral liquid of TCM composition I according to the present invention recommended for human (i.e., 2.10 g/60 kg BW) was scaled up by 5, 10, and 30 times to set up a low-dose group, a medium-dose group, and a high-dose group, respectively, corresponding to the doses of 0.175 g, 0.350 g, and 1.050 g per kg BW. And a blank control group was further set up. CL healthy male ICR mice were continuously administered intragastrically with the test samples, and after 30 days experiments were conducted and related indicators were measured. $P<0.05$ indicates the experimental results show significant difference. The animal experiments demonstrated that the mice groups that received the low, medium, and high doses of the composite powder for oral liquid of TCM composition I according to the present invention are able to significantly reduce the AUCs under the blood lactic acid curve of the mice before, 0 min after, and 20 min after unburdened swimming, and to significantly increase the liver glycogen level of mice in a resting state. Furthermore, the mice groups that received the low, medium, and high doses of the composite powder for oral liquid of TCM composition I according to the present invention showed a burdened swimming time remarkably longer than that of the blank control group. According to the standards for defining a function of relieving physical fatigue provided in the Technical Standards for Testing and Assessment of Health Food (2003) issued by the Ministry of Health of the People's Republic of China, the composite powder for oral liquid of TCM composition I according to the present invention is believed to have a function of relieving physical fatigue.

(II). The Following Set of Animal Experiments Demonstrated that the Oral Liquid of TCM Composition II (Radix Panacis Quinquefolii, *Ganoderma*, Fermented *Cordyceps Sinensis* Powder, and Flos Rosae Rugosae) According to the Present Invention Showed the Effect of Relieving Physical Fatigue without Causing any Toxic or Adverse Effects, Details of which Will be Described Below.

1. Materials and Methods 1.1 Sources and Processing of Samples

The test medicine is TCM composition II (Radix Panacis Quinquefolii, *Ganoderma*, fermented *Cordyceps sinensis* powder, and Flos Rosae Rugosae) in a form of composite powder for oral liquid, which was provided by Jiangzhong Pharmaceutical Co. Ltd. This sample is present as brown solid powder and to be prepared in distilled water to have a desired concentration before use. 1 g of this dry composite powder is equivalent to 12.56 g total crude drugs.

TCM composition I (Radix Panacis Quinquefolii, *Ganoderma*, and fermented *Cordyceps sinensis* powder) was provided by Jiangzhong Pharmaceutical Co. Ltd. as composite powder. This sample is present as brown solid powder and to be prepared in distilled water to have a desired concentration before use. 1 g of this dry composite powder is equivalent to 11.41 g total crude drugs.

1.2 Laboratory Animals and Experimental Environments

CL healthy male Kunming mice, each weighing 18 to 22 g, were provided by the Laboratory Animal Center, Jiangxi University of Traditional Chinese Medicine (Certification Number: SCXK (Jiangxi)-2006-0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods 1.3.1 Animal Grouping 200 male Kunming mice were divided randomly into 4 groups (50 animals in each group) based on their body weights. A blank control group, test groups on a low dose, a medium dose, and a high dose of the composite powder for oral liquid of TCM composition II, and a group on the composite powder of TCM composition I, were set up. Each animal group was further divided into 4 subgroups (10 animals in each subgroup).

1.3.2 Dosage Design

The recommended daily intake dose per person of the test medicine, i.e. the composite powder for oral liquid of TCM composition II, is 200 ml/60 kg BW. Every 1000 ml oral liquid of TCM composition II is formulated with 120 g total crude drugs, and 1 g dry composite powder is equivalent to 12.56 g total crude drugs. Therefore, the recommended daily intake dose per person of the composite powder for oral liquid of TCM composition II can be calculated as 24 g crude drugs/60 kg BW. Based on this dose, daily intake doses for mice are calculated as 2.0 g crude drugs/kg BW for the low-dose group, 4.0 g crude drugs/kg BW for the medium-dose group, and 12 g crude drugs/kg BW for the high-dose group, equivalent to 5, 10, and 30 times the daily intake dose for human, respectively. The samples were prepared in distilled water to make intragastric administration liquids having corresponding concentrations (i.e. 0.0159 g dry powder/ml, 0.0318 g dry powder/ml, 0.0995 g dry powder/ml) for experimentation. The intragastric administration amount for mice was calculated based on a ratio of 0.1 ml/10 g BW.

The recommended daily intake dose per person of the composite powder of TCM composition I is 200 ml/60 kg BW. Every 1000 ml oral liquid of TCM composition II is formulated with 120 g total crude drugs, and 1 g dry composite powder of TCM composition I is equivalent to 11.41 g total crude drugs. A medium dose, i.e. 4.0 g crude drugs/kg BW (equivalent to 10 times the daily intake dose for human), was given to the group on TCM composition I. The sample was prepared in distilled water to make a 0.0350 g dry powder/ml intragastric administration liquid for experimentation. The intragastric administration amount was calculated based on a ratio of 0.1 ml/10 g BW. The blank control group was given an equal volume of distilled water by intragastric administration. The intragastric administrations were conducted once a day and continued for 30 days. All mice groups were fed with common feed and allowed free access to feed and water. After 30 days, all subgroups of mice were subjected to a function test on relieving of physical fatigue.

1.3.3 Burdened Swimming Experiment 30 minutes after given the last test sample, the 10 mice of the first subgroup in every group were each loaded a piece of lead weighing 5% of their body weight at the base of their tails. Then each burdened mouse was put into a swimming tank (with a depth≥30 cm, and water temperature of 25° C.±1.0° C.) to swim. The duration from the beginning of swimming to the death of the mouse was recorded as the burdened swimming time of the mouse.

1.3.4 Serum Urea Nitrogen Measurement 30 minutes after given the last test sample, the 10 mice of the second subgroup in every group were allowed to swim without any burden in 30° C. water for 90 min. After a 60-minute rest, their eyeballs were taken out, and about 0.5 ml whole blood was collected and placed in a 4° C. fridge for about 3 h. When coagulated, the blood was centrifuged at 2000 rpm for 15 min, and the serum was isolated for urea nitrogen content determination. The serum urea nitrogen was measured in Olympus AU400 automated Chemistry Analyzer (Japan), using the reagents provided by Daiichi Pure Chemicals Co., Ltd., Japan.

1.3.5 Liver Glycogen Measurement 30 minutes after given the last test sample, the 10 mice of the third subgroup in every group were sacrificed. The livers were taken out, rinsed with saline solution, and blotted with filter paper. 100 mg liver was precisely weighed out, and 8 ml TCA was added thereto. The sample in each tube was homogenized for 1 min, the homogenate was poured into a centrifuge tube and centrifuged at 3000 rpm for 15 min, and the supernatant was transferred into another tube. 1 ml of the supernatant was transferred into a 10 ml centrifuge tube to which 4 ml 95% ethanol was further added and thoroughly mixed until no interface was present between the two liquids. The opening of the centrifuge tube was sealed with a sealing film, and the tube was upright placed overnight at room temperature. After complete deposition, the tube was centrifuged at 3000 rpm for 15 min, the supernatant was then carefully discarded, and the tube was placed upside down for 10 min. Thereafter 2 ml distilled water was added to dissolve glycogen, and the glycogen content in liver was measured by the anthrone method.

1.3.6. Lactic Acid Measurement 30 minutes after the last intragastric administration, a 20 µl blood sample was taken from the tail of each of the 10 mice of the fourth subgroup in every group. The mice were then allowed to swim without any burden in 30° C. water for 10 min. Another two 20 µl blood samples were further taken 0 min and 20 min after swimming, respectively. Each of the three blood samples taken was added to a 0.48 ml 1% NaF solution and thoroughly mixed until clarity. Subsequently, 1.5 ml protein precipitating agent was added and mixed by shaking until homogenated. The mixture was centrifuged at 3000 rpm for 10 min, the supernatant was taken for lactic acid content determination, and the AUC under the blood lactic acid curve at 3 time points was calculated.

AUC under the blood lactic acid curve=½*(blood lactic acid level before swimming+blood lactic acid level 0 min after swimming)*10+½*(blood lactic acid level 0 min after swimming+blood lactic acid level after 20-min rest after swimming)*20

1.3.7 Statistic Methods

The experimental data are expressed as $\bar{x} \pm s$. One-way analysis of variance was employed to compare the measured indicators at the end of the experiments between the dosed test groups and the blank control group for difference. $P<0.05$ indicates the difference is significant, and $P<0.01$ indicates the difference is highly significant.

2. Results 2.1 Body Weight Gain of the Animals

Compared to the blank control group, the mice groups that received various doses of the composite powder for oral liquid of TCM composition II showed no significant difference in body weight. Compared to the group that received TCM composition I, the mice groups that received various doses of the composite powder for oral liquid of TCM composition II showed no significant difference in body weight. See Table 1 below for the results.

TABLE 1

The effect of the composite powder for oral liquid of TCM composition II on the body weight gain of mice (g, $\bar{x} \pm s$).

| | Group Name | Dose (g crude drugs/ kgbw) | Number of Animals | Initial Body Weight | Final Body Weight |
|---|---|---|---|---|---|
| The first subgroup | Blank control group | 0.0 | 10 | 20.66 ± 1.42 | 42.83 ± 4.21 |
| | Group on TCM composition I | 4.0 | 10 | 20.19 ± 1.50 | 41.65 ± 4.02 |
| | Low-dose group on test medicine | 2.0 | 10 | 20.40 ± 1.38 | 41.71 ± 4.28 |
| | Medium-dose group on test medicine | 4.0 | 10 | 20.41 ± 1.63 | 42.55 ± 2.96 |
| | High-dose group on test medicine | 12.0 | 10 | 20.12 ± 1.53 | 42.91 ± 3.86 |
| The second subgroup | Blank control group | 0.0 | 10 | 20.34 ± 1.62 | 41.80 ± 4.70 |
| | Group on TCM composition I | 4.0 | 10 | 20.25 ± 1.57 | 42.25 ± 3.67 |
| | Low-dose group on test medicine | 2.0 | 10 | 20.14 ± 1.37 | 42.18 ± 4.34 |
| | Medium-dose group on test medicine | 4.0 | 10 | 20.05 ± 1.59 | 41.16 ± 3.92 |
| | High-dose group on test medicine | 12.0 | 10 | 20.42 ± 1.54 | 42.69 ± 4.98 |
| The third subgroup | Blank control group | 0.0 | 10 | 20.48 ± 0.96 | 42.55 ± 4.77 |
| | Group on TCM composition I | 4.0 | 10 | 20.22 ± 0.98 | 42.29 ± 3.08 |
| | Low-dose group on test medicine | 2.0 | 10 | 20.15 ± 1.39 | 41.89 ± 4.13 |
| | Medium-dose group on test medicine | 4.0 | 10 | 20.18 ± 1.52 | 41.33 ± 3.32 |
| | High-dose group on test medicine | 12.0 | 10 | 20.29 ± 1.23 | 42.34 ± 4.37 |
| The fourth subgroup | Blank control group | 0.0 | 10 | 20.31 ± 1.19 | 42.53 ± 3.72 |
| | Group on TCM composition I | 4.0 | 10 | 20.09 ± 1.46 | 41.45 ± 3.48 |
| | Low-dose group on test medicine | 2.0 | 10 | 20.23 ± 1.35 | 41.58 ± 3.68 |
| | Medium-dose group on test medicine | 4.0 | 10 | 20.41 ± 1.03 | 41.74 ± 4.02 |
| | High-dose group on test medicine | 12.0 | 10 | 20.20 ± 1.26 | 41.69 ± 3.82 |

2.2 Effects on the Burdened Swimming Time of Mice

Compared to the blank control group, the mice groups that received the low, medium, and high doses of the composite powder for oral liquid of TCM composition II and the mice group that received TCM composition I all showed a remarkably longer burdened swimming time ($P<0.05$). Compared to the group that received TCM composition I, the mice groups that received the medium and high doses of the composite powder for oral liquid of TCM composition II all showed a remarkably longer burdened swimming time ($P<0.05$). See Table 2 below for the results.

TABLE 2

The effect of the composite powder for oral liquid of TCM composition II on the burdened swimming time of mice ($\bar{x} \pm s$).

| Group Name | Dose (g crude drugs/kgbw) | Number of Animals | Burdened Swimming Time (min) |
|---|---|---|---|
| Blank control group | 0.0 | 10 | 3.78 ± 0.88 |
| Group on TCM composition I | 4.0 | 10 | 4.89 ± 1.17* |
| Low-dose group on test medicine | 2.0 | 10 | 4.83 ± 1.07* |
| Medium-dose group on test medicine | 4.0 | 10 | 5.84 ± 0.90*▲ |
| High-dose group on test medicine | 12.0 | 10 | 6.49 ± 1.08*▲ |

*P < 0.05 compared to the blank control group;
▲P < 0.05 compared to the group on TCM composition I.

2.3 Effect on Serum Urea Nitrogen Level of Mice

Compared to the blank control group, the mice groups that received the low, medium, and high doses of the composite powder for oral liquid of TCM composition II and the mice group that received TCM composition I showed no significant difference (P>0.05) in serum urea nitrogen level after 90-min unburdened swimming. Compared to the group that received TCM composition I, the mice groups that received the low, medium, and high doses of the composite powder for oral liquid of TCM composition II showed no significant difference (P>0.05) in serum urea nitrogen level after 90-min unburdened swimming. See Table 3 below for the results.

2.4 Effect on Liver Glycogen Level of Mice

The mice groups that received the low, medium, and high doses of the composite powder for oral liquid of TCM composition II and the mice group that received TCM composition I showed a liver glycogen level remarkably higher than that of the blank control group, and the differences are significant (P<0.05). The mice groups that received the medium and high doses of the composite powder for oral liquid of TCM composition II showed a liver glycogen level remarkably higher than that of the group that received TCM composition I, and the differences are significant (P<0.05, P<0.01). See Table 3 below for the results.

TABLE 3

The effect of the composite powder for oral liquid of TCM composition II on the serum urea nitrogen and liver glycogen levels of mice ($\bar{x} \pm s$).

| Group Name | Dose (g crude drugs/kgbw) | Number of Animals | Urea Nitrogen (mmol/L) | Liver Glycogen (mg/g liver tissue) |
|---|---|---|---|---|
| Blank control group | 0.0 | 10 | 10.22 ± 1.68 | 15.78 ± 3.60 |
| Group on TCM composition I | 4.0 | 10 | 10.56 ± 2.02 | 20.91 ± 3.97 |
| Low-dose group on test medicine | 2.0 | 10 | 10.80 ± 2.62 | 21.28 ± 3.91* |
| Medium-dose group on test medicine | 4.0 | 10 | 10.44 ± 1.76 | 24.51 ± 3.25*▲ |
| High-dose group on test medicine | 12.0 | 10 | 10.60 ± 1.78 | 25.21 ± 2.58*▲▲ |

*P < 0.05 compared to the blank control group;
▲P < 0.05 and
▲▲P < 0.01 compared to the group on TCM composition I.

2.5 Effect on Blood Lactic Acid Level of Mice

The mice groups that received various doses of the composite powder for oral liquid of TCM composition II and the mice group that received TCM composition I all showed a blood lactic acid level immediately after swimming, a blood lactic acid level after a 20-min rest after swimming, and an AUC all remarkably lower than those of the blank control group (P<0.01). The mice groups that received the medium and high doses of the composite powder for oral liquid of TCM composition II all showed a blood lactic acid level immediately after swimming, a blood lactic acid level after a 20-min rest after swimming, and an AUC all remarkably lower than those of the comparative group that received TCM composition I (P<0.05, P<0.01) See Table 4 below for the results.

TABLE 4

The effect of the composite powder for oral liquid of TCM composition II on the blood lactic acid level of mice (mg/L, $\bar{x} \pm s$).

| Group Name | Dose (g crude drugs/kgbw) | Number of Animals | Before Swimming | 0 min After Swimming | 20 min After Swimming | AUC |
|---|---|---|---|---|---|---|
| Blank control group | 0.0 | 10 | 208.50 ± 37.50 | 580.30 ± 57.45 | 324.40 ± 35.61 | 12991.00 ± 610.16 |
| Group on TCM composition I | 4.0 | | 213.9 ± 40.47 | 497.90 ± 52.11** | 266.00 ± 29.89 | 11198.00 ± 907.84 |
| Low-dose group on test medicine | 2.0 | 10 | 220.80 ± 37.95 | 498.80 ± 73.33** | 255.80 ± 24.95** | 11144.00 ± 1192.90** |
| Medium-dose group on test medicine | 4.0 | 10 | 203.30 ± 38.80 | 445.60 ± 46.77**▲ | 234.60 ± 36.84**▲ | 10096.50 ± 1224.14**▲ |
| High-dose group on test medicine | 12.0 | 10 | 211.90 ± 34.89 | 421.30 ± 83.26**▲▲ | 207.80 ± 20.50**▲▲ | 9457.00 ± 769.70**▲▲ |

*P < 0.05 compared to the blank control group;
▲P < 0.05 and
▲▲P < 0.01 compared to the group on TCM composition I.

3. Conclusion

The daily intake dose of the composite powder for oral liquid of TCM composition II according to the present invention recommended for human (i.e., 24.0 g crude drugs/60 kg BW) was scaled up by 5, 10, and 30 times to set up a low-dose group, a medium-dose group, and a high-dose group, respectively, corresponding to the doses of 2.0 g, 4.0 g, and 12.0 g crude drugs per kg BW. A blank control group and a comparative group on TCM composition I were further set up. CL healthy male Kunming mice were continuously administered intragastrically with the test samples, and after 30 days experiments were conducted and related indicators were measured. $P<0.05$ indicates the experimental results show significant difference, and $P<0.01$ indicates the experimental results show highly significant difference. The animal experiments demonstrated that the mice groups that received the low, medium, and high doses of the composite powder for oral liquid of TCM composition II are able to significantly reduce the AUCs under the blood lactic acid curve of the mice before, 0 min after, and 20 min after unburdened swimming, and to significantly increase the liver glycogen level of mice in a resting state. Furthermore, the mice groups that received the low, medium, and high doses of the composite powder for oral liquid of TCM composition II showed a burdened swimming time remarkably longer than that of the blank control group. Compared to the comparative group that received TCM composition I, the mice groups that received the medium and high doses of the composite powder for oral liquid of TCM composition II are able to significantly reduce the AUCs under the blood lactic acid curve of the mice before, 0 min after, and 20 min after unburdened swimming, and to significantly increase the liver glycogen level of mice in a resting state. Furthermore, the mice groups that received the medium and high doses of the composite powder for oral liquid of TCM composition II showed a burdened swimming time remarkably longer than that of the comparative group that received TCM composition I. The composite powder for oral liquid of TCM composition II is believed to have a function of relieving physical fatigue more effectively than the comparative group on TCM composition I.

(III) The Following Set of Animal Experiments Demonstrated that TCM Composition I (Radix Panacis Quinquefolii, *Ganoderma*, and Fermented *Cordyceps Sinensis* Powder) According to the Present Invention has the Function of Helping Reduce Blood Lipids without Causing any Toxic or Adverse Effects. The Animal Experiments are Reported and Described Below.

1. Materials and Methods 1.1 Sources and Processing of Samples

TCM composition I (Radix Panacis Quinquefolii, *Ganoderma*, and fermented *Cordyceps sinensis* powder) according to the present invention was provided by Jiangzhong Pharmaceutical Co. Ltd. as composite powder for oral liquid. This sample is present as brown solid powder and to be prepared in distilled water to have a desired concentration before use.

1.2 Laboratory Animals and Experimental Environments

CL healthy male SD rats, each weighing 150 to 200 g, were provided by the Laboratory Animal Center, Peking University Health Science Center (Certification Number: SCXK11-00-0004). They were fed in a SPF animal room (Certificate for Animal Experimental environments (SPF): Medicinal Animal No. 01-2055) with a feeding environmental temperature of 21 to 23° C. and relative humidity of 50% to 60%.

1.3 Experimental Methods 1.3.1 Animal Grouping 50 male SD rats, each weighing 150-200 g, were adaptively fed with basic feed for one week. Thereafter blood samples were taken from the base of their tails for determination of serum levels of total cholesterol (TC), triglyceride (TG), and high-density lipoprotein-cholesterol (HDL-C). The rats were divided into 5 groups (10 animals in each group) based on their TC level and body weights. A basic-feed control group, a high-fat-feed control group, and three test groups on low, medium and high doses were set up.

1.3.2 Dosage Design

The recommended daily intake dose per person of the oral liquid of TCM composition I according to the present invention is 200 ml/60 kg BW. Every 1000 ml oral liquid of TCM composition according to the present invention is formulated with 120 g total crude drugs, and 1 g dry composite powder for the oral liquid of TCM composition I according to the present invention is equivalent to 11.41 g total crude drugs. Therefore, the recommended daily intake dose per person of the composite powder for the oral liquid of TCM composition I according to the present invention can be calculated as 2.10 g/60 kg BW. Based on this dose, daily intake doses for rats are calculated as 0.175 g/kg BW for the low-dose group, 0.350 g/kg BW for the medium-dose group, and 1.050 g/kg BW for the high-dose group, equivalent to 5, 10, and 30 times the daily intake dose for human, respectively. When the experiment was initiated, only the rats in the basic-feed control group were fed with basic feed, and the other groups of rats were all fed with high-fat feed (composition of the high-fat feed: 78.8% basic feed, 1% cholesterol, 10% custard powder, 10% lard, and 0.2% chocolate). The samples were prepared in distilled water to make intragastric administration liquids having corresponding concentrations (i.e. 0.0175 g/ml, 0.0350 g/ml, 0.1050 g/ml) for experimentation. The intragastric administration amount is 1 ml/100 g BW.

The test groups each received one of the three doses of the intragastric administration liquids made from the composite powder for oral liquid of TCM composition I according to the present invention every day, while the basic-feed control group and the high-fat-feed control group received an equal volume of distilled water by intragastric administration. The intragastric administrations were conducted once a day and continued for 30 days, and body weights were measured every week. All rats groups were allowed free access to feed and water. After 30 days, blood samples were taken from the femoral artery, and serum samples were isolated for determination of related indicators.

1.3.3 Examined Indicators

The levels of TC (by enzymatic means), TG (by enzymatic means), and HDL-C (by a direct method) were measured in Olympus AU400 automated Chemistry Analyzer (Japan), using the reagents provided by Daiichi Pure Chemicals Co., Ltd., Japan.

1.3.4 Statistic Methods

The experimental data are expressed as $\bar{x} \pm s$. One-way analysis of variance was employed to compare the serum levels of TC, TG, and HDL-C of the rats at the end of the experiments between the dosed test groups and the high-fat control group for difference, and $P<0.05$ indicates the difference is significant.

2. Results 2.1 Effect of the composite powder for oral liquid of TCM composition I according to the present invention on the body weight of the rats in the blood lipid experiment Compared to the high-fat-feed control group, the rats groups that received various doses of the composite powder for oral liquid of TCM composition I according to the present invention showed no significant difference in body weight (see Table 1 below).

TABLE 1

The effect of the composite powder for oral liquid of TCM composition I according to the present invention on the body weight of the rats in the blood lipid experiment (g, $\bar{x} \pm s$).

| Group Name | n | Week 0 | Week 1 | Week 2 | Week 3 | Week 4 |
|---|---|---|---|---|---|---|
| Basic-feed control group | 10 | 178.6 ± 7.4 | 234.7 ± 12.9 | 285.7 ± 18.7 | 326.6 ± 19.7 | 373.3 ± 22.4 |
| High-fat-feed control group | 10 | 176.9 ± 5.5 | 230.2 ± 9.2 | 278.9 ± 14.7 | 330.3 ± 18.2 | 381.3 ± 20.8 |
| Group on 0.175 g/kgbw | 10 | 174.8 ± 6.2 | 234.8 ± 9.5 | 286.5 ± 14.6 | 326.3 ± 12.3 | 376.9 ± 14.1 |
| Group on 0.350 g/kgbw | 10 | 177.3 ± 6.7 | 235.0 ± 6.3 | 283.6 ± 11.7 | 322.6 ± 15.6 | 364.2 ± 22.4 |
| Group on 1.050 g/kgbw | 10 | 176.1 ± 7.8 | 232.0 ± 12.3 | 286.4 ± 14.1 | 322.0 ± 19.7 | 366.1 ± 27.2 |

2.2 Effect of the composite powder for oral liquid of TCM composition I according to the present invention on the blood lipid level of the rats 2.2.1 At the beginning of the experiment, there was no significant difference in serum levels of TC, TG and HDL-C among the rats groups (see Table 2 below).

TABLE 2

Serum levels of TC, TG, and HDL-C of the rats at the beginning of the experiment (mmol/L, $\bar{X} \pm S$)

| Group Name | Number of Animals | TC | TG | HDL-C |
|---|---|---|---|---|
| Basic-feed control group | 10 | 2.59 ± 0.30 | 1.29 ± 0.34 | 1.04 ± 0.12 |
| High-fat-feed control group | 10 | 2.58 ± 0.31 | 1.27 ± 0.34 | 1.08 ± 0.08 |
| Group on 0.175 g/kgbw | 10 | 2.59 ± 0.27 | 1.21 ± 0.37 | 1.07 ± 0.07 |
| Group on 0.350 g/kgbw | 10 | 2.61 ± 0.38 | 1.21 ± 0.34 | 1.08 ± 0.13 |
| Group on 1.050 g/kgbw | 10 | 2.58 ± 0.25 | 1.22 ± 0.33 | 1.05 ± 0.08 |

2.2.2 At the end of the experiment, the rats in the high-fat-feed control group showed the serum levels of TC and TG significantly higher than those of the basic-feed control group, indicating successful establishment of a high-fat model. The rats groups that received various doses of the composite powder for oral liquid of TCM composition I according to the present invention showed a serum TC level lower than that of the high-fat-feed control group, and the difference is significant (P<0.05). The rats groups that received the medium and high doses of the composite powder for oral liquid of TCM composition I according to the present invention showed a serum TG level lower than that of the high-fat-feed control group, and the difference is significant (P<0.05). Compared to the high-fat-feed control group, the rats groups that received various doses of the composite powder for oral liquid of TCM composition I according to the present invention showed no significant difference in serum HDL-C level. See Table 3 below.

TABLE 3

The effect of the composite powder for oral liquid of TCM composition I according to the present invention on the serum levels of TC, TG, and HDL-C of the rats (mmol/L, $\bar{X} \pm S$)

| Group Name | Number of Animals | TC | TG | HDL-C |
|---|---|---|---|---|
| Basic-feed control group | 10 | 2.61 ± 0.25* | 1.30 ± 0.29* | 1.05 ± 0.12 |
| High-fat-feed control group | 10 | 3.72 ± 0.48 | 1.78 ± 0.25 | 1.09 ± 0.08 |
| Group on 0.175 g/kgbw | 10 | 3.17 ± 0.63* | 1.68 ± 0.25 | 1.11 ± 0.07 |
| Group on 0.350 g/kgbw | 10 | 3.19 ± 0.59* | 1.42 ± 0.32* | 1.08 ± 0.12 |
| Group on 1.050 g/kgbw | 10 | 3.25 ± 0.58* | 1.27 ± 0.30* | 1.11 ± 0.14 |

*indicates significant difference from the high-fat-feed control group (P < 0.05)

3. Conclusion

The daily intake dose of the composite powder for oral liquid of TCM composition I according to the present invention recommended for human (i.e., 2.10 g/60 kg BW) was scaled up by 5, 10, and 30 times to set up a low-dose group, a medium-dose group, and a high-dose group, respectively, corresponding to the doses of 0.175 g, 0.350 g, and 1.050 g per kg BW. A basic-feed control group and a high-fat-feed control group were further set up. CL healthy male SD rats were continuously administered intragastrically with the test samples, and after 30 days the related indicators were measured. P<0.05 indicates the experimental results show significant difference. The animal experiments demonstrated that, compared to the high-fat-feed control group, the rats groups that received the low, medium, and high doses of the composite powder for oral liquid of TCM composition I according to the present invention showed a significantly lower level of serum total cholesterol (TC), and the rats groups that received the medium and high doses showed a significantly lower level of triglyceride (TG). According to the standards for defining a function of helping reduce blood lipids provided in the *Technical Standards for Testing and Assessment of Health Food* (2003) issued by the Ministry of Health of the People's Republic of China, the composite powder for oral liquid of TCM composition I according to the present invention is believed to have a function of helping reduce blood lipids.

(IV). The Following Set of Animal Experiments Demonstrated that the Oral Liquid Of TCM Composition II (Radix Panacis Quinquefolii, *Ganoderma*, Fermented *Cordyceps Sinensis* Powder, and Flos Rosae Rugosae) According to the Present Invention has the Function of Reducing Blood Lipids without Causing any Toxic or Adverse Effects, Details of which Will be Described Below.

1. Materials and Methods
1.1 Sources and Processing of Samples

The test medicine is TCM composition II (Radix Panacis Quinquefolii, *Ganoderma*, fermented *Cordyceps sinensis* powder, and Flos Rosae Rugosae) in a form of composite powder for oral liquid, which was provided by Jiangzhong Pharmaceutical Co. Ltd. This sample is present as brown solid powder and to be prepared in distilled water to have a desired concentration before use. 1 g of this dry composite powder is equivalent to 12.56 g total crude drugs.

TCM composition I (Radix Panacis Quinquefolii, *Ganoderma*, and fermented *Cordyceps sinensis* powder) was provided by Jiangzhong Pharmaceutical Co. Ltd. as composite powder. This sample is present as brown solid powder and to be prepared in distilled water to have a desired concentration before use. 1 g of this dry composite powder is equivalent to 11.41 g total crude drugs.

1.2 Laboratory Animals and Experimental Environments

Healthy male SD rats, each weighing 150 to 200 g, were provided by the Laboratory Animal Center, Jiangxi University of Traditional Chinese Medicine (SCXK (Jiangxi)-2006-

0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods 1.3.1 Animal Grouping 60 male SD rats, each weighing 150-200 g, were adaptively fed with basic feed for one week. Thereafter blood samples were taken from the base of their tails for determination of serum levels of total cholesterol (TC), triglyceride (TG), and high-density lipoprotein-cholesterol (HDL-C). The rats were divided into 6 groups (10 animals in each group) based on their TC level and body weights. A basic-feed control group, a high-fat-feed control group, a comparative group on TCM composition I, and three test groups on low, medium and high doses were set up.

1.3.2 Dosage Design

The recommended daily intake dose per person of the composite powder for oral liquid of TCM composition II is 200 ml/60 kg BW. Every 1000 ml oral liquid of TCM composition II is formulated with 120 g total crude drugs, and 1 g dry composite powder is equivalent to 12.56 g total crude drugs. Therefore, the recommended daily intake dose per person of the composite powder for oral liquid of TCM composition II can be calculated as 24 g crude drugs/60 kg BW. Based on this dose, daily intake doses for rats are calculated as 1.2 g crude drugs/kg BW for the low-dose group, 2.4 g crude drugs/kg BW for the medium-dose group, and 7.2 g crude drugs/kg BW for the high-dose group, equivalent to 5, 10, and 30 times the daily intake dose for human, respectively.

The recommended daily intake dose per person of the composite powder of TCM composition I is 200 ml/60 kg BW. Every 1000 ml oral liquid of TCM composition II is formulated with 120 g total crude drugs, and 1 g dry composite powder of TCM composition I is equivalent to 11.41 g total crude drugs. A medium dose, i.e. 2.4 g crude drugs/kg BW (equivalent to 10 times the daily intake dose for human), was given to the group on TCM composition I.

When the experiment was initiated, only the rats in the basic-feed control group were fed with basic feed, and the other groups of rats were all fed with high-fat feed (composition of the high-fat feed: 78.8% basic feed, 1% cholesterol, 10% custard powder, 10% lard, and 0.2% chocolate).

The test samples were prepared in distilled water to make intragastric administration liquids having corresponding concentrations (i.e. 0.0095 g dry powder/ml, 0.0190 g dry powder/ml, 0.0597 g dry powder/ml) for experimentation. The intragastric administration amount thereof was 1 ml/100 g BW. The test groups each received one of the three doses of the intragastric administration liquids made from the composite powder for oral liquid of TCM composition II.

TCM composition I was prepared in distilled water to make an intragastric administration liquid at a concentration of 0.0190 g dry powder/ml for experimentation. The intragastric administration amount thereof was 1 ml/100 g BW. The basic-feed control group and the high-fat-feed control group received an equal volume of distilled water by intragastric administration.

The intragastric administrations were conducted once a day and continued for 30 days, and body weights were measured every week. All rats groups were allowed free access to feed and water. After 30 days, blood samples were taken from the femoral artery, and serum samples were isolated for determination of related indicators.

1.3.3 Examined Indicators

The levels of TC (by enzymatic means), TG (by enzymatic means), and HDL-C (by a direct method) were measured in Beckman-CX7 automated blood chemistry analyzer, using the reagents purchased from Nanjing Jiancheng.

1.3.4 Statistic Methods

The experimental data are expressed as $\bar{x} \pm s$. One-way analysis of variance was employed to compare the serum levels of TC, TG, and HDL-C of the rats at the end of the experiments between the dosed test groups and the high-fat control group for difference. $P<0.05$ indicates the difference is significant, and $P<0.01$ indicates the difference is highly significant.

2. Results 2.1 Effect of the Composite Powder for Oral Liquid of TCM Composition II on the Body Weight of the Rats in the Experiments.

Compared to the high-fat-feed control group, the rats groups that received various doses of the composite powder for oral liquid of TCM composition II and the rats group that received TCM composition I showed no significant difference in body weight. Compared to the comparative rats group that received TCM composition I, the rats groups that received various doses of the composite powder for oral liquid of TCM composition II showed no significant difference in body weight. (see Table 1 below).

TABLE 1

The effect of the composite powder for oral liquid of TCM composition II on the body weight of the rats in the experiments (g, $\bar{x} \pm s$).

| Group Name | Dose (g crude drugs/kgbw) | n | Week 0 | Week 1 | Week 2 | Week 3 | Week 4 |
|---|---|---|---|---|---|---|---|
| Basic-feed control group | 0.0 | 10 | 175.3 ± 10.2 | 225.9 ± 15.6 | 276.2 ± 19.2 | 330.6 ± 29.4 | 380.5 ± 32.4 |
| High-fat-feed control group | 0.0 | 10 | 173.9 ± 8.6 | 231.1 ± 12.3 | 268.1 ± 20.1 | 321.2 ± 28.2 | 372.6 ± 30.4 |
| Group on TCM composition I | 2.4 | 10 | 179.9 ± 8.9 | 226.8 ± 12.7 | 268.9 ± 19.4 | 334.3 ± 28.2 | 383.9 ± 30.5 |
| Low-dose group on test medicine | 1.2 | 10 | 177.8 ± 9.5 | 224.5 ± 12.5 | 276.3 ± 18.4 | 336.5 ± 22.3 | 386.6 ± 24.1 |
| Medium-dose group on test medicine | 2.4 | 10 | 180.6 ± 10.7 | 225.1 ± 11.4 | 273.2 ± 18.7 | 329.0 ± 25.6 | 369.8 ± 22.6 |
| High-dose group on test medicine | 7.2 | 10 | 179.4 ± 10.8 | 230.2 ± 15.6 | 276.4 ± 20.2 | 332.6 ± 29.5 | 372.5 ± 27.8 |

2.2 Effect of the Composite Powder for Oral Liquid of TCM Composition II on the blood lipid level of the rats At the beginning of the experiment, there was no significant difference in serum levels of TC, TG and HDL-C among the rats groups (see Table 2 below). At the end of the experiment, the rats in the high-fat-feed control group showed the serum levels of TC and TG significantly higher than those of the basic-feed control group, indicating successful establishment of a high-fat model. The rats groups that received various doses of the composite powder for oral liquid of TCM composition II and the rats group that received TCM composition I showed a serum TC level lower than that of the high-fat-feed control group, and the difference is significant ($P<0.05$). The rats groups that received the low, medium, and high doses of the composite powder for oral liquid of TCM composition II and the rats group that received TCM composition I showed a serum TG level lower than that of the high-fat-feed control group, and the difference is significant ($P<0.05$). Compared to the high-fat-feed control group, the rats groups that received the low, medium, and high doses of the composite powder for oral liquid of TCM composition II and the rats group that received TCM composition I showed no significant difference in serum HDL-C level.

The rats groups that received the medium and high doses of the composite powder for oral liquid of TCM composition II showed a serum TC level lower than that of the comparative rats group that received TCM composition I, and the difference is significant ($P<0.05$). The rats groups that received the medium and high doses of the composite powder for oral liquid of TCM composition II showed a serum TG level lower than that of the comparative rats group that received TCM composition I, and the difference is significant ($P<0.05$). Compared to the comparative rats group that received TCM composition I, the rats groups that received the low, medium, and high doses of the composite powder for oral liquid of TCM composition II showed no significant difference in serum HDL-C level. See Table 3 below for the results.

TABLE 2

Serum levels of TC, TG, and HDL-C of the rats at the beginning of the experiment (mmol/L, $\bar{X} \pm S$)

| Group Name | Dose (g crude drugs/ kgbw) | Number of Animals | TC | TG | HDL-C |
|---|---|---|---|---|---|
| Basic-feed control group | 0.0 | 10 | 2.66 ± 0.36 | 1.39 ± 0.33 | 1.16 ± 0.12 |
| High-fat-feed control group | 0.0 | 10 | 2.68 ± 0.38 | 1.37 ± 0.30 | 1.18 ± 0.14 |
| Group on TCM composition I | 2.4 | 10 | 2.68 ± 0.32 | 1.37 ± 0.34 | 1.19 ± 0.18 |
| Low-dose group on test medicine | 1.2 | 10 | 2.69 ± 0.37 | 1.33 ± 0.32 | 1.17 ± 0.17 |
| Medium-dose group on test medicine | 2.4 | 10 | 2.71 ± 0.28 | 1.31 ± 0.38 | 1.18 ± 0.20 |
| High-dose group on test medicine | 7.2 | 10 | 2.64 ± 0.35 | 1.32 ± 0.35 | 1.15 ± 0.16 |

TABLE 3

The effect of the composite powder for oral liquid of TCM composition II on the serum levels of TC, TG, and HDL-C of the rats (mmol/L, $\bar{X} \pm S$)

| Group Name | Dose (g crude drugs/ kgbw) | Number of Animals | TC | TG | HDL-C |
|---|---|---|---|---|---|
| Basic-feed control group | 0.0 | 10 | 2.72 ± 0.28* | 1.41 ± 0.25* | 1.16 ± 0.16 |
| High-fat-feed control group | 0.0 | 10 | 3.86 ± 0.33 | 1.87 ± 0.29 | 1.19 ± 0.18 |
| Group on TCM composition I | 2.4 | 10 | 3.27 ± 0.43* | 1.48 ± 0.22* | 1.16 ± 0.16 |
| Low-dose group on test medicine | 1.2 | 10 | 3.19 ± 0.39* | 1.42 ± 0.32* | 1.21 ± 0.17 |
| Medium-dose group on test medicine | 2.4 | 10 | 2.55 ± 0.28*▲ | 1.12 ± 0.30*▲ | 1.18 ± 0.20 |
| High-dose group on test medicine | 7.2 | 10 | 2.25 ± 0.26*▲ | 0.92 ± 0.20*▲ | 1.21 ± 0.24 |

*$P < 0.05$ and
**$P < 0.05$ compared to the high-fat-feed control group;
▲$P < 0.05$ and
▲▲$P < 0.01$ compared to the group on TCM composition I.

3. Conclusion

The daily intake dose of the composite powder for oral liquid of TCM composition II recommended for human (i.e., 24 g crude drugs/60 kg BW) was scaled up by 5, 10, and 30 times to set up a low-dose group, a medium-dose group, and a high-dose group, respectively, corresponding to the doses of 1.2 g, 2.4 g, and 7.2 g crude drugs per kg BW. A basic-feed control group and a high-fat-feed control group were further set up. CL healthy male SD rats were continuously administered intragastrically with the test samples, and after 30 days the related indicators were measured. $P<0.05$ indicates the experimental results show significant difference. The animal experiments demonstrated that the rats groups that received the low, medium, and high doses of the composite powder for oral liquid of TCM composition II showed the levels of serum total cholesterol (TC) and serum triglyceride (TG) significantly lower than those of the high-fat-feed control group, and that the rats groups that received the medium and high doses of the composite powder for oral liquid of TCM composition II showed the levels of serum total cholesterol (TC) and serum triglyceride (TG) significantly lower than those of the comparative group that received TCM composition I. The composite powder for oral liquid of TCM composition II is believed to have a function of helping reduce blood lipids more effectively than the group on TCM composition I.

(V) The Following Set of Animal Experiments Demonstrated that TCM Composition I (Radix Panacis Quinquefolii, *Ganoderma*, and Fermented *Cordyceps Sinensis* Powder) According to the Present Invention Showed the Effect Of Resisting Oxidation in Mice without Causing any Toxic or Adverse Effects. The Animal Experiments are Reported and Described Below.

1. Materials and Methods 1.1 Sources and Processing of Samples

TCM composition I (Radix Panacis Quinquefolii, *Ganoderma*, and fermented *Cordyceps sinensis* powder) was provided by Jiangzhong Pharmaceutical Co. Ltd. as composite powder. This sample is present as brown solid powder and to be prepared in distilled water to have a desired concentration before use.

1.2 Laboratory Animals and Experimental Environments

CL healthy male ICR mice, each weighing 18 to 22 g, were provided by the Laboratory Animal Center, Peking University Health Science Center (Animal Certification Number: Medicinal Animal SCXK (Beijing)-2006-0008). They were fed in a SPF animal room (Certificate for Animal Experimental environments (SPF): Medicinal Animal No. 01-2055) with a feeding environmental temperature of 21 to 23° C. and relative humidity of 50% to 60%.

1.3 Experimental Methods 1.3.1 Animal Grouping 50 male ICR mice were divided randomly into 5 groups based on their body weights. A blank control group, a model control group, and test groups on a low dose, a medium dose, and a high dose of TCM composition I (composite powder for oral liquid) were set up, with 10 animals in each group.

1.3.2 Dosage Design

The recommended daily intake dose per person of the oral liquid of TCM composition I is 200 ml/60 kg BW. Every 1000 ml oral liquid of TCM composition I is formulated with 120 g total crude drugs, and 1 g dry composite powder for oral liquid of TCM composition I is equivalent to 11.41 g total crude drugs. Therefore, the recommended daily intake dose per person of the composite powder for oral liquid of TCM composition I can be calculated as 2.10 g/60 kg BW. Based on this dose, daily intake doses for mice are calculated as 0.175 g/kg BW for the low-dose group, 0.350 g/kg BW for the medium-dose group, and 1.050 g/kg BW for the high-dose group, equivalent to 5, 10, and 30 times the daily intake dose for human, respectively. The samples were prepared in distilled water to make intragastric administration liquids having corresponding concentrations (i.e. 0.0175 g/ml, 0.0350 g/ml, 0.1050 g/ml) for experimentation. The intragastric administration amount for mice is calculated based on a ratio of 0.1 ml/10 g BW. The test groups each received one of the three doses of the intragastric administration liquids made from the composite powder for the oral liquid of TCM composition I every day, while the blank control group and the model control group received an equal volume of distilled water by intragastric administration. The intragastric administrations were conducted once a day and continued for 30 days. All mice groups were fed with common feed and allowed free access to feed and water. After 30 days, blood were sampled for determination of the activities of superoxide dismutase (SOD) and glutathione peroxidase (GSH-Px) and the content of malondialdehyde (MDA) in serum. Thereafter, except the blank control group, the other groups of mice were all irradiated once with 6Gy$^{60}$Co γ ray over the entire body. Four days after irradiation, the mice of all groups were sacrificed, and liver tissues were taken out for determination of the activities of superoxide dismutase (SOD) and glutathione peroxidase (GSH-Px) and the content of malondialdehyde (MDA).

1.3.3 Examined Indicators

The activities of SOD and GSH-Px and the MDA content in both serum and liver tissues were measured by strictly following the instructions for the kit provided by Nanjing Jiancheng Bioengineering Institute.

1.3.4 Statistic Methods

The experimental data are expressed as $\bar{x} \pm s$. One-way analysis of variance was employed to compare the activities of SOD and GSH-Px and the MDA content in serum before irradiation between the dosed test groups and the blank control group for difference, and to compare the activities of SOD and GSH-Px and the MDA content in liver tissues after irradiation between the dosed test groups and the model control group for difference. $P<0.05$ indicates the difference is significant.

2. Results 2.1 Body Weight Gain of Animals Compared to the blank control group, the mice groups that received various doses of the composite powder for oral liquid of TCM composition I showed no significant difference in body weight. See Table 1 below.

TABLE 1

The effect of the composite powder for oral liquid of TCM composition I on the body weight gain of the mice (g, $\bar{x} \pm s$)

| Group Name | Dose (g/kgbw) | Number of Animals | Initial Body Weight | Final Body Weight |
| --- | --- | --- | --- | --- |
| Blank control group | 0.000 | 10 | 18.63 ± 1.67 | 31.75 ± 3.20 |
| Model control group | 0.000 | 10 | 18.52 ± 1.45 | 31.66 ± 3.43 |
| Low-dose group | 0.175 | 10 | 18.51 ± 1.36 | 32.19 ± 2.14 |
| Medium-dose group | 0.350 | 10 | 18.80 ± 1.40 | 30.44 ± 2.46 |
| High-dose group | 1.050 | 10 | 18.43 ± 1.51 | 29.20 ± 2.78 |

2.2 Effect of the Composite Powder for Oral Liquid of TCM Composition I on the Serum Levels of GSH-Px, SOD, and MDA of the Mice Compared to the blank control group, the mice groups that received various doses showed no significant difference in serum GSH-Px activity. The mice groups that received the low, medium, and high doses showed a serum SOD activity significantly higher than that of the blank control group ($P<0.05$). The mice groups that received the medium and high doses showed a serum MDA content significantly lower than that of the blank control group ($P<0.05$). See Table 2 below.

TABLE 2

The effect of the composite powder for oral liquid of TCM composition I on the serum levels of GSH-Px, SOD, and MDA of the mice ($\bar{x} \pm s$)

| Group Name | Dose (g/kg bw) | Number of Animals | GSH-Px (EU) | SOD (U/ml) | MDA (nmol/ml) |
| --- | --- | --- | --- | --- | --- |
| Blank control group | 0.000 | 10 | 707.31 ± 295.12 | 130.15 ± 8.24 | 11.54 ± 1.20 |
| Low-dose group | 0.175 | 10 | 816.35 ± 172.10 | 154.91 ± 8.23* | 10.33 ± 1.34 |
| Medium-dose group | 0.350 | 10 | 847.12 ± 183.03 | 142.60 ± 9.58* | 9.50 ± 1.55* |
| High-dose group | 1.050 | 10 | 822.50 ± 145.66 | 141.69 ± 12.70* | 9.22 ± 1.91* |

*indicates significant difference from the blank control group ($P < 0.05$)

2.3 Effect of the Composite Powder for Oral Liquid of TCM Composition I on the Liver Levels of GSH-Px, SOD, and MDA of the Irradiated Mice The mice of the model control group showed liver activities of GSH-Px and SOD significantly lower than those of the blank control group, and showed a liver MDA content significantly higher than that of the blank control group, indicating successful establishment of an irradiation model. The mice groups that received the low, medium, and high doses of the composite powder for oral liquid of TCM composition I all showed liver activities of GSH-Px and SOD significantly higher than those of the model control group (P<0.05). The mice groups that received the medium and high doses both showed a liver MDA content significantly lower than that of the model control group (P<0.05). See Table 3 below.

TABLE 3

The effect of the composite powder for oral liquid of TCM composition I on the liver levels of GSH-Px, SOD, and MDA of the irradiated mice ($\bar{x} \pm s$)

| Group Name | Dose (g/kgbw) | Number of Animals | GSH-Px (EU/mgprot) | SOD (U/mgprot) | MDA (nmol/mgprot) |
| --- | --- | --- | --- | --- | --- |
| Blank control group | 0.000 | 10 | 864.60 ± 68.03* | 140.63 ± 18.52* | 0.82 ± 0.18* |
| Model control group | 0.000 | 10 | 442.75 ± 148.35 | 103.76 ± 11.05 | 1.37 ± 0.15 |
| Low-dose group | 0.175 | 10 | 620.60 ± 176.16* | 127.66 ± 19.17* | 1.24 ± 0.22 |
| Medium-dose group | 0.350 | 10 | 663.32 ± 194.07* | 123.89 ± 15.47* | 1.17 ± 0.17* |
| High-dose group | 1.050 | 10 | 708.30 ± 231.69 | 127.38 ± 14.19* | 1.15 ± 0.17* |

*indicates significant difference from the model control group (P < 0.05)

3. Conclusion

The daily intake dose of the composite powder for oral liquid of TCM composition I recommended for human (i.e., 2.10 g/60 kg BW) was scaled up by 5, 10, and 30 times to set up a low-dose group, a medium-dose group, and a high-dose group, respectively, corresponding to the doses of 0.175 g, 0.350 g, and 1.050 g per kg BW. A blank control group and a model control group were further set up. CL healthy male ICR mice were continuously administered intragastrically with the test samples, and after 30 days related indicators were measured. P<0.05 indicates the experimental results show significant difference. The animal experiments demonstrated that the mice groups that received the low, medium, and high doses of the composite powder for oral liquid of TCM composition I are all able to increase their serum SOD activity; the mice groups that received the medium and high doses are both able to lower their serum MDA content; the mice groups that received the low, medium, and high doses of the composite powder for oral liquid of TCM composition I all showed liver activities of GSH-Px and SOD significantly higher than those of the model control group which had been irradiated once with 6Gy$^{60}$Co γ ray over the entire body; and the mice groups that received the medium and high doses both showed a liver MDA content significantly lower than that of the model control group. According to the standards for defining a function of resisting oxidation provided in the Technical Standards for Testing and Assessment of Health Food (2003) issued by the Ministry of Health of the People's Republic of China, the composite powder for oral liquid of TCM composition I is believed to have a function of resisting oxidation. (VI). The Following Set of Animal Experiments Demonstrated that the Composite Powder for Oral Liquid of TCM Composition II (Radix Panacis Quinquefolii, *Ganoderma*, Fermented *Cordyceps sinensis* Powder, and Flos Rosae Rugosae) According to the Present Invention Showed the Effect of Resisting Oxidation in Human without Causing any Toxic or Adverse Effects. The Animal Experiments are Reported and Described Below.

1. Materials and Methods 1.1 Sources and Processing of Samples

The test medicine is TCM composition II (Radix Panacis Quinquefolii, *Ganoderma*, fermented *Cordyceps sinensis* powder, and Flos Rosae Rugosae) in a form of composite powder for oral liquid, which was provided by Jiangzhong Pharmaceutical Co. Ltd. This sample is present as brown solid powder and to be prepared in distilled water to have a desired concentration before use. 1 g of this dry composite powder is equivalent to 12.56 g total crude drugs.

TCM composition I (Radix Panacis Quinquefolii, *Ganoderma*, and fermented *Cordyceps sinensis* powder) was provided by Jiangzhong Pharmaceutical Co. Ltd. as composite powder. This sample is present as brown solid powder and to be prepared in distilled water to have a desired concentration before use. 1 g of this dry composite powder is equivalent to 11.41 g total crude drugs.

1.2 Laboratory Animals and Experimental Environments

CL healthy male Kunming mice, each weighing 18 to 22 g, were provided by the Laboratory Animal Center, Jiangxi University of Traditional Chinese Medicine (Certification Number: SCXK (Jiangxi)-2006-0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods 1.3.1 Animal Grouping 60 mice were divided randomly into 6 groups based on their body weights. A blank control group, a model control group, a group on TCM composition I, and test groups on a low dose, a medium dose, and a high dose of the composite powder for oral liquid of TCM composition II, were set up, with 10 animals in each group.

1.3.2 Dosage Design

The recommended daily intake dose per person of the composite powder for oral liquid of TCM composition II is 200 ml/60 kg BW. Every 1000 ml oral liquid of TCM composition II is formulated with 120 g total crude drugs, and 1 g dry composite powder is equivalent to 12.56 g total crude drugs. Therefore, the recommended daily intake dose per person of the composite powder for oral liquid of TCM composition II can be calculated as 24 g crude drugs/60 kg BW. Based on this dose, daily intake doses for mice are calculated as 2.0 g crude drugs/kg BW for the low-dose group, 4.0 g crude drugs/kg BW for the medium-dose group, and 12 g crude drugs/kg BW for the high-dose group, equivalent to 5, 10, and 30 times the daily intake dose for human, respectively. The samples were prepared in distilled water to make intragastric administration liquids having corresponding concentrations (i.e. 0.0159 g dry powder/ml, 0.0318 g dry powder/ml, 0.0995 g dry powder/ml) for experimentation. The intragastric administration amount for mice was calculated based on a ratio of 0.1 ml/10 g BW.

The recommended daily intake dose per person of the composite powder of TCM composition I is 200 ml/60 kg BW. Every 1000 ml oral liquid of TCM composition II is formulated with 120 g total crude drugs, and 1 g dry composite powder of TCM composition I is equivalent to 11.41 g total crude drugs. A medium dose, i.e., 4.0 g crude drugs/kg BW (equivalent to 10 times the daily intake dose for human), was given to the group on TCM composition I. The sample was prepared in distilled water to make a 0.0350 g dry powder/ml intragastric administration liquid for experimentation. The intragastric administration amount was calculated based on a ratio of 0.1 ml/10 g BW. The blank control group and the model control group were given an equal volume of distilled water by intragastric administration. The intragastric administrations were conducted once a day and continued for 30 days. All mice groups were fed with common feed and allowed free access to feed and water. After 30 days, blood were sampled for determination of the activities of superoxide dismutase (SOD) and glutathione peroxidase (GSH-Px) and the content of malondialdehyde (MDA) in serum. Thereafter, except the blank control group, the other groups of mice were all irradiated once with 6Gy$^{60}$Co γ ray over the entire body. Four days after irradiation, the mice of all groups were sacrificed, and liver tissues were taken out for determination of the activities of superoxide dismutase (SOD) and glutathione peroxidase (GSH-Px) and the content of malondialdehyde (MDA).

1.3.3 Examined Indicators

The activities of SOD and GSH-Px and the MDA content in both serum and liver tissues were measured by strictly following the instructions for the kit provided by Nanjing Jiancheng Bioengineering Institute.

1.3.4 Statistic Methods

The experimental data are expressed as $\bar{x}\pm s$. One-way analysis of variance was employed to compare the activities of SOD and GSH-Px and the MDA content in serum before irradiation between the dosed test groups and the blank control group for difference, and to compare the activities of SOD and GSH-Px and the MDA content in liver tissues after irradiation between the dosed test groups on one hand and the model control group and the group on the original formulation on the other for difference. $P<0.05$ indicates the difference is significant.

2. Results 2.1 Body Weight Gain of Animals

Compared to the blank control group and the group on TMC composition I, the mice groups that received various doses of the composite powder for oral liquid of TCM composition II showed no significant difference in body weight. See Table 1 below.

TABLE 1

The effect of the composite powder for oral liquid of TCM composition II on the body weight gain of the mice (g, $\bar{x}\pm s$)

| Group Name | Dose (g crude drugs/kgbw) | Number of Animals | Initial Body Weight | Final Body Weight |
| --- | --- | --- | --- | --- |
| Blank control group | 0.0 | 10 | 19.70 ± 1.34 | 32.90 ± 2.13 |
| Model control group | 0.0 | 10 | 20.20 ± 1.32 | 32.80 ± 2.30 |
| Group on TCM composition I | 4.0 | 10 | 19.70 ± 1.36 | 33.00 ± 2.54 |
| Low-dose group on test medicine | 2.0 | 10 | 20.00 ± 1.49 | 33.50 ± 2.22 |
| Medium-dose group on test medicine | 4.0 | 10 | 19.80 ± 1.54 | 33.90 ± 2.38 |
| High-dose group on test medicine | 12.0 | 10 | 19.88 ± 1.48 | 33.60 ± 2.73 |

2.2 Effect of the Composite Powder for Oral Liquid of TCM Composition II on the Serum Levels of GSH-Px, SOD, and MDA of the Mice Compared to the blank control group, the mice groups that received various doses of the composite powder for oral liquid of TCM composition II and the mice group that received TMC composition I showed significantly increased serum activities of GSH-Px and SOD ($P<0.05$, $P<0.01$) and meanwhile a significantly decreased serum MDA content ($P<0.05$, $P<0.01$). Compared to the group that received TMC composition I, the mice groups that received the medium and high doses of the composite powder for oral liquid of TCM composition II showed significantly increased serum activities of both GSH-Px and SOD ($P<0.05$, $P<0.01$) and meanwhile a significantly decreased serum MDA content ($P<0.05$). See Table 2 below.

TABLE 2

The effect of the composite powder for oral liquid of TCM composition II on the serum levels of GSH-Px, SOD, and MDA of the mice ($\bar{x}\pm s$)

| Group Name | Dose (g/kgbw) | Number of Animals | GSH-Px (EU) | SOD (U/ml) | MDA (nmol/ml) |
| --- | --- | --- | --- | --- | --- |
| Blank control group | 0.0 | 10 | 612.00 ± 145.54 | 111.00 ± 11.76 | 10.37 ± 1.38 |
| Model control group | 0.0 | 10 | 613.90 ± 105.36 | 110.10 ± 15.56 | 10.58 ± 1.16 |
| Group on TCM composition I | 4.0 | 10 | 757.20 ± 143.31* | 125.60 ± 11.56* | 9.42 ± 1.04* |
| Low-dose group on test medicine | 2.0 | 10 | 766.60 ± 123.12** | 130.10 ± 11.78** | 9.17 ± 1.18** |

TABLE 2-continued

The effect of the composite powder for oral liquid of TCM composition II
on the serum levels of GSH-Px, SOD, and MDA of the mice ($\bar{x} \pm s$)

| Group Name | Dose (g/kgbw) | Number of Animals | GSH-Px (EU) | SOD (U/ml) | MDA (nmol/ml) |
|---|---|---|---|---|---|
| Medium-dose group on test medicine | 4.0 | 10 | 899.10 ± 119.27**▲ | 137.90 ± 13.63**▲ | 8.37 ± 0.83**▲ |
| High-dose group on test medicine | 12.0 | 10 | 952.30 ± 119.98**▲▲ | 144.00 ± 12.99**▲▲ | 8.09 ± 0.79**▲▲ |

*$P < 0.05$ and
**$P < 0.01$ compared to the model control group;
▲$P < 0.05$ and
▲▲$P < 0.05$ compared to the group on TCM composition I.

2.3 Effect of the Composite Powder for Oral Liquid of TCM Composition II on the Liver Levels of GSH-Px, SOD, and MDA of the Irradiated Mice Compared to the blank control group, the mice of the model control group showed significantly decreased liver activities of GSH-Px and SOD ($P<0.01$) and a significantly increased liver MDA content ($P<0.01$), indicating successful establishment of an irradiation model. Compared to the model control group, the mice groups that received the low, medium, and high doses of the composite powder for oral liquid of TCM composition II and the mice group that received TMC composition I all showed significantly increased liver activities of GSH-Px and SOD ($P<0.01$) and meanwhile a significantly decreased liver MDA content ($P<0.01$). Compared to the group that received TMC composition I, the mice groups that received the medium and high doses of the composite powder for oral liquid of TCM composition II showed significantly increased liver activities of GSH-Px and SOD ($P<0.05$, $P<0.01$) and meanwhile a significantly decreased liver MDA content ($P<0.05$, $P<0.01$). See Table 3 below.

times to set up a low-dose group, a medium-dose group, and a high-dose group, respectively, corresponding to the doses of 2.0 g, 4.0 g, and 12.0 g crude drugs per kg BW. A blank control group, a model control group, and a group on TCM composition I (12.0 g crude drugs per kg BW) were further set up. CL healthy male Kunming mice were continuously administered intragastrically with the test samples, and after 30 days related indicators were measured. $P<0.05$ and $P<0.01$ indicate the experimental results show significant difference and highly significant difference, respectively. The animal experiments demonstrated that the mice groups that received the low, medium, and high doses of the composite powder for oral liquid of TCM composition II are all able to increase their serum GSH-Px and SOD activities and decrease their serum MDA content; the mice groups that received the low, medium, and high doses of the composite powder for oral liquid of TCM composition II all showed liver activities of GSH-Px and SOD significantly higher than those of the model control group which had been irradiated once with 6Gy$^{60}$Co γ ray over the entire body, and all showed a liver MDA content significantly lower than that of the model con-

TABLE 3

The effect of the composite powder for oral liquid of TCM composition II on the
liver levels of GSH-Px, SOD, and MDA of the irradiated mice ($\bar{x} \pm s$)

| Group Name | Dose (g/kgbw) | Number of Animals | GSH-Px (EU/mgprot) | SOD (U/mgprot) | MDA (nmol/mgprot) |
|---|---|---|---|---|---|
| Blank control group | 0.0 | 10 | 863.60 ± 102.09** | 148.40 ± 14.71** | 0.85 ± 0.12** |
| Model control group | 0.0 | 10 | 464.20 ± 101.98 | 103.10 ± 13.30 | 1.38 ± 0.11 |
| Group on TCM composition I | 4.0 | 10 | 617.00 ± 100.17** | 126.70 ± 15.95** | 1.17 ± 0.13** |
| Low-dose group on test medicine | 2.0 | 10 | 629.60 ± 111.15** | 131.80 ± 16.65** | 1.16 ± 0.20** |
| Medium-dose group on test medicine | 4.0 | 10 | 734.10 ± 121.64**▲ | 144.10 ± 17.03**▲ | 0.95 ± 0.14**▲▲ |
| High-dose group on test medicine | 12.0 | 10 | 815.70 ± 90.72**▲▲ | 150.60 ± 17.24**▲▲ | 0.86 ± 0.14**▲▲ |

*$P < 0.05$ and
**$P < 0.01$ compared to the model control group;
▲$P < 0.05$ and
▲▲$P < 0.05$ compared to the group on TCM composition I.

3. Conclusion

The daily intake dose of the composite powder for oral liquid of TCM composition II recommended for human (i.e., 24.0 g crude drugs/60 kg BW) was scaled up by 5, 10, and 30 trol group; and the mice groups that received the medium and high doses of the composite powder for oral liquid of TCM composition II both showed liver activities of GSH-Px and SOD significantly higher than those of the comparative group that received TCM composition I, and a liver MDA content significantly lower than that of the comparative group that received TCM composition I. According to the standards for defining a function of resisting oxidation provided in the *Technical Standards for Testing and Assessment of Health Food* (2003) issued by the Ministry of Health of the People's Republic of China, the composite powder for oral liquid of TCM composition II is believed to have a function of resisting oxidation more effectively than TCM composition I.

(VII) The Following Set of Animal Experiments Demonstrated that TCM Composition I (Radix Panacis Quinquefolii, *Ganoderma*, and Fermented *Cordyceps Sinensis* Powder) According to the Present Invention Showed the Effect Of Enhancing Anoxia Endurance of Mice without Causing any Toxic or Adverse Effects. The Animal Experiments are Reported and Described Below.

1. Materials and Methods 1.1 Samples

TCM composition I (Radix Panacis Quinquefolii, *Ganoderma*, and fermented *Cordyceps sinensis* powder) according to the present invention for oral liquid, provided by Jiangzhong Pharmaceutical Co. Ltd., is present as pale brown or brown solid powder and can be preserved at room temperature for a long time until use. The formulation of TCM composition I according to the present invention for oral liquid provided by the company is 15 g Radix Panacis Quinquefolii, 20 g *Ganoderma*, 10 g fermented *Cordyceps sinensis* powder, and 75 g auxiliary agents (120 g in total). The recommended dose of the oral liquid of TCM composition I according to the present invention is 24 g/day for adults (whose body weight is counted as 60 kg), equivalent to 0.4 g/day/kg BW, wherein Radix Panacis Quinquefolii accounts for 12.5%, *Ganoderma* 16.7%, and fermented *Cordyceps sinensis* powder 8.3%.

1.2 Laboratory Animals 120 healthy male Balb/c mice, each aged 6-8 weeks and weighing 18-22 g, were provided by the Laboratory Animal Center, Chinese Academy of Medical Science (Certification Number: SCXK (Beijing) 2005-0013). They underwent experiments in three batches, and the mice in each batch were divided randomly into 4 groups (10 animals in each group). Experimental batch 1 was subjected to the anoxia endurance experiment under normal pressure, Experimental batch 2 to the sodium nitrite poisoning survival experiment, and Experimental batch 3 to the acute cerebral ischemic anoxia experiment. The laboratory animals were fed in a grade-II animal room in the Laboratory Animal Center, Peking University Health Science Center.

1.3 Grouping

For the experiments, test groups on a low dose, a medium dose, and a high dose of the oral liquid of TCM composition I according to the present invention, which correspond respectively to 3.3, 10, and 30 times the dose of the oral liquid of TCM composition I according to the present invention recommended for human (i.e., 4.5 g/kg/day, 1.5 g/kg/day, 0.5 g/kg/day), and a blank control group, were set up. The test samples were prepared in water (sterilized) and given orally once a day. The body weights were measured weekly, according to which the intragastric administration amounts were adjusted. After continuous intragastric administrations for 45 days, various immunity indicators were measured. The intragastric administration volume for mice was 0.1 ml/10 g mice BW. A blank control group (0 g/kg/day) was set up, for which test samples was replaced with water (sterilized) and the daily intragastric administration volume was the same as in the test groups. During the experiments the animals were allowed free access to food and water.

1.4 Main Apparatus and Reagents 250 ml flasks with a ground glass joint; a stopwatch; 1 ml syringes; scissors; Vaseline, soda lime, sodium nitrite.

1.5 Experimental Methods 1.5.1 Anoxia Endurance Experiment Under Normal Pressure One hour after the last intragastric administration of the 45-day intragastric administrations, all groups of mice were placed into the 250 ml flasks having a ground glass joint and containing 5 g soda lime (one animal in each flask), and counting of time was started immediately after the opening of each flask was sealed with Vaseline and a stopper to be air tight. The time when the mice died of anoxia, as indicated by respiratory arrest, was recorded. If the test groups show a survival time longer than that of the control group and the difference therebetween is statistically significant, the experiment result is then determined as positive.

1.5.2 Sodium Nitrite Poisoning Survival Experiment

One hour after the last intragastric administration, all groups of mice were intraperitoneally injected with sodium nitrite at a dose of 200-240 mg/kg BW (the injection amount was 0.1 ml/10 g). Time was counted immediately after the injection and survival time of mice was recorded. If the test groups show a survival time longer than that of the control group and the difference therebetween is statistically significant, the experiment result is then determined as positive.

1.5.3 Acute Cerebral Ischemic Anoxia Experiment

One hour after the last intragastric administration, each of the mice in all groups was decapitated from the cervical part under light anesthesia with diethyl ether, and time was counted immediately thereafter to record the duration from the decapitation to the cessation of breath through the mouth of the mouse. If the test groups show a breath time longer than that of the control group and the difference therebetween is statistically significant, the experiment result is then determined as positive.

1.6 Statistic Methods

All results are expressed as Average value±Standard deviation. One-way analysis of variance was performed using the program SPSS 16.0 to compare the test groups and the control group for difference. However, homogeneity test of variance was first conducted using the variance analysis program, in which the F value was calculated for homogeneity of variance. If $F<F_{0.005}$, then it is concluded that there is no significant difference in average value between the groups; and if $F \geq F_{0.005}$ and $P<0.05$, statistics were made by comparing the average value of each of the multiple test groups with the average value of the control group. The data in non-normal distribution or with heterogeneous variance were subjected to appropriate variable transformation, and the transformed data that fulfill the requirement for normal distribution or homogeneous variance were used in the statistics. If normal distribution or homogeneous variance is still not achieved after the variable transformation, the statistics are made by using the rank sum test.

1.7 Standards for Evaluating Results

The *Technical Standards for Testing and Assessment of Health Food* (2003) provides that if any two experiments of the anoxia endurance experiment under normal pressure, the sodium nitrite poisoning survival experiment, and the acute cerebral ischemic anoxia experiment show positive results, the tested samples are deemed as having an effect of enhancing anoxia endurance.

2. Results 2.1 Effect on the Anoxia Endurance Time Under Normal Pressure of the Mice in the Groups that Received the Low, Medium, and High Doses of the Oral Liquid of TCM Composition I According to the Present Invention and in the Control Group

TABLE 1

The effect of the oral liquid of TCM composition I according to the present invention on the anoxia endurance time under normal pressure of mice (x ± SD)

| Group Name | Number of Animals | Anoxia Endurance Time Under Normal Pressure(s) |
|---|---|---|
| Control | 10 | 2263.20 ± 218.29 |
| Low dose | 10 | 2925.14 ± 390.46* |
| Medium dose | 10 | 2513.11 ± 341.34 |
| High dose | 10 | 3054.17 ± 485.74* |

*indicates significant difference from the control group ($P < 0.05$)

According to Table 1, after the 45-day administration of the test samples to mice through the mouth, the dosed test groups that received the low and high doses of the oral liquid of TCM composition I according to the present invention can significantly extend the anoxia endurance time under normal pressure of mice when compared to the blank control group ($P<0.05$).

2.2 Effect on the Survival Time of the Mice after Sodium Nitrite Poisoning in the Groups That Received the Low, Medium, and High Doses of the Oral Liquid of TCM Composition I According to the Present Invention and in the Control Group

TABLE 2

The effect of the test samples on the survival time of mice after sodium nitrite poisoning (x ± SD)

| Group Name | Number of Animals | Survival Time after Sodium Nitrite Poisoning(s) |
|---|---|---|
| Control | 10 | 993.79 ± 156.23 |
| Low dose | 10 | 1115.94 ± 183.52 |
| Medium dose | 10 | 1069.39 ± 282.58 |
| High dose | 10 | 1279.33 ± 349.79* |

*indicates significant difference from the control group ($P < 0.05$)

According to Table 2, after the 45-day administration of the test samples to mice through the mouth, the dosed test groups that received the high dose of the oral liquid of TCM composition I according to the present invention significantly extended the survival time of mice after sodium nitrite poisoning when compared to the blank control group ($P<0.05$), i.e., the oral liquid of TCM composition I according to the present invention at the dose of 4.5 g/kg/day can enhance the ability of mice to survive sodium nitrite poisoning.

2.3 Effect on the Survival Time of the Mice Under Acute Cerebral Ischemic Anoxia in the Groups that Received the Low, Medium, and High Doses of the Oral Liquid of TCM Composition I According to the Present Invention and in the Control Group

TABLE 3

The effect of the oral liquid of TCM composition I according to the present invention on the survival time of mice under cerebral ischemic anoxia (x ± SD)

| Group Name | Number of Animals | Survival Time of Mice under Cerebral Ischemic Anoxia |
|---|---|---|
| Control | 10 | 19.42 ± 3.33 |
| Low dose | 10 | 21.19 ± 1.63 |
| Medium dose | 10 | 22.10 ± 3.07 |
| High dose | 10 | 22.31 ± 1.98* |

*indicates significant difference from the blank group ($P < 0.05$)

According to Table 3, after the 45-day administration of the various doses of test samples to mice through the mouth, the dosed test groups that received the high dose can significantly extend the survival time of mice under acute cerebral ischemic anoxia when compared to the control group ($P<0.05$), i.e., the oral liquid of TCM composition I according to the present invention at the dose of 4.5 g/kg/day can extend the acute anoxia endurance time of mice.

3. Summary

After the 45-day administration of the various doses of the oral liquid of TCM composition I according to the present invention to mice through the mouth, compared to the blank control group, the test group on the dose of 4.5 g/kg/day significantly extended the anoxia endurance time under normal pressure of mice, the survival time of mice after sodium nitrite poisoning, and the survival time of mice under cerebral ischemic anoxia; and the test group on the dose of 0.5 g/kg BW significantly extended the anoxia endurance time under normal pressure of mice.

According to the standards for defining a function of relieving physical fatigue provided in the *Technical Standards for Testing and Assessment of Health Food* (2003) issued by the Ministry of Health of the People's Republic of China, in the above efficacy experiment, the oral liquid of TCM composition I according to the present invention is believed to have a health function of enhancing anoxia endurance.

(VIII) The Following Set of Animal Experiments Demonstrated that the Composite Powder of TCM Composition II (Radix Panacis Quinquefolii, *Ganoderma*, Fermented *Cordyceps sinensis* Powder, and Flos Rosae Rugosae) According to the Present Invention Showed the Effect of Enhancing Anoxia Endurance of Mice Without Causing any Toxic or Adverse Effects. The Animal Experiments are Reported and Described Below.

1. Materials and Methods 1.1 Samples

The test medicine is TCM composition II (Radix Panacis Quinquefolii, *Ganoderma*, fermented *Cordyceps sinensis* powder, and Flos Rosae Rugosae) in a form of composite powder, which was provided by Jiangzhong Pharmaceutical Co. Ltd. This sample is present as brown solid powder and to be prepared in distilled water to have a desired concentration before use. 1 g of this dry composite powder is equivalent to 12.56 g total crude drugs.

TCM composition I (Radix Panacis Quinquefolii, *Ganoderma*, and fermented *Cordyceps sinensis* powder) was provided by Jiangzhong Pharmaceutical Co. Ltd. as composite powder. This sample is present as brown solid powder and to be prepared in distilled water to have a desired concentration before use. 1 g of this dry composite powder is equivalent to 11.41 g total crude drugs.

1.2 Laboratory Animals

CL healthy male Kunming mice, each weighing 18 to 22 g, were provided by the Laboratory Animal Center, Jiangxi University of Traditional Chinese Medicine (Certification Number: SCXK (Jiangxi)-2006-0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods 1.3.1 Animal Grouping

The mice (150 animals in total) underwent experiments in three batches, and the mice in each batch were divided randomly into 5 groups (10 animals in each group).

Experimental batch 1 was subjected to the anoxia endurance experiment under normal pressure, Experimental batch 2 to the sodium nitrite poisoning survival experiment, and Experimental batch 3 to the acute cerebral ischemic anoxia experiment.

1.3.2 Dosage Design

The recommended daily intake dose per person of the composite powder of TCM composition II (Radix Panacis Quinquefolii, Ganoderma, fermented Cordyceps sinensis powder, and Flos Rosae Rugosae) is 200 ml/60 kg BW. Every 1000 ml oral liquid of TCM composition II is formulated with 120 g total crude drugs, and 1 g dry composite powder is equivalent to 12.56 g total crude drugs. Therefore, the recommended daily intake dose per person of the composite powder of TCM composition II (Radix Panacis Quinquefolii, Ganoderma, fermented Cordyceps sinensis powder, and Flos Rosae Rugosae) can be calculated as 24 g crude drugs/60 kg BW. Based on this dose, daily intake doses for mice are calculated as 2.0 g crude drugs/kg BW for the low-dose group, 4.0 g crude drugs/kg BW for the medium-dose group, and 12 g crude drugs/kg BW for the high-dose group, equivalent to 5, 10, and 30 times the daily intake dose for human, respectively. The samples were prepared in distilled water to make intragastric administration liquids having corresponding concentrations (i.e. 0.0159 g dry powder/ml, 0.0318 g dry powder/ml, 0.0995 g dry powder/ml) for experimentation. The intragastric administration amount for mice was calculated based on a ratio of 0.1 ml/10 g BW.

The recommended daily intake dose per person of the composite powder of TCM composition I is 200 ml/60 kg BW. Every 1000 ml oral liquid of TCM composition I is formulated with 120 g total crude drugs, and 1 g dry composite powder of TCM composition I is equivalent to 11.41 g total crude drugs. The composite powder of TCM composition I was given at the medium dose, i.e. 4.0 g crude drugs/kg BW (equivalent to 10 times the daily intake dose for human). The sample was prepared in distilled water to make a 0.0350 g dry powder/ml intragastric administration liquid for experimentation. The intragastric administration amount was calculated based on a ratio of 0.1 ml/10 g BW. The administrations were conducted once a day via the mouth. The body weights were measured weekly, according to which the intragastric administration amounts were adjusted. After continuous intragastric administrations for 45 days, various indicators were measured. A blank control group was also set up, and was intragastrically administered with distilled water in a daily volume equal to that for the test groups. During the experiments the animals were allowed free access to food and water.

1.3.3 Anoxia Endurance Experiment Under Normal Pressure

One hour after the last intragastric administration of the 45-day intragastric administrations, all groups of mice were placed into the 250 ml flasks having a ground glass joint and containing 5 g soda lime (one animal in each flask), and counting of time was started immediately after the opening of each flask was sealed with Vaseline and a stopper to be air tight. The time when the mice died of anoxia, as indicated by respiratory arrest, was recorded.

1.3.4 Sodium Nitrite Poisoning Survival Experiment

One hour after the last intragastric administration, all groups of mice were intraperitoneally injected with sodium nitrite at a dose of 240 mg/kg BW (the injection amount was 0.1 ml/10 g). Time was counted immediately after the injection and survival time of mice was recorded.

1.3.5 Acute Cerebral Ischemic Anoxia Experiment

One hour after the last intragastric administration, each of the mice in all groups was decapitated from the cervical part under light anesthesia with diethyl ether, and time was counted immediately thereafter to record the duration from the decapitation to the cessation of breath through the mouth of the mouse.

1.4 Main Apparatus and Reagents 250 ml flasks with a ground glass joint; a stopwatch; 1 ml syringes; scissors; Vaseline, soda lime, sodium nitrite.

1.5 Statistic Methods

All results are expressed as Average value±Standard deviation. One-way analysis of variance was performed using the program SPSS 15.0 to compare the test groups and the control group for difference. However, homogeneity test of variance was first conducted using the variance analysis program, in which the F value was calculated for homogeneity of variance. If $F<F_{0.005}$, then it is concluded that there is no significant difference in average value between the groups; and if $F \geq F_{0.005}$ and $P<0.05$, statistics were made by comparing the average value of each of the multiple test groups with the average value of the control group. The data in non-normal distribution or with heterogeneous variance were subjected to appropriate variable transformation, and the transformed data that fulfill the requirement for normal distribution or homogeneous variance were used in the statistics. If normal distribution or homogeneous variance is still not achieved after the variable transformation, the statistics are made by using the rank sum test.

1.6 Standards for Evaluating Results

If any two experiments of the anoxia endurance experiment under normal pressure, the sodium nitrite poisoning survival experiment, and the acute cerebral ischemic anoxia experiment show positive results, the tested samples are deemed as having an effect of enhancing anoxia endurance.

2. Results 2.1 Effect of the Oral Liquid of TCM Composition II (Radix Panacis Quinquefolii, Ganoderma, Fermented Cordyceps sinensis Powder, and Flos Rosae Rugosae) on the Anoxia Endurance Time Under Normal Pressure of the Mice The mice groups that received the low, medium, and high doses of the oral liquid of TCM composition II and the mice group that received TCM composition I showed an anoxia endurance time under normal pressure significantly longer than that of the blank control group ($P<0.05$, $P<0.01$). The mice groups that received the medium and high doses of the oral liquid of TCM composition II showed an anoxia endurance time under normal pressure significantly longer than that of the comparative group that received TCM composition I ($P<0.05$). See Table 1 below for the results.

TABLE 1

The effect of the oral liquid of TCM composition
II on the anoxia endurance time under normal pressure
of the mice ($\bar{X} \pm S$)

| Group Name | Dose (g crude drugs/kgbw) | Number of Animals | Anoxia Endurance Time Under Normal Pressure(s) |
|---|---|---|---|
| Blank control group | 0.0 | 10 | 2287.70 ± 203.579 |
| Group on TCM composition I | 4.0 | 10 | 2567.90 ± 191.127** |
| Low-dose group on test medicine | 2.0 | 10 | 2510.80 ± 226.28* |
| Medium-dose group on test medicine | 4.0 | 10 | 2820.40 ± 265.19**▲ |
| High-dose group on test medicine | 12.0 | 10 | 2937.70 ± 269.90**▲ |

*$P < 0.05$ and
**$P < 0.01$ compared to the blank control group;
▲$P < 0.05$ compared to the group on TCM composition I.

2.2 Effect of the Oral Liquid of TCM Composition II on the Survival Time of Mice after Sodium Nitrite Poisoning The mice groups that received the medium and high doses of the oral liquid of TCM composition II showed a survival time after sodium nitrite poisoning significantly longer than that of the blank control group ($P<0.01$). The mice groups that received the medium and high doses of the oral liquid of TCM composition II showed a survival time after sodium nitrite poisoning significantly longer than that of the comparative group that received TCM composition I ($P<0.05$). See Table 2 below for the results.

TABLE 2

The effect of the oral liquid of TCM composition II on the survival time
of the mice after sodium nitrite poisoning ($\bar{X} \pm S$)

| Group Name | Dose (g crude drugs/kgbw) | Number of Animals | Survival Time after Sodium Nitrite Poisoning(s) |
|---|---|---|---|
| Blank control group | 0.0 | 10 | 950.50 ± 125.98 |
| Group on TCM composition I | 4.0 | 10 | 1047.70 ± 152.28 |
| Low-dose group on test medicine | 2.0 | 10 | 982.00 ± 131.83 |
| Medium-dose group on test medicine | 4.0 | 10 | 1177.20 ± 150.04**▲ |
| High-dose group on test medicine | 12.0 | 10 | 1179.70 ± 139.79**▲ |

**$P < 0.01$ compared to the blank control group;
▲$P < 0.05$ compared to the group on TCM composition I.

2.3 Effect of the Oral Liquid of TCM Composition II on the Survival Time of Mice Under Acute Cerebral Ischemic Anoxia The mice groups that received the medium and high doses of the oral liquid of TCM composition II and the mice group that received TCM composition I all showed a survival time under cerebral ischemic anoxia significantly longer than that of the blank control group ($P<0.05$, $P<0.01$). The mice groups that received the medium and high doses of the oral liquid of TCM composition II both showed a survival time under cerebral ischemic anoxia significantly longer than that of the comparative group that received TCM composition I ($P<0.05$). See Table 3 below for the results.

TABLE 3

The effect of the oral liquid of TCM composition II on the survival time
of the mice under cerebral ischemic anoxia ($\bar{X} \pm S$)

| Group Name | Dose (g crude drugs/kgbw) | Number of Animals | Survival Time of Mice under Cerebral Ischemic Anoxia(s) |
|---|---|---|---|
| Blank control group | 0.0 | 10 | 19.05 ± 1.12 |
| Group on TCM composition I | 4.0 | 10 | 20.59 ± 1.63* |
| Low-dose group on test medicine | 2.0 | 10 | 20.07 ± 1.41 |
| Medium-dose group on test medicine | 4.0 | 10 | 22.16 ± 2.05**▲ |
| High-dose group on test medicine | 12.0 | 10 | 22.14 ± 1.98**▲ |

*$P < 0.05$ and
**$P < 0.01$ compared to the blank control group;
▲$P < 0.05$ compared to the group on TCM composition I.

3. Summary

The daily intake dose of the composite powder for oral liquid of TCM composition II recommended for human (i.e., 24 g crude drugs/60 kg BW) was scaled up by 5, 10, and 30 times to set up a low-dose group, a medium-dose group, and a high-dose group, respectively, corresponding to the doses of 2.0 g, 4.0 g, and 12.0 g crude drugs per kg BW. A blank control group and a comparative group on TCM composition I were further set up. CL healthy male mice were continuously administered intragastrically with the test samples, and after 45 days related indicators were measured. $P<0.05$ indicates the experimental results show significant difference. The animal experiments demonstrated that the mice groups that received the low, medium, and high doses of the composite powder for oral liquid of TCM composition II showed an anoxia endurance time under normal pressure significantly longer than that of the blank control group; the mice groups that received the medium and high doses of the composite powder for oral liquid of TCM composition II showed a survival time after sodium nitrite poisoning and a survival time under cerebral ischemic anoxia significantly longer than those of the blank control group; and the mice groups that received the medium and high doses of the composite powder for oral liquid of TCM composition II showed an anoxia endurance time under normal pressure, a survival time after sodium nitrite poisoning, and a survival time under cerebral ischemic anoxia significantly longer than those of the comparative group that received TCM composition I. The composite powder for oral liquid of TCM composition II is believed to have a health function of enhancing anoxia endurance more effectively than TCM composition I.

DETAILED DESCRIPTION OF THE INVENTION

Example 1

1. Materials and Methods
1.1 Sources of Samples

The test sample is TCM composition I (herein refers to Radix Panacis Quinquefolii, *Ganoderma*, and *Cordyceps*) provided by Jiangzhong Pharmaceutical Co. Ltd. as composite powder for oral liquid, and 1 g of this dry composite powder is equivalent to 11.41 g total crude drugs. The recommended daily intake dose per person thereof is 24 g crude drugs/60 kg BW.

The comparative sample is TCM composition II (herein refers to Radix Panacis Quinquefolii, *Ganoderma*, and fermented *Cordyceps sinensis* powder) provided by Jiangzhong Pharmaceutical Co. Ltd. as composite powder. 1 g of this dry composite powder is equivalent to 10.97 g total crude drugs. The recommended daily intake dose per person thereof is 24 g crude drugs/60 kg BW.

1.2 Laboratory Animals and Experimental Environments

CL healthy male Kunming mice, each weighing 18 to 22 g, were provided by the Laboratory Animal Center, Jiangxi University of Traditional Chinese Medicine (Certification Number: SCXK (Jiangxi)-2006-0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods 1.3.1 Animal Grouping 200 male Kunming mice were divided randomly into 4 groups (50 animals in each group) based on their body weights. Each animal group was further divided randomly into the following subgroups, i.e., a blank control group, test groups on a low dose, a medium dose, and a high dose of the oral liquid of TCM composition I, and a group on the composite powder of TCM composition II (10 animals in each subgroup).

1.3.2 Dosage Design

The recommended daily intake dose per person of the test medicine, i.e. the composite powder for oral liquid of TCM composition I, is 200 ml/60 kg BW. Every 1000 ml oral liquid of TCM composition I is formulated with 120 g total crude drugs, and thus the recommended daily intake dose per person is 24 g crude drugs/60 kg BW. Based on this dose, daily intake doses for mice are calculated as 2.0 g crude drugs/kg BW for the low-dose group, 4.0 g crude drugs/kg BW for the medium-dose group, and 12 g crude drugs/kg BW for the high-dose group, equivalent to 5, 10, and 30 times the daily intake dose for human, respectively. The samples were prepared in distilled water to make intragastric administration liquids having corresponding concentrations (i.e. 0.0175 g dry powder/ml, 0.0350 g dry powder/ml, 0.1050 g dry powder/ml) for experimentation. The intragastric administration amount for mice was calculated based on a ratio of 0.1 ml/10 g BW.

The recommended daily intake dose per person of TCM composition II is 24 g crude drugs/60 kg BW. Based on this dose, the dose for mice is calculated as 4.0 g crude drugs/kg BW (equivalent to 10 times the daily intake dose for human). The sample was prepared in distilled water to make a 0.0365 g dry powder/ml intragastric administration liquid for experimentation. The intragastric administration amount was calculated based on a ratio of 0.1 ml/10 g BW. The blank control group was given an equal volume of distilled water by intragastric administration. The intragastric administrations were conducted once a day and continued for 30 days. All mice groups were fed with common feed and allowed free access to feed and water. After 30 days, all subgroups of mice were subjected to a function test on relieving of physical fatigue.

1.3.3 Burdened Swimming Experiment 30 minutes after given the last test sample, the 10 mice of the first subgroup were each loaded a piece of lead weighing 5% of their body weight at the base of their tails. Then each burdened mouse was put into a swimming tank (with a depth≥30 cm, and water temperature of 25° C.±1.0° C.) to swim. The duration from the beginning of swimming to the death of the mouse was recorded as the burdened swimming time of the mouse.

1.3.4 Serum Urea Nitrogen Measurement 30 minutes after given the last test sample, the 10 mice of the second subgroup were allowed to swim without any burden in 30° C. water for 90 min. After a 60-minute rest, their eyeballs were taken out, and about 0.5 ml whole blood was collected and placed in a 4° C. fridge for about 3 h. When coagulated, the blood was centrifuged at 2000 rpm for 15 min, and the serum was isolated for urea nitrogen content determination. The serum urea nitrogen was measured in Olympus AU400 automated Chemistry Analyzer (Japan), using the reagents provided by Daiichi Pure Chemicals Co., Ltd., Japan.

1.3.5 Liver Glycogen Measurement 30 minutes after given the last test sample, the 10 mice of the third subgroup were sacrificed. The livers were taken out, rinsed with saline solution, and blotted with filter paper. 100 mg liver was precisely weighed out, and 8 ml TCA was added thereto. The sample in each tube was homogenized for 1 min, the homogenate was poured into a centrifuge tube and centrifuged at 3000 rpm for 15 min, and the supernatant was transferred into another tube. 1 ml of the supernatant was transferred into a 10 ml centrifuge tube to which 4 ml 95% ethanol was further added and thoroughly mixed until no interface was present between the two liquids. The opening of the centrifuge tube was sealed with a sealing film, and the tube was upright placed overnight at room temperature. After complete deposition, the tube was centrifuged at 3000 rpm for 15 min, the supernatant was then carefully discarded, and the tube was placed upside down for 10 min. Thereafter 2 ml distilled water was added to dissolve glycogen, and the glycogen content in liver was measured by the anthrone method.

1.3.6. Lactic Acid Measurement 30 minutes after the last intragastric administration, a 20 µl blood sample was taken from the tail of each of the 10 mice of the fourth subgroup. The mice were then allowed to swim without any burden in 30° C. water for 10 min. Another two 20 µl blood samples were further taken 0 min and 20 min after the swimming, respectively. Each of the three blood samples taken was added to a 0.48 ml 1% NaF solution and thoroughly mixed until clarity. Subsequently, 1.5 ml protein precipitating agent was added and mixed by shaking until homogenated. The mixture was centrifuged at 3000 rpm for 10 min, the supernatant was taken for lactic acid content determination, and the AUC under the blood lactic acid curve at 3 time points was calculated.

AUC under the blood lactic acid curve=½*(blood lactic acid level before swimming+blood lactic acid level 0 min after swimming)*10+½*(blood lactic acid level 0 min after swimming+blood lactic acid level after 20-min rest after swimming)*20

1.3.7 Statistic Methods

The experimental data are expressed as $\bar{x}\pm s$. One-way analysis of variance was employed to compare the measured indicators at the end of the experiments between the groups that received various doses of the oral liquid of TCM composition I and that received TCM composition II on one hand and the blank control group on the other for difference, and between the groups that received various doses of the oral liquid of TCM composition I on one hand and the group that received TCM composition II on the other for difference. $P<0.05$ indicates the difference is significant, and $P<0.01$ indicates the difference is highly significant.

2. Results 2.1 Body Weight Gain of the Animals

The experimental results are shown in Table 1 below. Compared to the blank control group, the mice groups that received various doses of the oral liquid of TCM composition I showed no significant difference in body weight. Compared to the group that received the other composition, the mice groups that received various doses of the composite powder for oral liquid of TCM composition I showed no significant difference in body weight.

TABLE 1

The effect of the oral liquid of TCM composition I on the
body weight gain of mice (g, x̄ ± s).

| | Group Name | Dose (g crude drugs/kg) | Number of Animals | Initial Body Weight | Final Body Weight |
|---|---|---|---|---|---|
| The first subgroup | Blank control group | 0.0 | 10 | 19.24 ± 1.08 | 39.65 ± 3.01 |
| | Group on TCM composition II | 4.0 | 10 | 19.29 ± 1.25 | 39.69 ± 3.20 |
| | Low-dose group on test medicine | 2.0 | 10 | 19.03 ± 1.28 | 38.46 ± 3.05 |
| | Medium-dose group on test medicine | 4.0 | 10 | 19.16 ± 1.23 | 39.02 ± 2.87 |
| | High-dose group on test medicine | 12.0 | 10 | 19.19 ± 1.17 | 39.57 ± 2.90 |
| The second subgroup | Blank control group | 0.0 | 10 | 19.45 ± 1.06 | 38.45 ± 3.21 |
| | Group on TCM composition II | 4.0 | 10 | 19.52 ± 1.15 | 39.29 ± 2.08 |
| | Low-dose group on test medicine | 2.0 | 10 | 19.40 ± 1.20 | 39.45 ± 3.21 |
| | Medium-dose group on test medicine | 4.0 | 10 | 19.55 ± 1.29 | 38.90 ± 2.78 |
| | High-dose group on test medicine | 12.0 | 10 | 19.43 ± 1.24 | 39.43 ± 3.54 |
| The third subgroup | Blank control group | 0.0 | 10 | 19.32 ± 1.01 | 39.63 ± 3.09 |
| | Group on TCM composition II | 4.0 | 10 | 19.29 ± 0.96 | 39.46 ± 2.60 |
| | Low-dose group on test medicine | 2.0 | 10 | 19.35 ± 1.21 | 38.69 ± 3.32 |
| | Medium-dose group on test medicine | 4.0 | 10 | 19.38 ± 1.20 | 38.65 ± 2.34 |
| | High-dose group on test medicine | 12.0 | 10 | 19.29 ± 1.23 | 39.00 ± 3.52 |
| The fourth subgroup | Blank control group | 0.0 | 10 | 19.33 ± 1.29 | 39.43 ± 2.26 |
| | Group on TCM composition II | 4.0 | 10 | 19.29 ± 1.30 | 38.72 ± 2.80 |
| | Low-dose group on test medicine | 2.0 | 10 | 19.53 ± 1.26 | 38.92 ± 2.75 |
| | Medium-dose group on test medicine | 4.0 | 10 | 19.43 ± 1.21 | 38.47 ± 3.20 |
| | High-dose group on test medicine | 12.0 | 10 | 19.52 ± 1.24 | 38.54 ± 2.44 |

2.2 Effects on the Burdened Swimming Time of Mice

The experimental results are shown in Table 2 below. Compared to the blank control group, the mice groups that received the low, medium, and high doses of the oral liquid of TCM composition I and the mice group that received TCM composition II all showed a remarkably longer burdened swimming time. Compared to the group that received TCM composition II, the mice groups that received the medium and high doses of the oral liquid of TCM composition I all showed a remarkably longer burdened swimming time.

TABLE 2

The effect of the oral liquid of TCM composition I on the burdened
swimming time of mice (x̄ ± s).

| Group Name | Dose (g crude drugs/kg) | Number of Animals | Burdened Swimming Time (min) |
|---|---|---|---|
| Blank control group | 0.0 | 10 | 3.81 ± 0.97 |
| Group on TCM composition II | 4.0 | 10 | 4.92 ± 1.00* |
| Low-dose group on test medicine | 2.0 | 10 | 4.93 ± 1.28* |
| Medium-dose group on test medicine | 4.0 | 10 | 5.94 ± 1.11**▲ |
| High-dose group on test medicine | 12.0 | 10 | 6.59 ± 1.01**▲▲ |

*$P < 0.05$ compared to the blank control group;
▲$P < 0.05$ and
▲▲$P < 0.01$ compared to the group on TCM composition II.

2.3 Effect on Serum Urea Nitrogen Level of Mice

The experimental results are shown in Table 3 below. Compared to the blank control group, the mice groups that received the low, medium, and high doses of the oral liquid of TCM composition I and the mice group that received TCM composition II showed no significant difference in serum urea nitrogen level after 90-min unburdened swimming. Compared to the group that received TCM composition II, the mice groups that received the low, medium, and high doses of the oral liquid of TCM composition I showed no significant difference in serum urea nitrogen level after 90-min unburdened swimming.

2.4 Effect on Liver Glycogen Level of Mice

The experimental results are shown in Table 3 below. The mice groups that received the low, medium, and high doses of the oral liquid of TCM composition I and the mice group that received TCM composition II showed a liver glycogen level remarkably higher than that of the blank control group, and the differences are significant. The mice groups that received the medium and high doses of the oral liquid of TCM composition I showed a liver glycogen level remarkably higher than that of the group that received TCM composition II, and the differences are significant.

TABLE 3

The effect of the oral liquid of TCM composition I on the serum urea nitrogen and liver glycogen levels of mice ($\bar{x} \pm s$).

| Group Name | Dose (g crude drugs/kg) | Number of Animals | Urea Nitrogen (mmol/L) | Liver Glycogen (mg/g liver tissue) |
|---|---|---|---|---|
| Blank control group | 0.0 | 10 | 9.58 ± 1.72 | 15.54 ± 3.44 |
| Group on TCM composition II | 4.0 | 10 | 10.05 ± 1.33 | 19.91 ± 4.92* |
| Low-dose group on test medicine | 2.0 | 10 | 9.80 ± 2.01 | 20.28 ± 4.07* |
| Medium-dose group on test medicine | 4.0 | 10 | 9.47 ± 1.83 | 23.50 ± 3.55**▲ |
| High-dose group on test medicine | 12.0 | 10 | 9.62 ± 1.69 | 24.26 ± 3.17**▲ |

*$P < 0.05$ compared to the blank control group;
▲$P < 0.05$ and
▲▲$P < 0.01$ compared to the group on TCM composition II.

2.5 Effect on Blood Lactic Acid Level of Mice

The experimental results are shown in Table 4 below. The mice groups that received various doses of the oral liquid of TCM composition I and the mice group that received TCM composition II all showed a blood lactic acid level immediately after swimming, a blood lactic acid level after a 20-min rest after swimming, and an AUC all remarkably lower than those of the blank control group. The mice groups that received the medium and high doses of the oral liquid of TCM composition I all showed a blood lactic acid level immediately after swimming, a blood lactic acid level after a 20-min rest after swimming, and an AUC all remarkably lower than those of the comparative group that received TCM composition II.

TABLE 4

The effect of the oral liquid of TCM composition I on the blood lactic acid level of mice (mg/L, $\bar{x} \pm s$).

| Group Name | Dose (g crude drugs/kg) | Number of Animals | Before Swimming | 0 min After Swimming | 20 min After Swimming | AUC |
|---|---|---|---|---|---|---|
| Blank control group | 0.0 | 10 | 209.40 ± 39.02 | 579.60 ± 57.51 | 320.40 ± 36.92 | 12971.00 ± 635.14 |
| Group on TCM composition II | 4.0 | 10 | 214.80 ± 38.67 | 503.60 ± 52.12* | 273.00 ± 31.61* | 11174.00 ± 927.12** |
| Low-dose group on test medicine | 2.0 | 10 | 221.60 ± 37.80 | 497.80 ± 72.16** | 272.70 ± 25.71** | 11124.00 ± 1196.67** |
| Medium-dose group on test medicine | 4.0 | 10 | 204.20 ± 39.24 | 444.50 ± 59.55**▲ | 239.60 ± 36.84**▲ | 10086.00 ± 1229.21**▲ |
| High-dose group on test medicine | 12.0 | 10 | 210.80 ± 35.29 | 430.30 ± 47.57**▲▲ | 205.80 ± 21.57**▲▲ | 9432.00 ± 775.52**▲▲ |

*$P < 0.05$ compared to the blank control group;
▲$P < 0.05$ and
▲▲$P < 0.01$ compared to the group on TCM composition II.

3. Conclusion

The daily intake dose of the composite powder for oral liquid of TCM composition I according to the present invention recommended for human (i.e., 24.0 g crude drugs/60 kg BW) was scaled up by 5, 10, and 30 times to set up a low-dose group, a medium-dose group, and a high-dose group, respectively, corresponding to the doses of 2.0 g, 4.0 g, and 12.0 g crude drugs per kg BW. A blank control group and a comparative group on TCM composition II were further set up. CL healthy male Kunming mice were continuously administered intragastrically with the test samples, and after 30 days experiments were conducted and related indicators were measured. $P < 0.05$ indicates the experimental results show significant difference, and $P < 0.01$ indicates the experimental results show highly significant difference. The animal experiments demonstrated that the mice groups that received the low, medium, and high doses of the oral liquid of TCM composition I are able to significantly reduce the AUCs under the blood lactic acid curve of the mice before, 0 min after, and 20 min after unburdened swimming, and to significantly increase the liver glycogen level of mice in a resting state. Furthermore, the mice groups that received the low, medium, and high doses of the oral liquid of TCM composition I showed a burdened swimming time remarkably longer than that of the blank control group. Compared to the comparative group that received TCM composition II, the mice groups that received the medium and high doses of the oral liquid of TCM composition I are able to significantly reduce the AUCs under the blood lactic acid curve of the mice before, 0 min after, and 20 min after unburdened swimming, and to significantly increase the liver glycogen level of mice in a resting state. Furthermore, the mice groups that received the medium and high doses of the oral liquid of TCM composition I showed a burdened swimming time remarkably longer than that of the comparative group that received TCM composition II. The oral liquid of TCM composition I is believed to have a function of relieving physical fatigue more effectively than the comparative group on TCM composition II.

Example 2

1. Materials and Methods

1.1 Sources of Samples

The test sample is composition II (herein refers to Radix Panacis Quinquefolii, *Ganoderma*, *Cordyceps*, and Flos Rosae Rugosae) provided by Jiangzhong Pharmaceutical Co. Ltd. as composite powder, and 1 g of this dry composite powder is equivalent to 12.19 g total crude drugs. The recommended daily intake dose per person thereof is 24 g crude drugs/60 kg BW.

The comparative sample is composition I (herein refers to Radix Panacis Quinquefolii, *Ganoderma*, fermented *Cordyceps sinensis* powder, and Flos Rosae Rugosae) provided by Jiangzhong Pharmaceutical Co. Ltd. as composite powder. 1 g of this dry composite powder is equivalent to 12.56 g total crude drugs. The recommended daily intake dose per person thereof is 24 g crude drugs/60 kg BW.

1.2 Laboratory Animals and Experimental Environments

CL healthy male Kunming mice, each weighing 18 to 22 g, were provided by the Laboratory Animal Center, Jiangxi University of Traditional Chinese Medicine (Certification Number: SCXK (Jiangxi)-2006-0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods

1.3.1 Animal Grouping 200 male Kunming mice were divided randomly into 4 groups (50 animals in each group) based on their body weights. Each animal group was further divided randomly into the following subgroups, i.e., a blank control group, test groups on a low dose, a medium dose, and a high dose of composition II, and a group on composition I (10 animals in each subgroup).

1.3.2 Dosage Design

The recommended daily intake dose per person of the composite powder of the test medicine, i.e. composition II, is 200 ml/60 kg BW. Every 1000 ml of composition II is formulated with 120 g total crude drugs, and thus the recommended daily intake dose per person is 24 g crude drugs/60 kg BW. Based on this dose, daily intake doses for mice are calculated as 2.0 g crude drugs/kg BW for the low-dose group, 4.0 g crude drugs/kg BW for the medium-dose group, and 12 g crude drugs/kg BW for the high-dose group, equivalent to 5, 10, and 30 times the daily intake dose for human, respectively. The samples were prepared in distilled water to make intragastric administration liquids having corresponding concentrations (i.e. 0.0164 g dry powder/ml, 0.0328 g dry powder/ml, 0.0984 g dry powder/ml) for experimentation. The intragastric administration amount for mice was calculated based on a ratio of 0.1 ml/10 g BW.

The recommended daily intake dose per person of composition I is 24 g crude drugs/60 kg BW. Based on this dose, intake doses for mice are calculated as 4.0 g crude drugs/kg BW (equivalent to 10 times the daily intake dose for human). The sample was prepared in distilled water to make a 0.0318 g dry powder/ml intragastric administration liquid for experimentation. The intragastric administration amount was calculated based on a ratio of 0.1 ml/10 g BW. The blank control group was given an equal volume of distilled water by intragastric administration. The intragastric administrations were conducted once a day and continued for 30 days. All mice groups were fed with common feed and allowed free access to feed and water. After 30 days, all subgroups of mice were subjected to a function test on relieving of physical fatigue.

1.3.3 Burdened Swimming Experiment 30 minutes after given the last test sample, the 10 mice of the first subgroup were each loaded a piece of lead weighing 5% of their body weight at the base of their tails. Then each burdened mouse was put into a swimming tank (with a depth≥30 cm, and water temperature of 25° C.±1.0° C.) to swim. The duration from the beginning of swimming to the death of the mouse was recorded as the burdened swimming time of the mouse.

1.3.4 Serum Urea Nitrogen Measurement 30 minutes after given the last test sample, the 10 mice of the second subgroup were allowed to swim without any burden in 30° C. water for 90 min. After a 60-minute rest, their eyeballs were taken out, and about 0.5 ml whole blood was collected and placed in a 4° C. fridge for about 3 h. When coagulated, the blood was centrifuged at 2000 rpm for 15 min, and the serum was isolated for urea nitrogen content determination.

The serum urea nitrogen was measured in Olympus AU400 automated Chemistry Analyzer (Japan), using the reagents provided by Daiichi Pure Chemicals Co., Ltd., Japan.

1.3.5 Liver Glycogen Measurement 30 minutes after given the last test sample, the 10 mice of the third subgroup were sacrificed. The livers were taken out, rinsed with saline solution, and blotted with filter paper. 100 mg liver was precisely weighed out, and 8 ml TCA was added thereto. The sample in each tube was homogenized for 1 min, the homogenate was poured into a centrifuge tube and centrifuged at 3000 rpm for 15 min, and the supernatant was transferred into another tube. 1 ml of the supernatant was transferred into a 10 ml centrifuge tube to which 4 ml 95% ethanol was further added and thoroughly mixed until no interface was present between the two liquids. The opening of the centrifuge tube was sealed with a sealing film, and the tube was upright placed overnight at room temperature. After complete deposition, the tube was centrifuged at 3000 rpm for 15 min, the supernatant was then carefully discarded, and the tube was placed upside down for 10 min. Thereafter 2 ml distilled water was added to dissolve glycogen, and the glycogen content in liver was measured by the anthrone method.

1.3.6. Lactic Acid Measurement 30 minutes after the last intragastric administration, a 20 µl blood sample was taken from the tail of each of the 10 mice of the fourth subgroup. The mice were then allowed to swim without any burden in 30° C. water for 10 min. Another two 20 µl blood samples were further taken 0 min and 20 min after swimming, respectively. Each of the three blood samples taken was added to a 0.48 ml 1% NaF solution and thoroughly mixed until clarity. Subsequently, 1.5 ml protein precipitating agent was added and mixed by shaking until homogenated. The mixture was centrifuged at 3000 rpm for 10 min, the supernatant was taken for lactic acid content determination, and the AUC under the blood lactic acid curve at 3 time points was calculated.

$$\text{AUC under the blood lactic acid curve} = \tfrac{1}{2}*(\text{blood lactic acid level before swimming} + \text{blood lactic acid level 0 min after swimming})*10 + \tfrac{1}{2}*(\text{blood lactic acid level 0 min after swimming} + \text{blood lactic acid level after 20-min rest after swimming})*20$$

1.3.7 Statistic Methods

The experimental data are expressed as $\bar{x} \pm s$. One-way analysis of variance was employed to compare the measured indicators at the end of the experiments between the groups that received various doses of composition II and that received composition I on one hand and the blank control group on the other for difference, and between the groups that received various doses of composition II on one hand and the group that received composition I on the other for difference. P<0.05 indicates the difference is significant, and P<0.01 indicates the difference is highly significant.

2. Results 2.1 Body Weight Gain of the Animals

The experimental results are shown in Table 1 below. Compared to the blank control group, the mice groups that received various doses of composition II showed no significant difference in body weight. Compared to the group that received composition I, the mice groups that received various doses of composition II showed no significant difference in body weight.

TABLE 1

The effect of composition II on the body weight gain of mice (g, $\bar{x} \pm s$).

| | Group Name | Dose (g crude drugs/kg) | Number of Animals | Initial Body Weight | Final Body Weight |
|---|---|---|---|---|---|
| The first subgroup | Blank control group | 0.0 | 10 | 19.75 ± 1.12 | 39.25 ± 3.46 |
| | Group on composition I | 4.0 | 10 | 19.86 ± 1.21 | 39.45 ± 3.50 |
| | Low-dose group on test medicine | 2.0 | 10 | 19.92 ± 1.30 | 38.33 ± 3.28 |
| | Medium-dose group on test medicine | 4.0 | 10 | 19.68 ± 1.16 | 39.63 ± 2.86 |
| | High-dose group on test medicine | 12.0 | 10 | 19.74 ± 1.33 | 39.85 ± 2.94 |
| The second subgroup | Blank control group | 0.0 | 10 | 19.85 ± 1.25 | 38.90 ± 3.27 |
| | Group on composition I | 4.0 | 10 | 19.92 ± 1.30 | 39.47 ± 3.08 |
| | Low-dose group on test medicine | 2.0 | 10 | 19.80 ± 1.28 | 39.82 ± 3.44 |
| | Medium-dose group on test medicine | 4.0 | 10 | 19.75 ± 1.27 | 38.70 ± 2.90 |
| | High-dose group on test medicine | 12.0 | 10 | 19.86 ± 1.32 | 39.28 ± 3.28 |
| The third subgroup | Blank control group | 0.0 | 10 | 19.92 ± 1.25 | 39.04 ± 3.21 |
| | Group on composition I | 4.0 | 10 | 19.68 ± 1.20 | 39.22 ± 2.72 |
| | Low-dose group on test medicine | 2.0 | 10 | 19.94 ± 1.33 | 39.09 ± 3.29 |
| | Medium-dose group on test medicine | 4.0 | 10 | 19.76 ± 1.26 | 38.79 ± 2.70 |
| | High-dose group on test medicine | 12.0 | 10 | 19.82 ± 1.30 | 39.22 ± 3.44 |
| The fourth subgroup | Blank control group | 0.0 | 10 | 19.78 ± 1.21 | 39.38 ± 3.26 |
| | Group on composition I | 4.0 | 10 | 19.69 ± 1.32 | 38.98 ± 3.80 |
| | Low-dose group on test medicine | 2.0 | 10 | 19.90 ± 1.22 | 38.90 ± 2.90 |
| | Medium-dose group on test medicine | 4.0 | 10 | 19.82 ± 1.25 | 38.92 ± 3.16 |
| | High-dose group on test medicine | 12.0 | 10 | 19.78 ± 1.27 | 38.93 ± 3.40 |

2.2 Effects on the Burdened Swimming Time of Mice

The experimental results are shown in Table 2 below. Compared to the blank control group, the mice groups that received the low, medium, and high doses of composition II and the mice group that received composition I all showed a remarkably longer burdened swimming time. Compared to the group that received composition I, the mice groups that received the medium and high doses of composition II both showed a remarkably longer burdened swimming time.

TABLE 2

The effect of composition II on the burdened swimming time of mice ($\bar{x} \pm s$).

| Group Name | Dose (g crude drugs/kg) | Number of Animals | Burdened Swimming Time (min) |
|---|---|---|---|
| Blank control group | 0.0 | 10 | 3.44 ± 0.82 |
| Group on composition I | 4.0 | 10 | 4.78 ± 1.06* |
| Low-dose group on test medicine | 2.0 | 10 | 4.96 ± 1.28* |
| Medium-dose group on test medicine | 4.0 | 10 | 5.83 ± 1.03**▲ |
| High-dose group on test medicine | 12.0 | 10 | 6.52 ± 1.01**▲▲ |

*P < 0.05 compared to the blank control group;
▲P < 0.05 and
▲▲P < 0.01 compared to the group on composition I.

2.3 Effect on Serum Urea Nitrogen Level of Mice

The experimental results are shown in Table 3 below. Compared to the blank control group, the mice groups that received the low, medium, and high doses of composition II and the mice group that received composition I showed no significant difference in serum urea nitrogen level after 90-min unburdened swimming. Compared to the group that received composition I, the mice groups that received the low, medium, and high doses of composition II showed no significant difference in serum urea nitrogen level after 90-min unburdened swimming.

2.4 Effect on Liver Glycogen Level of Mice

The experimental results are shown in Table 3 below. The mice groups that received the low, medium, and high doses of composition II and the mice group that received composition I showed a liver glycogen level remarkably higher than that of the blank control group, and the differences are significant. The mice groups that received the medium and high doses of composition II showed a liver glycogen level remarkably higher than that of the group that received composition I, and the differences are significant.

TABLE 3

The effect of composition II on the serum urea nitrogen and liver glycogen levels of mice ($\bar{x} \pm s$).

| Group Name | Dose (g crude drugs/kg) | Number of Animals | Urea Nitrogen (mmol/L) | Liver Glycogen (mg/g liver tissue) |
|---|---|---|---|---|
| Blank control group | 0.0 | 10 | 9.67 ± 1.80 | 15.63 ± 3.30 |
| Group on composition I | 4.0 | 10 | 9.52 ± 1.60 | 20.07 ± 4.90* |
| Low-dose group on test medicine | 2.0 | 10 | 9.66 ± 2.06 | 20.70 ± 3.66* |
| Medium-dose group on test medicine | 4.0 | 10 | 9.52 ± 1.64 | 23.79 ± 3.35**▲ |
| High-dose group on test medicine | 12.0 | 10 | 9.88 ± 1.72 | 25.43 ± 3.44**▲ |

*P < 0.05 compared to the blank control group;
▲P < 0.05 and
▲▲P < 0.01 compared to the group on composition I.

2.5 Effect on Blood Lactic Acid Level of Mice

The experimental results are shown in Table 4 below. The mice groups that received various doses of composition II and the mice group that received composition I all showed a blood lactic acid level immediately after swimming, a blood lactic acid level after a 20-min rest after swimming, and an AUC all remarkably lower than those of the blank control group. The mice groups that received the medium and high doses of composition II all showed a blood lactic acid level immediately after swimming, a blood lactic acid level after a 20-min rest after swimming, and an AUC all remarkably lower than those of the comparative group that received composition I.

TABLE 4

The effect of composition II on the blood lactic acid level of mice (mg/L, $\bar{x} \pm s$).

| Group Name | Dose (g crude drugs/kg) | Number of Animals | Before Swimming | 0 min After Swimming | 20 min After Swimming | AUC |
|---|---|---|---|---|---|---|
| Blank control group | 0.0 | 10 | 212.50 ± 39.91 | 580.50 ± 61.31 | 326.20 ± 36.33 | 13017.00 ± 747.40 |
| Group on composition I | 4.0 | 10 | 215.70 ± 37.99 | 495.00 ± 50.91** | 265.00 ± 31.50** | 11157.50 ± 907.94** |
| Low-dose group on test medicine | 2.0 | 10 | 223.50 ± 36.62 | 496.40 ± 71.53** | 254.10 ± 25.95** | 11104.50 ± 1191.40** |
| Medium-dose group on test medicine | 4.0 | 10 | 205.30 ± 39.81 | 440.10 ± 61.15**▲ | 234.80 ± 36.52**▲ | 10061.00 ± 1237.23**▲ |
| High-dose group on test medicine | 12.0 | 10 | 213.30 ± 35.31 | 419.10 ± 47.39**▲▲ | 205.10 ± 22.76**▲▲ | 9404.00 ± 977.83**▲▲ |

*P < 0.05 compared to the blank control group;
▲P < 0.05 and
▲▲P < 0.01 compared to the group on composition I.

3. Conclusion

The daily intake dose of the composite powder for oral liquid of the TCM composition according to the present invention recommended for human (i.e., 24.0 g crude drugs/60 kg BW) was scaled up by 5, 10, and 30 times to set up a low-dose group, a medium-dose group, and a high-dose group, respectively, corresponding to the doses of 2.0 g, 4.0 g, and 12.0 g crude drugs per kg BW. A blank control group and a comparative group on composition I were further set up. CL healthy male Kunming mice were continuously administered intragastrically with the test samples, and after 30 days experiments were conducted and related indicators were measured. $P<0.05$ indicates the experimental results show significant difference, and $P<0.01$ indicates the experimental results show highly significant difference. The animal experiments demonstrated that the mice groups that received the low, medium, and high doses of composition II are able to significantly reduce the AUCs under the blood lactic acid curve of the mice before, 0 min after, and 20 min after unburdened swimming, and to significantly increase the liver glycogen level of mice in a resting state. Furthermore, the mice groups that received the low, medium, and high doses of composition II showed a burdened swimming time remarkably longer than that of the blank control group. Compared to the comparative group that received composition I, the mice groups that received the medium and high doses of composition II are able to significantly reduce the AUCs under the blood lactic acid curve of the mice before, 0 min after, and 20 min after unburdened swimming, and to significantly increase the liver glycogen level of mice in a resting state. Furthermore, the mice groups that received the medium and high doses of composition II showed a burdened swimming time remarkably longer than that of the comparative group that received composition I. Composition II is believed to have a function of relieving physical fatigue more effectively than the comparative group on composition I.

Example 3

1. Materials and Methods
1.1 Sources of Samples

The test sample is composition II (herein refers to Radix Panacis Quinquefolii, *Ganoderma, Cordyceps*, and Flos Rosae Rugosae) provided by Jiangzhong Pharmaceutical Co. Ltd. as composite powder, and 1 g of this dry composite powder is equivalent to 12.19 g total crude drugs. The recommended daily intake dose per person thereof is 24 g crude drugs/60 kg BW.

The comparative sample is composition I (herein refers to Radix Panacis Quinquefolii, *Ganoderma, Cordyceps sinensis* powder, and Flos Rosae Rugosae) provided by Jiangzhong Pharmaceutical Co. Ltd. as composite powder. 1 g of this dry composite powder is equivalent to 12.56 g total crude drugs. The recommended daily intake dose per person thereof is 24 g crude drugs/60 kg BW.

1.2 Laboratory Animals and Experimental Environments

CL healthy male SD rats, each weighing 150 to 200 g, were provided by the Laboratory Animal Center, Jiangxi University of Traditional Chinese Medicine (SCXK (Jiangxi)-2006-0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods
1.3.1 Animal Grouping 60 male SD rats, each weighing 150-200 g, were adaptively fed with basic feed for one week. Thereafter blood samples were taken for determination of serum levels of total cholesterol (TC), triglyceride (TG), and high-density lipoprotein-cholesterol (HDL-C). The rats were divided into 6 groups (10 animals in each group) based on their TC level and body weights. A basic-feed control group, a high-fat-feed control group, three test groups on low, medium and high doses of the test medicine, and a comparative group on composition I were set up.

1.3.2 Dosage Design

The recommended daily intake dose per person of the test medicine, i.e. composition II, is 200 ml/60 kg BW. Every 1000 ml of composition II is formulated with 120 g total crude drugs, and thus the recommended daily intake dose per person is 24 g crude drugs/60 kg BW. Based on this dose, daily intake doses for rats are calculated as 1.0 g crude drugs/kg BW for the low-dose group, 2.0 g crude drugs/kg BW for the medium-dose group, and 6.0 g crude drugs/kg BW for the high-dose group, equivalent to 2.5, 5, and 15 times the daily intake dose for human, respectively. The test samples were prepared in distilled water to make intragastric administration liquids having corresponding concentrations (i.e. 0.0082 g dry powder/ml, 0.0164 g dry powder/ml, 0.0492 g dry powder/ml) for experimentation. The intragastric administration amounts for rats were calculated based on a ratio of 1.0 ml/100 g BW. The recommended daily intake dose per person of composition I is 24 g crude drugs/60 kg BW. Based on this dose, daily intake dose for rats is calculated as 2.0 g crude drugs/kg BW (equivalent to 5 times the daily intake dose for human). The sample was prepared in distilled water to make a 0.0159 g dry powder/ml intragastric administration liquid for experimentation. The intragastric administration amount thereof was calculated based on a ratio of 1.0 ml/100 g BW.

When the experiment was initiated, only the rats in the basic-feed control group were fed with basic feed, and the other groups of rats were all fed with high-fat feed (composition of the high-fat feed: 78.8% basic feed, 1% cholesterol, 10% custard powder, 10% lard, and 0.2% chocolate).

The test groups and the group on composition I each received various doses of the administration liquids. The basic-feed control group and the high-fat-feed control group received an equal volume of distilled water by intragastric administration. The intragastric administrations were conducted once a day and continued for 30 days, and body weights were measured every week. All rats groups were allowed free access to feed and water. After 30 days, blood samples were taken from the femoral artery, and serum samples were isolated for determination of related indicators.

1.3.3 Examined Indicators

The levels of TC (by enzymatic means), TG (by enzymatic means), and HDL-C (by a direct method) were measured in Beckman-CX7 automated blood chemistry analyzer, using the reagents purchased from Nanjing Jiancheng.

1.3.4 Statistic Methods

The experimental data are expressed as $\bar{x}\pm s$. One-way analysis of variance was employed to compare the serum levels of TC, TG, and HDL-C of the rats at the end of the experiments between the dosed test groups and the group on composition I on one hand and the high-fat control group on the other for difference, and between the dosed test groups on one hand and the group on composition I on the other for difference. $P<0.05$ indicates the difference is significant, and $P<0.01$ indicates the difference is highly significant.

2. Results
2.1 Effect of Composition II on the Body Weight of the Rats in the Experiments The experimental results are shown in Table 1 below. Compared to the high-fat-feed control group, the rats groups that received various doses of composition II and the rats group that received composition I showed no significant difference in body weight. Compared to the comparative rats group that received composition I, the rats groups that received various doses of composition II showed no significant difference in body weight.

TABLE 1

The effect of composition II on the body weight of the rats in the experiments (g, $\bar{x} \pm s$)

| Group Name | Dose (g crude drugs/kg) | n | Week 0 | Week 1 | Week 2 | Week 3 | Week 4 |
|---|---|---|---|---|---|---|---|
| Basic-feed control group | 0.0 | 10 | 175.8 ± 13.4 | 223.6 ± 15.0 | 272.1 ± 22.1 | 325.8 ± 29.0 | 385.2 ± 32.1 |
| High-fat-feed control group | 0.0 | 10 | 174.6 ± 12.0 | 234.8 ± 14.5 | 269.4 ± 23.2 | 329.0 ± 29.8 | 376.7 ± 31.5 |
| Group on composition I | 2.0 | 10 | 179.1 ± 11.5 | 225.2 ± 13.2 | 279.4 ± 24.0 | 329.2 ± 27.8 | 389.0 ± 32.0 |
| Low-dose group on test medicine | 1.0 | 10 | 180.5 ± 10.7 | 232.6 ± 14.7 | 262.8 ± 25.8 | 336.5 ± 27.2 | 388.1 ± 30.2 |
| Medium-dose group on test medicine | 2.0 | 10 | 182.3 ± 10.9 | 224.0 ± 12.6 | 265.4 ± 23.4 | 338.2 ± 25.0 | 385.3 ± 29.8 |
| High-dose group on test medicine | 6.0 | 10 | 179.6 ± 11.6 | 232.9 ± 13.0 | 268.9 ± 22.8 | 330.7 ± 27.1 | 376.4 ± 27.7 |

2.2 Effect of Composition II on the Blood Lipid Level of the Rats

See Tables 2 and 3 below for the results. At the beginning of the experiment, there was no significant difference in serum levels of TC, TG, and HDL-C between the rats groups. At the end of the experiment, the rats in the high-fat-feed control group showed the serum levels of TC and TG significantly higher than those of the basic-feed control group, indicating successful establishment of a high-fat model. The rats groups that received various doses of composition II and the rats group that received composition I showed a serum TC level lower than that of the high-fat-feed control group, and the difference is significant. The rats groups that received the low, medium, and high doses of composition II and the rats group that received composition I showed a serum TG level lower than that of the high-fat-feed control group, and the difference is significant. Compared to the high-fat-feed control group, the rats groups that received the low, medium, and high doses of composition II and the rats group that received composition I showed no significant difference in serum HDL-C level.

The rats groups that received the medium and high doses of composition II showed a serum TC level lower than that of the comparative rats group that received composition I, and the difference is significant. The rats groups that received the medium and high doses of composition II showed a serum TG level lower than that of the comparative rats group that received composition I, and the difference is significant. Compared to the comparative rats group that received composition I, the rats groups that received the low, medium, and high doses of composition II showed no significant difference in serum HDL-C level.

TABLE 2

Serum levels of TC, TG, and HDL-C of the rats at the beginning of the experiment (mmol/L, $\bar{X} \pm S$)

| Group Name | Dose (g crude drugs/kg) | Number of Animals | TC | TG | HDL-C |
|---|---|---|---|---|---|
| Basic-feed control group | 0.0 | 10 | 2.27 ± 0.30 | 1.30 ± 0.20 | 1.25 ± 0.18 |
| High-fat-feed control group | 0.0 | 10 | 2.32 ± 0.25 | 1.26 ± 0.32 | 1.28 ± 0.22 |
| Group on composition I | 2.0 | 10 | 2.30 ± 0.28 | 1.35 ± 0.31 | 1.26 ± 0.16 |
| Low-dose group on test medicine | 1.0 | 10 | 2.20 ± 0.32 | 1.30 ± 0.23 | 1.24 ± 0.17 |
| Medium-dose group on test medicine | 2.0 | 10 | 2.33 ± 0.25 | 1.27 ± 0.27 | 1.20 ± 0.21 |
| High-dose group on test medicine | 6.0 | 10 | 2.21 ± 0.28 | 1.21 ± 0.22 | 1.26 ± 0.12 |

TABLE 3

The effect of composition II on the serum levels of TC, TG, and HDL-C of the rats (mmol/L, $\bar{X} \pm S$)

| Group Name | Dose (g crude drugs/kg) | Number of Animals | TC | TG | HDL-C |
|---|---|---|---|---|---|
| Basic feed control group | 0.0 | 10 | 2.24 ± 0.24** | 1.20 ± 0.25* | 1.25 ± 0.18 |
| High-fat-feed control group | 0.0 | 10 | 3.80 ± 0.33 | 1.87 ± 0.21 | 1.26 ± 0.22 |
| Group on composition I | 2.0 | 10 | 3.10 ± 0.40* | 1.38 ± 0.21* | 1.20 ± 0.20 |
| Low-dose group on test medicine | 1.0 | 10 | 3.12 ± 0.33* | 1.32 ± 0.30* | 1.32 ± 0.18 |

TABLE 3-continued

The effect of composition II on the serum levels of TC, TG, and HDL-C of the rats (mmol/L, $\overline{X} \pm S$)

| Group Name | Dose (g crude drugs/kg) | Number of Animals | TC | TG | HDL-C |
|---|---|---|---|---|---|
| Medium-dose group on test medicine | 2.0 | 10 | 2.20 ± 0.29**▲ | 0.93 ± 0.32*▲ | 1.30 ± 0.22 |
| High-dose group on test medicine | 6.0 | 10 | 2.07 ± 0.32**▲ | 0.80 ± 0.20**▲ | 1.30 ± 0.20 |

*P < 0.05 and
**P < 0.05 compared to the basic-feed control group;
▲P < 0.05 and
▲▲P < 0.01 compared to the group on composition I.

3. Conclusion

The daily intake dose of composition II recommended for human (i.e., 24 g crude drugs/60 kg BW) was scaled up by 2.5, 5, and 15 times to set up a low-dose group, a medium-dose group, and a high-dose group, respectively, corresponding to the doses of 1.0 g, 2.0 g, and 6.0 g crude drugs per kg BW. A basic-feed control group and a high-fat-feed control group were further set up. CL healthy male SD rats were continuously administered intragastrically with the test samples, and after 30 days the related indicators were measured. P<0.05 indicates the experimental results show significant difference. The animal experiments demonstrated that the rats groups that received the low, medium, and high doses of composition II showed the levels of serum total cholesterol (TC) and serum triglyceride (TG) significantly lower than those of the high-fat-feed control group, and that the rats groups that received the medium and high doses of composition II showed the levels of serum total cholesterol (TC) and serum triglyceride (TG) significantly lower than those of the comparative group that received composition I. Composition II is believed to have a function of helping reduce blood lipids more effectively than the group on composition I.

Example 4

1. Materials and Methods
1.1 Sources of Samples

The test sample is TCM composition I (herein refers to Radix Panacis Quinquefolii, *Ganoderma*, and *Cordyceps*) provided by Jiangzhong Pharmaceutical Co. Ltd. as composite powder for oral liquid, and 1 g of this dry composite powder is equivalent to 11.41 g total crude drugs. The recommended daily intake dose per person thereof is 24 g crude drugs/60 kg BW.

The comparative sample is TCM composition II (herein refers to Radix Panacis Quinquefolii, *Ganoderma*, and *Cordyceps sinensis* powder) provided by Jiangzhong Pharmaceutical Co. Ltd. as composite powder. 1 g of this dry composite powder is equivalent to 10.97 g total crude drugs. The recommended daily intake dose per person thereof is 24 g crude drugs/60 kg BW.

1.2 Laboratory Animals and Experimental Environments

CL healthy male SD rats, each weighing 150 to 200 g, were provided by the Laboratory Animal Center, Jiangxi University of Traditional Chinese Medicine (SCXK (Jiangxi)-2006-0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods
1.3.1 Animal Grouping 60 male SD rats, each weighing 150-200 g, were adaptively fed with basic feed for one week. Thereafter blood samples were taken for determination of serum levels of total cholesterol (TC), triglyceride (TG), and high-density lipoprotein-cholesterol (HDL-C). The rats were divided into 6 groups (10 animals in each group) based on their TC level and body weights. A basic-feed control group, a high-fat-feed control group, three test groups on low, medium and high doses of the test medicine, and a comparative group on TCM composition II were set up.

1.3.2 Dosage Design

The recommended daily intake dose per person of the oral liquid of the test medicine, i.e. TCM composition I, is 200 ml/60 kg BW. Every 1000 ml of the oral liquid of TCM composition I is formulated with 120 g total crude drugs, and thus the recommended daily intake dose per person is 24 g crude drugs/60 kg BW. Based on this dose, daily intake doses for rats are calculated as 1.0 g crude drugs/kg BW for the low-dose group, 2.0 g crude drugs/kg BW for the medium-dose group, and 6.0 g crude drugs/kg BW for the high-dose group, equivalent to 2.5, 5, and 15 times the daily intake dose for human, respectively. The test samples were prepared in distilled water to make intragastric administration liquids having corresponding concentrations (i.e. 0.0088 g dry powder/ml, 0.0175 g dry powder/ml, 0.0525 g dry powder/ml) for experimentation. The intragastric administration amounts for rats were calculated based on a ratio of 1.0 ml/100 g BW.

The recommended daily intake dose per person of TCM composition II is 24 g crude drugs/60 kg BW. Based on this dose, daily intake dose for rats is calculated as 2.0 g crude drugs/kg BW (equivalent to 5 times the daily intake dose for human). The sample was prepared in distilled water to make a 0.0182 g dry powder/ml intragastric administration liquid for experimentation. The intragastric administration amount thereof was calculated based on a ratio of 1.0 ml/100 g BW.

When the experiment was initiated, only the rats in the basic-feed control group were fed with basic feed, and the other groups of rats were all fed with high-fat feed (composition of the high-fat feed: 78.8% basic feed, 1% cholesterol, 10% custard powder, 10% lard, and 0.2% chocolate).

The test groups and the group on composition II each received various doses of the administration liquids. The basic-feed control group and the high-fat-feed control group received an equal volume of distilled water by intragastric administration. The intragastric administrations were conducted once a day and continued for 30 days, and body weights were measured every week. All rats groups were allowed free access to feed and water. After 30 days, blood samples were taken from the femoral artery, and serum samples were isolated for determination of related indicators.

1.3.3 Examined Indicators

The levels of TC (by enzymatic means), TG (by enzymatic means), and HDL-C (by the direct method) were measured in Beckman-CX7 automated blood chemistry analyzer, using the reagents purchased from Nanjing Jiancheng.

1.3.4 Statistic Methods

The experimental data are expressed as $\bar{x} \pm s$. One-way analysis of variance was employed to compare the serum levels of TC, TG, and HDL-C of the rats at the end of the experiments between the dosed test groups and the group on TCM composition II on one hand and the high-fat control group on the other for difference, and between the dosed test groups on one hand and the group on TCM composition II on the other for difference. $P<0.05$ indicates the difference is significant, and $P<0.01$ indicates the difference is highly significant.

2. Results 2.1 Effect of the Oral Liquid of TCM Composition I on the Body Weight of the Rats in The Experiments.

The experimental results are shown in Table 1 below. Compared to the high-fat-feed control group, the rats groups that received various doses of the oral liquid of TCM composition I and the rats group that received TCM composition II showed no significant difference in body weight. Compared to the comparative rats group that received TCM composition II, the rats groups that received various doses of the oral liquid of TCM composition I showed no significant difference in body weight.

serum levels of TC, TG, and HDL-C between the rats groups. At the end of the experiment, the rats in the high-fat-feed control group showed the serum levels of TC and TG significantly higher than those of the basic-feed control group, indicating successful establishment of a high-fat model. The rats groups that received various doses of the oral liquid of TCM composition I and the rats group that received TCM composition II showed a serum TC level lower than that of the high-fat-feed control group, and the difference is significant. The rats groups that received the low, medium, and high doses of the oral liquid of TCM composition I and the rats group that received TCM composition II showed a serum TG level lower than that of the high-fat-feed control group, and the difference is significant. Compared to the high-fat-feed control group, the rats groups that received the low, medium, and high doses of the oral liquid of TCM composition I and the rats group that received TCM composition II showed no significant difference in serum HDL-C level.

The rats groups that received the medium and high doses of the oral liquid of TCM composition I showed a serum TC level lower than that of the comparative rats group that received TCM composition II, and the difference is significant. The rats groups that received the medium and high doses of the oral liquid of TCM composition I showed a serum TG level lower than that of the comparative rats group that received TCM composition II, and the difference is significant. Compared to the comparative rats group that received

TABLE 1

The effect of the oral liquid of TCM composition I on the body weight of the rats in the experiments (g, $\bar{x} \pm s$).

| Group Name | Dose (g crude drugs/kg) | n | Week 0 | Week 1 | Week 2 | Week 3 | Week 4 |
|---|---|---|---|---|---|---|---|
| Basic-feed control group | 0.0 | 10 | 166.3 ± 12.2 | 212.7 ± 14.9 | 260.4 ± 20.3 | 322.0 ± 29.5 | 383.8 ± 30.4 |
| High-fat-feed control group | 0.0 | 10 | 163.9 ± 10.6 | 221.0 ± 16.3 | 258.3 ± 22.6 | 321.6 ± 29.1 | 379.5 ± 31.2 |
| Group on TCM composition II | 2.0 | 10 | 169.9 ± 11.9 | 216.5 ± 14.2 | 268.9 ± 25.4 | 324.5 ± 27.6 | 385.5 ± 33.5 |
| Low-dose group on test medicine | 1.0 | 10 | 170.4 ± 9.8 | 220.3 ± 14.9 | 266.0 ± 25.1 | 326.7 ± 25.0 | 386.7 ± 34.2 |
| Medium-dose group on test medicine | 2.0 | 10 | 172.4 ± 10.1 | 215.8 ± 15.0 | 267.1 ± 23.0 | 329.5 ± 25.8 | 379.0 ± 27.8 |
| High-dose group on test medicine | 6.0 | 10 | 169.3 ± 11.2 | 220.1 ± 13.2 | 262.7 ± 22.5 | 320.6 ± 24.5 | 373.7 ± 27.0 |

2.2 Effect of the Oral Liquid of TCM Composition I on the Blood Lipid Level of the Rats See Tables 2 and 3 below for the results. At the beginning of the experiment, there was no significant difference in TCM composition II, the rats groups that received the low, medium, and high doses of the oral liquid of TCM composition II showed no significant difference in serum HDL-C level.

TABLE 2

Serum levels of TC, TG, and HDL-C of the rats at the beginning of the experiment (mmol/L, $\bar{X} \pm S$)

| Group Name | Dose (g crude drugs/kg) | Number of Animals | TC | TG | HDL-C |
|---|---|---|---|---|---|
| Basic-feed control group | 0.0 | 10 | 2.42 ± 0.33 | 1.28 ± 0.21 | 1.21 ± 0.15 |
| High-fat-feed control group | 0.0 | 10 | 2.47 ± 0.35 | 1.29 ± 0.30 | 1.18 ± 0.20 |
| Group on TCM composition II | 2.0 | 10 | 2.36 ± 0.34 | 1.32 ± 0.35 | 1.16 ± 0.12 |

TABLE 2-continued

Serum levels of TC, TG, and HDL-C of the rats at the beginning of the experiment (mmol/L, $\overline{X} \pm S$)

| Group Name | Dose (g crude drugs/kg) | Number of Animals | TC | TG | HDL-C |
|---|---|---|---|---|---|
| Low-dose group on test medicine | 1.0 | 10 | 2.41 ± 0.30 | 1.35 ± 0.33 | 1.14 ± 0.18 |
| Medium-dose group on test medicine | 2.0 | 10 | 2.43 ± 0.26 | 1.30 ± 0.34 | 1.10 ± 0.22 |
| High-dose group on test medicine | 6.0 | 10 | 2.36 ± 0.25 | 1.37 ± 0.32 | 1.13 ± 0.15 |

TABLE 3

The effect of the oral liquid of TCM composition I on the serum levels of TC, TG, and HDL-C of the rats (mmol/L, $\overline{X} \pm S$)

| Group Name | Dose (g crude drugs/kg) | Number of Animals | TC | TG | HDL-C |
|---|---|---|---|---|---|
| Basic-feed control group | 0.0 | 10 | 2.61 ± 0.26* | 1.31 ± 0.25* | 1.18 ± 0.14 |
| High-fat-feed control group | 0.0 | 10 | 3.77 ± 0.30 | 1.76 ± 0.24 | 1.17 ± 0.12 |
| Group on TCM composition II | 2.0 | 10 | 3.16 ± 0.40* | 1.38 ± 0.21* | 1.15 ± 0.20 |
| Low-dose group on test medicine | 1.0 | 10 | 3.09 ± 0.38* | 1.32 ± 0.30* | 1.20 ± 0.18 |
| Medium-dose group on test medicine | 2.0 | 10 | 2.40 ± 0.29**▲ | 1.03 ± 0.32*▲ | 1.16 ± 0.21 |
| High-dose group on test medicine | 6.0 | 10 | 2.18 ± 0.36**▲ | 0.87 ± 0.20**▲ | 1.22 ± 0.25 |

*$P < 0.05$ and
**$P < 0.05$ compared to the basic-feed control group;
▲$P < 0.05$ and
▲▲$P < 0.01$ compared to the group on TCM composition II.

3. Conclusion

The daily intake dose of the oral liquid of TCM composition I recommended for human (i.e., 24 g crude drugs/60 kg BW) was scaled up by 2.5, 5, and 15 times to set up a low-dose group, a medium-dose group, and a high-dose group, respectively, corresponding to the doses of 1.0 g, 2.0 g, and 6.0 g crude drugs per kg BW. A basic-feed control group and a high-fat-feed control group were further set up. CL healthy male SD rats were continuously administered intragastrically with the test samples, and after 30 days the related indicators were measured. $P<0.05$ indicates the experimental results show significant difference. The animal experiments demonstrated that the rats groups that received the low, medium, and high doses of the oral liquid of TCM composition I showed the levels of serum total cholesterol (TC) and serum triglyceride (TG) significantly lower than those of the high-fat-feed control group, and that the rats groups that received the medium and high doses of the oral liquid of TCM composition I showed the levels of serum total cholesterol (TC) and serum triglyceride (TG) significantly lower than those of the comparative group that received TCM composition II. The oral liquid of TCM Composition I is believed to have a function of helping reduce blood lipids more effectively than the group on TCM composition II.

Example 5

1. Materials and Methods
1.1 Sources of Samples

The test sample is composition II (herein refers to Radix Panacis Quinquefolii, Ganoderma, Cordyceps, and Flos Rosae Rugosae) provided by Jiangzhong Pharmaceutical Co. Ltd. as composite powder, and 1 g of this dry composite powder is equivalent to 12.19 g total crude drugs. The recommended daily intake dose per person thereof is 24 g crude drugs/60 kg BW.

The comparative sample is composition I (herein refers to Radix Panacis Quinquefolii, Ganoderma, Cordyceps sinensis powder, and Flos Rosae Rugosae) provided by Jiangzhong Pharmaceutical Co. Ltd. as composite powder. 1 g of this dry composite powder is equivalent to 12.56 g total crude drugs. The recommended daily intake dose per person thereof is 24 g crude drugs/60 kg BW.

1.2 Laboratory Animals and Experimental Environments

CL healthy male Kunming mice, each weighing 18 to 22 g, were provided by the Laboratory Animal Center, Jiangxi University of Traditional Chinese Medicine (Certification Number: SCXK (Jiangxi)-2006-0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods
1.3.1 Animal Grouping 60 mice were divided randomly into 6 groups based on their body weights. A blank control group, a model control group, a group on composition I, and test groups on a low dose, a medium dose, and a high dose of composition II, were set up, with 10 animals in each group.

1.3.2 Dosage Design

The recommended daily intake dose per person of the composite powder of the test medicine, i.e. composition II, is 200 ml/60 kg BW. Every 1000 ml of composition II is formulated with 120 g total crude drugs, and thus the recommended daily intake dose per person is 24 g crude drugs/60 kg BW. Based on this dose, daily intake doses for mice are calculated as 2.0 g crude drugs/kg BW for the low-dose group, 4.0 g crude drugs/kg BW for the medium-dose group, and 12 g crude drugs/kg BW for the high-dose group, equivalent to 5, 10, and 30 times the daily intake dose for human, respectively. The samples were prepared in distilled water to make intragastric administration liquids having corresponding concentrations (i.e. 0.0164 g dry powder/ml, 0.0328 g dry powder/ml, 0.0984 g dry powder/ml) for experimentation. The intragastric administration amount for mice was calculated based on a ratio of 0.1 ml/10 g BW.

The recommended daily intake dose per person of composition I is 24 g crude drugs/60 kg BW. Based on this dose, the dose for mice is calculated as 4.0 g crude drugs/kg BW (equivalent to 10 times the daily intake dose for human). The sample was prepared in distilled water to make a 0.0318 g dry powder/ml intragastric administration liquid for experimentation. The intragastric administration amount was calculated based on a ratio of 0.1 ml/10 g BW. The blank control group and the model control group were each given an equal volume of distilled water by intragastric administration. The intragastric administrations were conducted once a day and continued for 30 days. All mice groups were fed with common feed and allowed free access to feed and water.

After 30 days, blood were sampled for determination of the activities of superoxide dismutase (SOD) and glutathione peroxidase (GSH-Px) and the content of malondialdehyde (MDA) in serum. Thereafter, except the blank control group, the other groups of mice were all irradiated once with 6Gy $^{60}$Co γ ray over the entire body. Four days after irradiation, the mice of all groups were sacrificed, and liver tissues were taken out for determination of the activities of superoxide dismutase (SOD) and glutathione peroxidase (GSH-Px) and the content of malondialdehyde (MDA).

1.3.3 Examined Indicators

The activities of SOD and GSH-Px and the MDA content in both serum and liver tissues were measured by strictly following the instructions for the kit provided by Nanjing Jiancheng Bioengineering Institute.

1.3.4 Statistic Methods

The experimental data are expressed as $\bar{x} \pm s$. One-way analysis of variance was employed to compare the activities of SOD and GSH-Px and the MDA content in serum before irradiation between the dosed test groups and the blank control group for difference, and to compare the activities of SOD and GSH-Px and the MDA content in liver tissues after irradiation between the dosed test groups on one hand and the model control group and the group on the original formulation on the other for difference. $P<0.05$ indicates the difference is significant.

2. Results 2.1 Body Weight Gain of Animals

The experimental results are shown in Table 1 below. Compared to the blank control group and the group on composition I, the mice groups that received various doses of composition II showed no significant difference in body weight. See Table 1 below.

TABLE 1

The effect of composition II on the body weight gain of the mice (g, $\bar{x} \pm s$)

| Group Name | Dose (g crude drugs/kg) | Number of Animals | Initial Body Weight | Final Body Weight |
| --- | --- | --- | --- | --- |
| Blank control group | 0.0 | 10 | 19.82 ± 1.12 | 33.30 ± 3.37 |
| Model control group | 0.0 | 10 | 19.67 ± 0.99 | 33.52 ± 3.46 |
| Group on composition I | 4.0 | 10 | 19.87 ± 1.30 | 33.68 ± 3.28 |
| Low-dose group on test medicine | 2.0 | 10 | 19.68 ± 1.12 | 33.20 ± 3.50 |
| Medium-dose group on test medicine | 4.0 | 10 | 19.58 ± 1.32 | 33.80 ± 3.20 |
| High-dose group on test medicine | 12.0 | 10 | 19.66 ± 1.22 | 32.90 ± 3.42 |

2.2 Effect of Composition II on the Serum Levels of GSH-Px, SOD, and MDA of the Mice The experimental results are shown in Table 2 below. Compared to the blank control group, the mice groups that received various doses of composition II and the mice group that received composition I showed significantly increased serum activities of GSH-Px and SOD and meanwhile a significantly decreased serum MDA content. Compared to the group that received composition I, the mice groups that received the low, medium, and high doses of the composite powder of composition II showed significantly increased serum activities of both GSH-Px and SOD and meanwhile a significantly decreased serum MDA content.

TABLE 2

The effect of composition II on the serum levels of GSH-Px, SOD, and MDA of the mice ($\bar{x} \pm s$)

| Group Name | Dose (g/kg) | Number of Animals | GSH-Px (EU) | SOD (U/mL) | MDA (nmol/mL) |
| --- | --- | --- | --- | --- | --- |
| Blank control group | 0.0 | 10 | 608.00 ± 117.68 | 112.00 ± 10.53 | 10.32 ± 1.40 |
| Model control group | 0.0 | 10 | 613.50 ± 100.46 | 109.50 ± 11.22 | 10.45 ± 1.04 |
| Group on composition I | 4.0 | 10 | 727.20 ± 113.18* | 123.40 ± 8.98** | 9.48 ± 1.00* |
| Low-dose group on test medicine | 2.0 | 10 | 731.50 ± 71.93* | 127.20 ± 11.09** | 9.25 ± 1.22* |
| Medium-dose group on test medicine | 4.0 | 10 | 856.90 ± 89.23**▲▲ | 135.80 ± 12.16**▲ | 8.45 ± 0.81**▲ |
| High-dose group on test medicine | 12.0 | 10 | 908.00 ± 118.81**▲▲ | 140.00 ± 11.89**▲▲ | 8.12 ± 0.66**▲▲ |

*$P < 0.05$ and

**$P < 0.01$ compared to the model control group;

▲$P < 0.05$ and

▲▲$P < 0.01$ compared to the group on composition I.

2.3 Effect of Composition II on the Liver Levels of GSH-Px, SOD, and MDA of the Irradiated Mice The experimental results are shown in Table 3 below. Compared to the blank control group, the mice of the model control group showed significantly decreased liver activities of GSH-Px and SOD and a significantly increased liver MDA content, indicating successful establishment of an irradiation model. Compared to the model control group, the mice groups that received the low, medium, and high doses of composition II and the mice group that received composition I all showed significantly increased liver activities of GSH-Px and SOD and meanwhile a significantly decreased liver MDA content. Compared to the group that received composition I, the mice groups that received the medium and high doses of composition II showed significantly increased liver activities of GSH-Px and SOD and meanwhile a significantly decreased liver MDA content.

content significantly lower than that of the comparative group that received composition I. The composite powder of composition II is believed to have a function of resisting oxidation more effectively than the original formulation.

Example 6

1. Materials and Methods 1.1 Sources of Samples

The test sample is TCM composition I (herein refers to Radix Panacis Quinquefolii, *Ganoderma*, and *Cordyceps*) provided by Jiangzhong Pharmaceutical Co. Ltd. as composite powder for oral liquid, and 1 g of this dry composite powder is equivalent to 11.41 g total crude drugs. The recommended daily intake dose per person thereof is 24 g crude drugs/60 kg BW.

TABLE 3

The effect of composition II on the liver levels of GSH-Px, SOD, and MDA of the irradiated mice ($\bar{x} \pm s$)

| Group Name | Dose (g/kgbw) | Number of Animals | GSH-Px (EU/mgprot) | SOD (U/mgprot) | MDA (nmol/mgprot) |
|---|---|---|---|---|---|
| Blank control group | 0.0 | 10 | 832.66 ± 139.40** | 146.20 ± 13.22** | 0.86 ± 0.14** |
| Model control group | 0.0 | 10 | 489.70 ± 109.20 | 108.70 ± 12.67 | 1.38 ± 0.12 |
| Group on composition I | 4.0 | 10 | 620.86 ± 110.55** | 126.40 ± 13.92** | 1.20 ± 0.10** |
| Low-dose group on test medicine | 2.0 | 10 | 610.30 ± 109.90** | 132.20 ± 16.82** | 1.17 ± 0.20** |
| Medium-dose group on test medicine | 4.0 | 10 | 738.66 ± 121.50**▲ | 145.20 ± 16.80**▲ | 0.97 ± 0.18**▲▲ |
| High-dose group on test medicine | 12.0 | 10 | 786.30 ± 120.22**▲▲ | 150.60 ± 18.30**▲▲ | 0.85 ± 0.14**▲▲ |

*$P < 0.05$ and
**$P < 0.01$ compared to the model control group;
▲$P < 0.05$ and
▲▲$P < 0.01$ compared to the group on composition I.

3. Conclusion

The daily intake dose of composition II recommended for human (i.e., 24.0 g crude drugs/60 kg BW) was scaled up by 5, 10, and 30 times to set up a low-dose group, a medium-dose group, and a high-dose group, respectively, corresponding to the doses of 2.0 g, 4.0 g, and 12.0 g crude drugs per kg BW. A blank control group, a model control group, and a group on composition I were further set up. CL healthy male Kunming mice were continuously administered intragastrically with the test samples, and after 30 days related indicators were measured. $P<0.05$ and $P<0.01$ indicate the experimental results show significant difference and highly significant difference, respectively. The animal experiments demonstrated that the mice groups that received the low, medium, and high doses of composition II are all able to increase their serum GSH-Px and SOD activities and decrease their serum MDA content; the mice groups that received the low, medium, and high doses of composition II all showed liver activities of GSH-Px and SOD significantly higher than those of the model control group which had been irradiated once with $6Gy^{60}Co\gamma$ ray over the entire body, and all showed a liver MDA content significantly lower than that of the model control group; and the mice groups that received the medium and high doses of composition II both showed liver activities of GSH-Px and SOD significantly higher than those of the comparative group that received composition I, and a liver MDA The comparative sample is TCM composition II (herein refers to Radix Panacis Quinquefolii, *Ganoderma*, and *Cordyceps sinensis* powder) provided by Jiangzhong Pharmaceutical Co. Ltd. as composite powder. 1 g of this dry composite powder is equivalent to 10.97 g total crude drugs. The recommended daily intake dose per person thereof is 24 g crude drugs/60 kg BW.

1.2 Laboratory Animals and Experimental Environments

CL healthy male Kunming mice, each weighing 18 to 22 g, were provided by the Laboratory Animal Center, Jiangxi University of Traditional Chinese Medicine (Certification Number: SCXK (Jiangxi)-2006-0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods 1.3.1 Animal Grouping 60 mice were divided randomly into 6 groups based on their body weights. A blank control group, a model control group, a group on TCM composition II, and test groups on a low dose, a medium dose, and a high dose of the oral liquid of TCM composition I, were set up, with 10 animals in each group.

1.3.2 Dosage Design

The recommended daily intake dose per person of the oral liquid of the test medicine, i.e. TCM composition I, is 200 ml/60 kg BW. Every 1000 ml of the oral liquid of TCM composition I is formulated with 120 g total crude drugs, and thus the recommended daily intake dose per person is 24 g crude drugs/60 kg BW. Based on this dose, daily intake doses for mice are calculated as 2.0 g crude drugs/kg BW for the low-dose group, 4.0 g crude drugs/kg BW for the medium-dose group, and 12 g crude drugs/kg BW for the high-dose group, equivalent to 5, 10, and 30 times the daily intake dose for human, respectively. The samples were prepared in distilled water to make intragastric administration liquids having corresponding concentrations (i.e. 0.0175 g dry powder/ml, 0.0350 g dry powder/ml, 0.1050 g dry powder/ml) for experimentation. The intragastric administration amount for mice was calculated based on a ratio of 0.1 ml/10 g BW.

The recommended daily intake dose per person of TCM composition II is 24 g crude drugs/60 kg BW. Based on this dose, the dose for mice is calculated as 4.0 g crude drugs/kg BW (equivalent to 10 times the daily intake dose for human). The sample was prepared in distilled water to make a 0.0365 g dry powder/ml intragastric administration liquid for experimentation. The intragastric administration amount was calculated based on a ratio of 0.1 ml/10 g BW. The blank control group and the model control group were each given an equal volume of distilled water by intragastric administration. The intragastric administrations were conducted once a day and continued for 30 days. All mice groups were fed with common feed and allowed free access to feed and water.

After 30 days, blood were sampled for determination of the activities of superoxide dismutase (SOD) and glutathione peroxidase (GSH-Px) and the content of malondialdehyde (MDA) in serum. Thereafter, except the blank control group, the other groups of mice were all irradiated once with 6Gy$^{60}$Co γ ray over the entire body. Four days after irradiation, the mice of all groups were sacrificed, and liver tissues were taken out for determination of the activities of superoxide dismutase (SOD) and glutathione peroxidase (GSH-Px) and the content of malondialdehyde (MDA).

1.3.3 Examined Indicators

The activities of SOD and GSH-Px and the MDA content in both serum and liver tissues were measured by strictly following the instructions for the kit provided by Nanjing Jiancheng Bioengineering Institute.

1.3.4 Statistic Methods

The experimental data are expressed as $\bar{x} \pm s$. One-way analysis of variance was employed to compare the activities of SOD and GSH-Px and the MDA content in serum before irradiation between the dosed test groups and the blank control group for difference, and to compare the activities of SOD and GSH-Px and the MDA content in liver tissues after irradiation between the dosed test groups on one hand and the model control group and the group on the original formulation on the other for difference. $P<0.05$ indicates the difference is significant.

2. Results

2.1 Body Weight Gain of Animals

The experimental results are shown in Table 1 below. Compared to the blank control group and the group on TCM composition II, the mice groups that received various doses of the oral liquid of TCM composition I showed no significant difference in body weight. See Table 1 below.

TABLE 1

The effect of the oral liquid of TCM composition I on the body weight gain of the mice (g, $\bar{x} \pm s$)

| Group Name | Dose (g crude drugs/kg) | Number of Animals | Initial Body Weight | Final Body Weight |
|---|---|---|---|---|
| Blank control group | 0.0 | 10 | 19.36 ± 1.08 | 33.90 ± 2.67 |
| Model control group | 0.0 | 10 | 19.20 ± 0.96 | 33.80 ± 2.38 |
| Group on TCM composition II | 4.0 | 10 | 19.56 ± 1.02 | 34.00 ± 2.92 |
| Low-dose group on test medicine | 2.0 | 10 | 19.40 ± 1.09 | 33.50 ± 2.46 |
| Medium-dose group on test medicine | 4.0 | 10 | 19.52 ± 1.03 | 33.90 ± 2.80 |
| High-dose group on test medicine | 12.0 | 10 | 19.60 ± 1.12 | 34.60 ± 2.20 |

2.2 Effect of the Oral Liquid of TCM Composition I on the Serum Levels of GSH-Px, SOD, and MDA of the Mice The experimental results are shown in Table 2 below. Compared to the blank control group, the mice groups that received various doses of the oral liquid of TCM composition I and the mice group that received TCM composition II all showed significantly increased serum activities of GSH-Px and SOD and meanwhile a significantly decreased serum MDA content. Compared to the group that received TCM composition II, the mice groups that received the medium and high doses of the composite powder for oral liquid of TCM composition I showed significantly increased serum activities of both GSH-Px and SOD and meanwhile a significantly decreased serum MDA content.

TABLE 2

The effect of the oral liquid of TCM composition I on the serum levels of GSH-Px, SOD, and MDA of the mice ($\bar{x} \pm s$)

| Group Name | Dose (g/kg) | Number of Animals | GSH-Px (EU) | SOD (U/mL) | MDA (nmol/mL) |
|---|---|---|---|---|---|
| Blank control group | 0.0 | 10 | 620.70 ± 137.33 | 110.80 ± 11.96 | 10.47 ± 1.44 |
| Model control group | 0.0 | 10 | 620.90 ± 105.73 | 108.10 ± 13.59 | 10.60 ± 1.20 |
| Group on TCM composition II | 4.0 | 10 | 754.60 ± 134.60* | 124.90 ± 10.89** | 9.38 ± 1.14* |
| Low-dose group on test medicine | 2.0 | 10 | 764.30 ± 91.47** | 129.20 ± 13.08** | 9.19 ± 1.22** |
| Medium-dose group on test medicine | 4.0 | 10 | 877.10 ± 95.92**▲ | 138.20 ± 14.03**▲ | 8.41 ± 0.86**▲ |

TABLE 2-continued

The effect of the oral liquid of TCM composition I on the serum levels of GSH-Px, SOD, and MDA of the mice ($\bar{x} \pm s$)

| Group Name | Dose (g/kg) | Number of Animals | GSH-Px (EU) | SOD (U/mL) | MDA (nmol/mL) |
|---|---|---|---|---|---|
| High-dose group on test medicine | 12.0 | 10 | 953.30 ± 122.89**▲▲ | 142.20 ± 12.60**▲▲ | 8.13 ± 0.65**▲▲ |

*P < 0.05 and
**P < 0.01 compared to the model control group;
▲P < 0.05 and
▲▲P < 0.01 compared to the group on TCM composition II.

2.3 Effect of the Oral Liquid of TCM Composition I on the Liver Levels of GSH-Px, SOD, and MDA of the Irradiated Mice The experimental results are shown in Table 3 below. Compared to the blank control group, the mice of the model control group showed significantly decreased liver activities of GSH-Px and SOD and a significantly increased liver MDA content, indicating successful establishment of an irradiation model. Compared to the model control group, the mice groups that received the low, medium, and high doses of the oral liquid of TCM composition I and the mice group that received TCM composition II all showed significantly increased liver activities of GSH-Px and SOD and meanwhile a significantly decreased liver MDA content. Compared to the group that received TCM composition II, the mice groups that received the medium and high doses of the oral liquid of TCM composition I showed significantly increased liver activities of GSH-Px and SOD and meanwhile a significantly decreased liver MDA content.

ously administered intragastrically with the test samples, and after 30 days related indicators were measured. P<0.05 and P<0.01 indicate the experimental results show significant difference and highly significant difference, respectively. The animal experiments demonstrated that the mice groups that received the low, medium, and high doses of the oral liquid of TCM composition I are all able to increase their serum GSH-Px and SOD activities and decrease their serum MDA content; the mice groups that received the low, medium, and high doses of the oral liquid of TCM composition I all showed liver activities of GSH-Px and SOD significantly higher than those of the model control group which had been irradiated once with 6Gy$^{60}$Co γ ray over the entire body, and all showed a liver MDA content significantly lower than that of the model control group; and the mice groups that received the medium and high doses of the oral liquid of TCM composition I both showed liver activities of GSH-Px and SOD significantly higher than those of the comparative group that received TCM composition II, and a liver MDA content significantly

TABLE 3

The effect of the oral liquid of TCM composition I on the liver levels of GSH-Px, SOD, and MDA of the irradiated mice ($\bar{x} \pm s$)

| Group Name | Dose (g/kgbw) | Number of Animals | GSH-Px (EU/mgprot) | SOD (U/mgprot) | MDA (nmol/mgprot) |
|---|---|---|---|---|---|
| Blank control group | 0.0 | 10 | 865.30 ± 103.38** | 147.00 ± 15.41** | 0.84 ± 0.13** |
| Model control group | 0.0 | 10 | 462.90 ± 101.26 | 102.90 ± 14.39 | 1.39 ± 0.13 |
| Group on TCM composition II | 4.0 | 10 | 616.80 ± 113.14** | 125.90 ± 15.69** | 1.18 ± 0.14** |
| Low-dose group on test medicine | 2.0 | 10 | 620.30 ± 99.58** | 131.00 ± 15.97** | 1.15 ± 0.21** |
| Medium-dose group on test medicine | 4.0 | 10 | 733.90 ± 120.88**▲ | 143.10 ± 15.50**▲ | 0.96 ± 0.15**▲▲ |
| High-dose group on test medicine | 12.0 | 10 | 780.20 ± 89.54**▲▲ | 149.80 ± 16.75**▲▲ | 0.87 ± 0.16**▲▲ |

*P < 0.05 and
**P < 0.01 compared to the model control group;
▲P < 0.05 and
▲▲P < 0.01 compared to the group on TCM composition II.

3. Conclusion

The daily intake dose of the oral liquid of TCM composition I recommended for human (i.e., 24.0 g crude drugs/60 kg BW) was scaled up by 5, 10, and 30 times to set up a low-dose group, a medium-dose group, and a high-dose group, respectively, corresponding to the doses of 2.0 g, 4.0 g, and 12.0 g crude drugs per kg BW. A blank control group, a model control group, and a group on TCM composition II were further set up. CL healthy male Kunming mice were continulower than that of the comparative group that received TCM composition II. The composite powder for oral liquid of TCM composition I is believed to have a function of resisting oxidation more effectively than the original formulation.

Example 7

1. Materials and Methods
1.1 Sources of Samples

The test sample is TCM composition I (herein refers to Radix Panacis Quinquefolii, *Ganoderma*, and *Cordyceps*) provided by Jiangzhong Pharmaceutical Co. Ltd. as composite powder for oral liquid, and 1 g of this dry composite powder is equivalent to 11.41 g total crude drugs. The recommended daily intake dose per person thereof is 24 g crude drugs/60 kg BW.

The comparative sample is TCM composition II (herein refers to Radix Panacis Quinquefolii, *Ganoderma*, and fermented *Cordyceps sinensis* powder) provided by Jiangzhong Pharmaceutical Co. Ltd. as composite powder. 1 g of this dry composite powder is equivalent to 10.97 g total crude drugs. The recommended daily intake dose per person thereof is 24 g crude drugs/60 kg BW.

1.2 Laboratory Animals

CL healthy male Kunming mice, each weighing 18 to 22 g, were provided by the Laboratory Animal Center, Jiangxi University of Traditional Chinese Medicine (Certification Number: SCXK (Jiangxi)-2006-0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods 1.3.1 Animal Grouping

The mice (150 animals in total) underwent experiments in three batches, and the mice in each batch were divided randomly into 5 groups (10 animals in each group). Experimental batch 1 was subjected to the anoxia endurance experiment under normal pressure, Experimental batch 2 to the sodium nitrite poisoning survival experiment, and Experimental batch 3 to the acute cerebral ischemic anoxia experiment.

1.3.2 Dosage Design

The recommended daily intake dose per person of the oral liquid of the test medicine, i.e. TCM composition I, is 200 ml/60 kg BW. Every 1000 ml oral liquid of TCM composition I is formulated with 120 g total crude drugs, and thus the recommended daily intake dose per person is 24 g crude drugs/60 kg BW. Based on this dose, daily intake doses for mice are calculated as 2.0 g crude drugs/kg BW for the low-dose group, 4.0 g crude drugs/kg BW for the medium-dose group, and 12 g crude drugs/kg BW for the high-dose group, equivalent to 5, 10, and 30 times the daily intake dose for human, respectively. The samples were prepared in distilled water to make intragastric administration liquids having corresponding concentrations (i.e. 0.0175 g dry powder/ml, 0.0350 g dry powder/ml, 0.1050 g dry powder/ml) for experimentation. The intragastric administration amount for mice was calculated based on a ratio of 0.1 ml/10 g BW.

The recommended daily intake dose per person of TCM composition II is 24 g crude drugs/60 kg BW. Based on this dose, the dose for mice is calculated as 4.0 g crude drugs/kg BW (equivalent to 10 times the daily intake dose for human). The sample was prepared in distilled water to make a 0.0365 g dry powder/ml intragastric administration liquid for experimentation. The intragastric administration amount was calculated based on a ratio of 0.1 ml/10 g BW. The administrations were conducted once a day. The body weights were measured weekly, according to which the intragastric administration amounts were adjusted. After continuous intragastric administrations for 45 days, various indicators were measured. A blank control group was also set up, and was intragastrically administered with distilled water in a daily volume equal to that for the test groups. During the experiments the animals were allowed free access to food and water.

1.3.3 Anoxia Endurance Experiment Under Normal Pressure

One hour after the last intragastric administration of the 45-day intragastric administrations, all groups of mice were placed into the 250 ml flasks having a ground glass joint and containing 5 g soda lime (one animal in each flask), and counting of time was started immediately after the opening of each flask was sealed with Vaseline and a stopper to be air tight. The time when the mice died of anoxia, as indicated by respiratory arrest, was recorded.

1.3.4 Sodium Nitrite Poisoning Survival Experiment

One hour after the last intragastric administration, all groups of mice were intraperitoneally injected with sodium nitrite at a dose of 240 mg/kg BW (the injection amount was 0.1 ml/10 g). Time was counted immediately after the injection and survival time of mice was recorded.

1.3.5 Acute Cerebral Ischemic Anoxia Experiment

One hour after the last intragastric administration, each of the mice in all groups was decapitated from the cervical part under light anesthesia with diethyl ether, and time was counted immediately thereafter to record the duration from the decapitation to the cessation of breath through the mouth of the mouse.

1.4 Main Apparatus and Reagents 250 ml flasks with a ground glass joint; a stopwatch; 1 ml syringes; scissors; Vaseline, soda lime, sodium nitrite.

1.5 Statistic Methods

All results are expressed as Average value±Standard deviation. One-way analysis of variance was performed using the program SPSS 15.0 to compare the test groups and the control group for difference.

1.6 Standards for Evaluating Results The *Technical Standards for Testing and Assessment of Health Food* (2003) provides that if any two experiments of the anoxia endurance experiment under normal pressure, the sodium nitrite poisoning survival experiment, and the acute cerebral ischemic anoxia experiment show positive results, the tested samples are deemed as having an effect of enhancing anoxia endurance.

2. Results 2.1 Effect of the Oral Liquid of TCM Composition I on the Anoxia Endurance Time Under Normal Pressure of the Mice The experimental results are shown in Table 1 below. The mice groups that received the low, medium, and high doses of the oral liquid of TCM composition I and the mice group that received TCM composition II all showed an anoxia endurance time under normal pressure significantly longer than that of the blank control group. The mice groups that received the medium and high doses of the oral liquid of TCM composition I both showed an anoxia endurance time under normal pressure significantly longer than that of the comparative group that received TCM composition II.

TABLE 1

The effect of the oral liquid of TCM composition I on the anoxia endurance time under normal pressure of the mice ($\overline{X} \pm S$)

| Group Name | Dose (g crude drugs/kg) | Number of Animals | Anoxia Endurance Time Under Normal Pressure(s) |
|---|---|---|---|
| Blank control group | 0.0 | 10 | 2298.50 ± 204.81 |
| Group on TCM composition II | 4.0 | 10 | 2542.90 ± 212.41* |
| Low-dose group on test medicine | 2.0 | 10 | 2525.70 ± 239.64* |

TABLE 1-continued

The effect of the oral liquid of TCM composition
I on the anoxia endurance time under normal pressure
of the mice ($\overline{X} \pm S$)

| Group Name | Dose (g crude drugs/kg) | Number of Animals | Anoxia Endurance Time Under Normal Pressure(s) |
|---|---|---|---|
| Medium-dose group on test medicine | 4.0 | 10 | 2781.10 ± 199.17**▲ |
| High-dose group on test medicine | 12.0 | 10 | 2933.80 ± 174.81**▲▲ |

*P < 0.05 and
**P < 0.01 compared to the blank control group;
▲P < 0.05 and
▲▲P < 0.01 compared to the group on TCM composition II.

2.2 Effect of the Oral Liquid of TCM Composition I on the Survival Time of Mice after Sodium Nitrite Poisoning The experimental results are shown in Table 2 below. The mice groups that received the medium and high doses of the oral liquid of TCM composition I and the comparative mice group that received TCM composition II all showed a survival time after sodium nitrite poisoning significantly longer than that of the blank control group. The mice groups that received the medium and high doses of the oral liquid of TCM composition I both showed a survival time after sodium nitrite poisoning significantly longer than that of the comparative group that received TCM composition II.

TABLE 2

The effect of the oral liquid of TCM composition I on the survival time
of the mice after sodium nitrite poisoning ($\overline{X} \pm S$)

| Group Name | Dose (g crude drugs/kg) | Number of Animals | Survival Time after Sodium Nitrite Poisoning(s) |
|---|---|---|---|
| Blank control group | 0.0 | 10 | 940.20 ± 121.77 |
| Group on TCM composition II | 4.0 | 10 | 1071.70 ± 133.97* |
| Low-dose group on test medicine | 2.0 | 10 | 997.40 ± 111.48 |
| Medium-dose group on test medicine | 4.0 | 10 | 1192.40 ± 146.34**▲ |
| High-dose group on test medicine | 12.0 | 10 | 1195.70 ± 146.57**▲ |

*P < 0.05 and
**P < 0.01 compared to the blank control group;
▲P < 0.05 and
▲▲P < 0.01 compared to the group on TCM composition II.

2.3 Effect of the Oral Liquid of TCM Composition I on the Survival Time of Mice Under Acute Cerebral Ischemic Anoxia The experimental results are shown in Table 3 below. The mice groups that received the medium and high doses of the oral liquid of TCM composition I and the mice group that received TCM composition II all showed a survival time under cerebral ischemic anoxia significantly longer than that of the blank control group. The mice groups that received the medium and high doses of the oral liquid of TCM composition I both showed a survival time under cerebral ischemic anoxia significantly longer than that of the comparative group that received TCM composition II.

TABLE 3

The effect of the oral liquid of TCM composition I on the survival time
of the mice under cerebral ischemic anoxia ($\overline{X} \pm S$)

| Group Name | Dose (g crude drugs/kg) | Number of Animals | Survival Time of Mice under Cerebral Ischemic Anoxia(s) |
|---|---|---|---|
| Blank control group | 0.0 | 10 | 18.90 ± 1.47 |
| Group on TCM composition II | 4.0 | 10 | 20.73 ± 2.11* |
| Low-dose group on test medicine | 2.0 | 10 | 20.23 ± 1.88 |
| Medium-dose group on test medicine | 4.0 | 10 | 22.60 ± 2.05**▲ |
| High-dose group on test medicine | 12.0 | 10 | 22.98 ± 2.04**▲ |

*P < 0.05 and
**P < 0.01 compared to the blank control group;
▲P < 0.05 and
▲▲P < 0.01 compared to the group on TCM composition II.

3. Summary

The daily intake dose of the composite powder for oral liquid of TCM composition I recommended for human (i.e., 24 g crude drugs/60 kg BW) was scaled up by 5, 10, and 30 times to set up a low-dose group, a medium-dose group, and a high-dose group, respectively, corresponding to the doses of 2.0 g, 4.0 g, and 12.0 g crude drugs per kg BW. A blank control group and a comparative group on TCM composition II were further set up. CL healthy male mice were continuously administered intragastrically with the test samples, and after 45 days related indicators were measured. P<0.05 indicates the experimental results show significant difference. The animal experiments demonstrated that the mice groups that received the low, medium, and high doses of the oral liquid of TCM composition I showed an anoxia endurance time under normal pressure significantly longer than that of the blank control group; the mice groups that received the medium and high doses of the oral liquid of TCM composition I showed a survival time after sodium nitrite poisoning and a survival time under cerebral ischemic anoxia both significantly longer than those of the blank control group; and the mice groups that received the medium and high doses of the oral liquid of TCM composition I showed an anoxia endurance time under normal pressure, a survival time after sodium nitrite poisoning, and a survival time under cerebral ischemic anoxia all significantly longer than those of the comparative group that received TCM composition II. The oral liquid of TCM composition I is believed to have a health function of enhancing anoxia endurance more effectively than TCM composition II.

Example 8

1. Materials and Methods
1.1 Sources of Samples

The test sample is composition II (herein refers to Radix Panacis Quinquefolii, *Ganoderma*, *Cordyceps*, and Flos Rosae Rugosae) provided by Jiangzhong Pharmaceutical Co. Ltd. as composite powder, and 1 g of this dry composite powder is equivalent to 12.19 g total crude drugs. The recommended daily intake dose per person thereof is 24 g crude drugs/60 kg BW.

The comparative sample is composition I (herein refers to Radix Panacis Quinquefolii, *Ganoderma*, *Cordyceps sinensis* powder, and Flos Rosae Rugosae) provided by Jiangzhong Pharmaceutical Co. Ltd. as composite powder. 1 g of this dry composite powder is equivalent to 12.56 g total crude drugs. The recommended daily intake dose per person thereof is 24 g crude drugs/60 kg BW.

1.2 Laboratory Animals

CL healthy male Kunming mice, each weighing 18 to 22 g, were provided by the Laboratory Animal Center, Jiangxi University of Traditional Chinese Medicine (Certification Number: SCXK (Jiangxi)-2006-0001). They were fed in the animal room of Jiangxi University of Traditional Chinese Medicine (Certificate for Environments: SYXK (Jiangxi) 2004-0001) with a feeding environmental temperature of 21 to 23° C. and relative humidity of 50% to 60%.

1.3 Experimental Methods 1.3.1 Animal Grouping

The mice (150 animals in total) underwent experiments in three batches, and the mice in each batch were divided randomly into 5 groups (10 animals in each group). Experimental batch 1 was subjected to the anoxia endurance experiment under normal pressure, Experimental batch 2 to the sodium nitrite poisoning survival experiment, and Experimental batch 3 to the acute cerebral ischemic anoxia experiment.

1.3.2 Dosage Design

The recommended daily intake dose per person of the composite powder of the test medicine, i.e. composition II, is 200 ml/60 kg BW. Every 1000 ml of composition II is formulated with 120 g total crude drugs, and thus the recommended daily intake dose per person is 24 g crude drugs/60 kg BW. Based on this dose, daily intake doses for mice are calculated as 2.0 g crude drugs/kg BW for the low-dose group, 4.0 g crude drugs/kg BW for the medium-dose group, and 12 g crude drugs/kg BW for the high-dose group, equivalent to 5, 10, and 30 times the daily intake dose for human, respectively. The samples were prepared in distilled water to make intragastric administration liquids having corresponding concentrations (i.e. 0.0164 g dry powder/ml, 0.0328 g dry powder/ml, 0.0984 g dry powder/ml) for experimentation. The intragastric administration amount for mice was calculated based on a ratio of 0.1 ml/10 g BW.

The recommended daily intake dose per person of composition I is 24 g crude drugs/60 kg BW. Based on this dose, the dose for mice is calculated as 4.0 g crude drugs/kg BW (equivalent to 10 times the daily intake dose for human). The sample was prepared in distilled water to make a 0.0318 g dry powder/ml intragastric administration liquid for experimentation. The intragastric administration amount was calculated based on a ratio of 0.1 ml/10 g BW. The administrations were conducted once a day. The body weights were measured weekly, according to which the intragastric administration amounts were adjusted. After continuous intragastric administrations for 45 days, various indicators were measured. A blank control group was also set up, and was intragastrically administered with distilled water in a daily volume equal to that for the test groups. During the experiments the animals were allowed free access to food and water.

1.3.3 Anoxia Endurance Experiment Under Normal Pressure

One hour after the last intragastric administration of the 45-day intragastric administrations, all groups of mice were placed into the 250 ml flasks having a ground glass joint and containing 5 g soda lime (one animal in each flask), and counting of time was started immediately after the opening of each flask was sealed with Vaseline and a stopper to be air tight. The time when the mice died of anoxia, as indicated by respiratory arrest, was recorded.

1.3.4 Sodium Nitrite Poisoning Survival Experiment

One hour after the last intragastric administration, all groups of mice were intraperitoneally injected with sodium nitrite at a dose of 240 mg/kg BW (the injection amount was 0.1 ml/10 g). Time was counted immediately after the injection and survival time of mice was recorded.

1.3.5 Acute Cerebral Ischemic Anoxia Experiment

One hour after the last intragastric administration, each of the mice in all groups was decapitated from the cervical part under light anesthesia with diethyl ether, and time was counted immediately thereafter to record the duration from the decapitation to the cessation of breath through the mouth of the mouse.

1.4 Main Apparatus and Reagents 250 ml flasks with a ground glass joint; a stopwatch; 1 ml syringes; scissors; vaseline, soda lime, sodium nitrite.

1.5 Statistic Methods

All results are expressed as Average value±Standard deviation. One-way analysis of variance was performed using the program SPSS 15.0 to compare the test groups and the control group for difference.

1.6 Standards for Evaluating Results

The *Technical Standards for Testing and Assessment of Health Food* (2003) provides that if any two experiments of the anoxia endurance experiment under normal pressure, the sodium nitrite poisoning survival experiment, and the acute cerebral ischemic anoxia experiment show positive results, the tested samples are deemed as having an effect of enhancing anoxia endurance.

2. Results 2.1 Effect of the Composition II on the Anoxia Endurance Time Under Normal Pressure Of the Mice The experimental results are shown in Table 1 below. The mice groups that received the low, medium, and high doses of composition II and the mice group that received composition I all showed an anoxia endurance time under normal pressure significantly longer than that of the blank control group. The mice groups that received the medium and high doses of composition II both showed an anoxia endurance time under normal pressure significantly longer than that of the comparative group that received composition I.

TABLE 1

The effect of composition II on the anoxia endurance time under normal pressure of the mice ($\bar{X} \pm S$)

| Group Name | Dose (g crude drugs/kg) | Number of Animals | Anoxia Endurance Time Under Normal Pressure(s) |
|---|---|---|---|
| Blank control group | 0.0 | 10 | 2285.00 ± 213.10 |
| Group on composition I | 4.0 | 10 | 2530.90 ± 197.12* |
| Low-dose group on test medicine | 2.0 | 10 | 2513.60 ± 255.44* |
| Medium-dose group on test medicine | 4.0 | 10 | 2784.20 ± 198.78**▲ |
| High-dose group on test medicine | 12.0 | 10 | 2938.40 ± 176.55**▲▲ |

*$P < 0.05$ and
**$P < 0.01$ compared to the blank control group;
▲$P < 0.05$ and
▲▲$P < 0.01$ compared to the group on composition I.

2.2 Effect of Composition II on the Survival Time of Mice after Sodium Nitrite Poisoning The experimental results are shown in Table 2 below. The mice groups that received the medium and high doses of composition II and the comparative mice group that received composition I all showed a survival time after sodium nitrite poisoning significantly longer than that of the blank control group. The mice groups that received the medium and high doses of composition II both showed a survival time after sodium nitrite poisoning significantly longer than that of the comparative group that received composition I.

TABLE 2

The effect of composition II on the survival time of the mice after sodium nitrite poisoning ($\overline{X} \pm S$)

| Group Name | Dose (g crude drugs/kg) | Number of Animals | Survival Time after Sodium Nitrite Poisoning(s) |
|---|---|---|---|
| Blank control group | 0.0 | 10 | 950.90 ± 128.62 |
| Group on composition I | 4.0 | 10 | 1075.20 ± 134.10* |
| Low-dose group on test medicine | 2.0 | 10 | 1001.40 ± 111.42 |
| Medium-dose group on test medicine | 4.0 | 10 | 1198.30 ± 138.94**▲ |
| High-dose group on test medicine | 12.0 | 10 | 1210.90 ± 142.45**▲ |

*P < 0.05 and
**P < 0.01 compared to the blank control group;
▲P < 0.05 and
▲▲P < 0.01 compared to the group on composition I.

2.3 Effect of Composition II on the Survival Time of Mice Under Acute Cerebral Ischemic Anoxia The experimental results are shown in Table 3 below. The mice groups that received the medium and high doses of composition II and the mice group that received composition I all showed a survival time under cerebral ischemic anoxia significantly longer than that of the blank control group. The mice groups that received the medium and high doses of composition II both showed a survival time under cerebral ischemic anoxia significantly longer than that of the comparative group that received composition I.

TABLE 3

The effect of composition II on the survival time of the mice under cerebral ischemic anoxia ($\overline{X} \pm S$)

| Group Name | Dose (g crude drugs/kg) | Number of Animals | Survival Time of Mice under Cerebral Ischemic Anoxia(s) |
|---|---|---|---|
| Blank control group | 0.0 | 10 | 18.75 ± 1.45 |
| Group on composition I | 4.0 | 10 | 20.82 ± 2.24* |
| Low-dose group on test medicine | 2.0 | 10 | 20.28 ± 1.89 |
| Medium-dose group on test medicine | 4.0 | 10 | 22.74 ± 2.04**▲ |
| High-dose group on test medicine | 12.0 | 10 | 23.50 ± 2.11**▲ |

*P < 0.05 and
**P < 0.01 compared to the blank control group;
▲P < 0.05 and
▲▲P < 0.01 compared to the group on composition I.

3. Summary

The daily intake dose of the composite powder of composition II recommended for human (i.e., 24 g crude drugs/60 kg BW) was scaled up by 5, 10, and 30 times to set up a low-dose group, a medium-dose group, and a high-dose group, respectively, corresponding to the doses of 2.0 g, 4.0 g, and 12.0 g crude drugs per kg BW. A blank control group and a comparative group on composition I were further set up. CL healthy male mice were continuously administered intragastrically with the test samples, and after 45 days related indicators were measured. P<0.05 indicates the experimental results show significant difference. The animal experiments demonstrated that the mice groups that received the low, medium, and high doses of composition II showed an anoxia endurance time under normal pressure significantly longer than that of the blank control group; the mice groups that received the medium and high doses of composition II showed a survival time after sodium nitrite poisoning and a survival time under cerebral ischemic anoxia both significantly longer than those of the blank control group; and the mice groups that received the medium and high doses of composition II showed an anoxia endurance time under normal pressure, a survival time after sodium nitrite poisoning, and a survival time under cerebral ischemic anoxia all significantly longer than those of the comparative group that received composition I. Composition II is believed to have a health function of enhancing anoxia endurance more effectively than composition I.

Example 9

350 g Radix Panacis Quinquefolii, 400 g *Ganoderma*, and 200 g fermented *Cordyceps sinensis* powder were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 10

150 g Radix Panacis Quinquefolii, 400 g *Ganoderma*, and 150 g fermented *Cordyceps sinensis* powder were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 11

350 g Radix Panacis Quinquefolii, 250 g *Ganoderma*, and 300 g fermented *Cordyceps sinensis* powder were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 12

250 g Radix Panacis Quinquefolii, 300 g *Ganoderma*, and 100 g fermented *Cordyceps sinensis* powder were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 13

450 g Radix Panacis Quinquefolii, 100 g *Ganoderma*, and 100 g fermented *Cordyceps sinensis* powder were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 14

100 g Radix Panacis Quinquefolii, 100 g *Ganoderma*, and 500 g fermented *Cordyceps sinensis* powder were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 15

300 g Radix Panacis Quinquefolii, 400 g *Ganoderma*, 250 g fermented *Cordyceps sinensis* powder, and 350 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 16

200 g Radix Panacis Quinquefolii, 450 g *Ganoderma*, 150 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 17

400 g Radix Panacis Quinquefolii, 250 g *Ganoderma*, 250 g fermented *Cordyceps sinensis* powder, and 120 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 18

100 g Radix Panacis Quinquefolii, 100 g *Ganoderma*, 100 g fermented *Cordyceps sinensis* powder, and 100 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 19

100 g Radix Panacis Quinquefolii, 200 g *Ganoderma*, 300 g fermented *Cordyceps sinensis* powder, and 100 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 20

100 g Radix Panacis Quinquefolii, 300 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 21

100 g Radix Panacis Quinquefolii, 300 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 22

200 g Radix Panacis Quinquefolii, 300 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 23

200 g Radix Panacis Quinquefolii, 400 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 24

200 g Radix Panacis Quinquefolii, 500 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 25

300 g Radix Panacis Quinquefolii, 400 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 26

100 g Radix Panacis Quinquefolii, 300 g *Ganoderma*, 500 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 27

400 g Radix Panacis Quinquefolii, 300 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 28

400 g Radix Panacis Quinquefolii, 400 g *Ganoderma*, 200 g fermented *Cordyceps sinensis* powder, and 100 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 29

300 g Radix Panacis Quinquefolii, 100 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 30

300 g Radix Panacis Quinquefolii, 300 g *Ganoderma*, 300 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 31

500 g Radix Panacis Quinquefolii, 300 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 32

300 g Radix Panacis Quinquefolii, 300 g *Ganoderma*, 200 g fermented *Cordyceps sinensis* powder, and 400 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 33

500 g Radix Panacis Quinquefolii, 100 g *Ganoderma*, 200 g fermented *Cordyceps sinensis* powder, and 500 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 34

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A clear paste was made by further concentration under reduced pressure, which was then turned into powder by spray drying to prepare a composite powder.

Example 35

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for tablets were added thereto and uniformly mixed; and various types of tablets were prepared by conventional processes for tablets.

Example 36

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for granules were added thereto and uniformly mixed; and granules were prepared by conventional processes for granules.

Example 37

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for pills were added thereto and uniformly mixed; and various types of pills were prepared by conventional processes for pills.

Example 38

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for syrups were added thereto and uniformly mixed, and syrups were prepared by conventional processes for syrups.

Example 39

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for capsules were added thereto and uniformly mixed; and capsules were prepared by conventional processes for capsules.

Example 40

350 g Radix Panacis Quinquefolii, 400 g *Ganoderma*, and 200 g fermented *Cordyceps sinensis* powder (*Paecilongces*

*hepialli* Chen et Dai, sp. nov) were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 41

150 g Radix Panacis Quinquefolii, 400 g *Ganoderma*, and 150 g fermented *Cordyceps sinensis* powder (*Hirsutella sinensis* Liu, Guo, Yu et Zeng, sp. nov) were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 42

350 g Radix Panacis Quinquefolii, 250 g *Ganoderma*, and 300 g fermented *Cordyceps sinensis* powder (*Cephalosporium sinensis* Chen sp. nov) were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 43

250 g Radix Panacis Quinquefolii, 300 g *Ganoderma*, and 100 g fermented *Cordyceps sinensis* powder (*Mortiserella hepialid* C. T.&B. liu) were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 44

450 g Radix Panacis Quinquefolii, 100 g *Ganoderma*, and 100 g fermented *Cordyceps sinensis* powder (*Paecilomyces sinensis* Chen, Xiao et Shi, sp. nov) were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 45

100 g Radix Panacis Quinquefolii, 100 g *Ganoderma*, and 500 g fermented *Cordyceps sinensis* powder (*Tolypocladium sinensis* C. lan Li) were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 46

300 g Radix Panacis Quinquefolii, 400 g *Ganoderma*, 250 g fermented *Cordyceps sinensis* powder (*Hirsutella hepialid* Chen et Shen), and 350 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 47

200 g Radix Panacis Quinquefolii, 450 g *Ganoderma*, 150 g fermented *Cordyceps sinensis* powder (*Mortierella* sp.), and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 48

400 g Radix Panacis Quinquefolii, 250 g *Ganoderma*, 250 g fermented *Cordyceps sinensis* powder (*Gliocladium roseum* (link) Thom), and 120 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 49

100 g Radix Panacis Quinquefolii, 100 g *Ganoderma*, 100 g fermented *Cordyceps sinensis* powder (*Mortierella* sp.), and 100 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 50

100 g Radix Panacis Quinquefolii, 200 g *Ganoderma*, 300 g fermented *Cordyceps sinensis* powder (*Synnematium sinensis* Yin & Shen), and 100 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 51

100 g Radix Panacis Quinquefolii, 300 g *Ganoderma*, 200 g fermented *Cordyceps sinensis* powder (*Cephalosporium sinensis* Chen sp. nov), and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 52

100 g Radix Panacis Quinquefolii, 300 g *Ganoderma*, 200 g fermented *Cordyceps sinensis* powder (*Hirsutella hepialid* Chen et Shen), and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 53

200 g Radix Panacis Quinquefolii, 300 g *Ganoderma*, 200 g fermented *Cordyceps sinensis* powder (*Mortierella* sp.), and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 54

200 g Radix Panacis Quinquefolii, 400 g *Ganoderma*, 200 g fermented *Cordyceps sinensis* powder (CS-C-Q80), and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 55

200 g Radix Panacis Quinquefolii, 500 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 56

300 g Radix Panacis Quinquefolii, 400 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 57

100 g Radix Panacis Quinquefolii, 300 g *Ganoderma*, 500 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 58

400 g Radix Panacis Quinquefolii, 300 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 59

400 g Radix Panacis Quinquefolii, 400 g *Ganoderma*, 200 g fermented *Cordyceps sinensis* powder, and 100 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 60

300 g Radix Panacis Quinquefolii, 100 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 61

300 g Radix Panacis Quinquefolii, 300 g *Ganoderma*, 300 g fermented *Cordyceps sinensis* powder, and 200 g Flos Rosae Rugosae were weighed out. The Radix Panacis Quinquefolii and *Ganoderma* were sliced and the fermented

*Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 62

500 g Radix Panacis Quinquefolii, 300 g *Ganoderma*, 200 g fermented *Cordyceps sinensis* powder, and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 63

500 g Radix Panacis Quinquefolii, 500 g *Ganoderma*, 500 g fermented *Cordyceps sinensis* powder, and 500 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 64

500 g Radix Panacis Quinquefolii, 100 g *Ganoderma*, 200 g fermented *Cordyceps sinensis* powder, and 500 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 65

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A clear paste was made by further concentration under reduced pressure, which was then turned into powder by spray drying to prepare a composite powder.

Example 66

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for tablets were added thereto and uniformly mixed; and various types of tablets were prepared by conventional processes for tablets.

Example 67

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for granules were added thereto and uniformly mixed; and granules were prepared by conventional processes for granules.

Example 68

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for pills were added thereto and uniformly mixed; and various types of pills were prepared by conventional processes for pills.

Example 69

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for syrups were added thereto and uniformly mixed, and syrups were prepared by conventional processes for syrups.

Example 70

300 g Radix Panacis Quinquefolii, 400 g *Ganoderma*, 200 g fermented *Cordyceps sinensis* powder, and 300 g Flos Rosae Rugosae and/or 5-150 g Semen Cuscutae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for capsules were added thereto and uniformly mixed; and capsules were prepared by conventional processes for capsules.

Example 71

300 g Radix Panacis Quinquefolii, 400 g *Ganoderma*, and 200 g fermented *Cordyceps sinensis* powder (*Paecilongces hepialli* Chen et Dai, sp. nov) were weighed out. The Radix Panacis Quinquefolii and *Ganoderma* were sliced and the fermented *Cordyceps sinensis* powder was put in a cloth bag. The above three drugs were soaked in water for 0.5 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 72

150 g Radix Et Rhizoma Ginseng, 400 g *Ganoderma*, and 150 g fermented *Cordyceps sinensis* powder (*Hirsutella sinensis* Liu, Guo, Yu et Zeng, sp. nov) were weighed out. The Radix Panacis Quinquefolii and *Ganoderma* were sliced and the fermented *Cordyceps sinensis* powder was put in a cloth bag. The above four drugs were soaked in water for 0.5 h, and decocted by heating for 3 times. The first decoction lasted for 2 h for extraction with a 10-fold amount of water, and the following decoctions each lasted for 1 h with an 8-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 73

300 g Radix Panacis Quinquefolii, 400 g *Ganoderma*, and 6.7 g *Cordyceps* and/or 300 g fermented *Cordyceps sinensis* powder (*Cephalosporium sinensis* Chen sp. nov) were weighed out. The Radix Panacis Quinquefolii and *Ganoderma* were sliced and the fermented *Cordyceps sinensis* powder was put in a cloth bag. The above four drugs were soaked in water for 0.5 h, and decocted by heating for 3 times. The first decoction lasted for 2 h for exaction with a 15-fold amount of water, and the following decoctions each lasted for 1 h with an 8-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 74

300 g Radix Panacis Quinquefolii, 400 g *Ganoderma*, 200 g fermented *Cordyceps sinensis* powder (*Mortiserella hepialid* C. T.&B. liu), and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1.2 h, with a 5-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 75

100 g Radix Panacis Quinquefolii, 100 g *Ganoderma*, 3 g fermented *Cordyceps sinensis* powder (*Paecilomyces sinen-*

*sis* Chen, Xiao et Shi, sp. nov), and 10 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 4-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 76

100 g Radix Panacis Quinquefolii and/or Radix Et Rhizoma Ginseng, 250 g *Ganoderma*, 250 g fermented *Cordyceps sinensis* powder (*Tolypocladium sinensis* C. lan Li), and 120 g Flos Rosae Rugosae were weighed out. The Radix Panacis Quinquefolii and *Ganoderma* were sliced and the fermented *Cordyceps sinensis* powder was put in a cloth bag. The above four or five drugs were soaked in water for 0.5 h, and decocted by heating for 3 times. The first decoction lasted for 2 h for extraction with a 15-fold amount of water, and the following decoctions each lasted for 1 h with a 9-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 77

10 g Radix Panacis Quinquefolii, 20 g *Ganoderma*, 3 g fermented *Cordyceps sinensis* powder (*Hirsutella sinensis* Liu, Guo, Yu et Zeng, sp. nov), 3 g *Cordyceps*, and 10 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1.5 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 78

3-200 g Radix Astragali and/or 160 g Radix Codonopsis, 300 g *Ganoderma*, 200 g fermented *Cordyceps sinensis* powder (*Hirsutella hepialid* Chen et Shen), and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 5-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 79

200 g Radix Panacis Quinquefolii, 300 g *Ganoderma*, 200 g fermented *Cordyceps sinensis* powder (*Mortierella* sp.), and 200 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 0.5 h, and decocted by heating for 3 times. The first decoction lasted for 2 h for extraction with a 15-fold amount of water, and the following decoctions each lasted for 1 h with an 8-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 80

3-400 g Radix Astragali, 350 g *Ganoderma*, 100 g fermented *Cordyceps sinensis* powder, and 100 g Flos Rosae Rugosae were weighed out. The Radix Astragali and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1.4 h, with a 7-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 81

30 g Radix Astragali, 40 g *Ganoderma*, 20 g fermented *Cordyceps sinensis* powder, and 30 g Flos Rosae Rugosae were weighed out. The Radix Astragali and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A clear paste was made by further concentration under reduced pressure, which was then turned into powder by spray drying to prepare a composite powder.

Example 82

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for tablets were added thereto and uniformly mixed; and various types of tablets were prepared by conventional processes for tablets.

Example 83

300 g Radix Panacis Quinquefolii, 400 g *Ganoderma*, 200 g fermented *Cordyceps sinensis* powder, and 300 g Flos Rosae Rugosae were weighed out. The Radix Panacis Quinquefolii and *Ganoderma* were sliced and the fermented *Cordyceps sinensis* powder was put in a cloth bag. The above four drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for capsules were added thereto and uniformly mixed; and capsules were prepared by conventional processes for capsules.

Example 84

1-120 g Folium Ginseng, 300 g *Ganoderma*, and 80 g *Cordyceps* were weighed out. The Folium Ginseng and *Ganoderma* were sliced and the *Cordyceps* was pulverized put in a cloth bag. All of the drugs were soaked in water for 1 h, and decocted by heating for 3 times. The first decoction lasted for 2 h and the following decoctions each lasted for 1.5 h, with a 15-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 85

300 g Radix Et Rhizoma Ginseng Rubra, 400 g *Ganoderma*, 67 g *Cordyceps*, and 200 g fermented *Cordyceps sinensis* powder (*Paecilongces hepialli* Chen et Dai, sp. nov) were weighed out. The Radix Panacis Quinquefolii and *Ganoderma* were sliced, and the pulverized *Cordyceps* and the *Cordyceps sinensis* powder were put in separate cloth bags. All the drugs were soaked in water for 0.5 h, and decocted by heating for 2 times. The first decoction lasted for 2 h for exaction with a 15-fold amount of water, and the second decoction lasted for 1 h with a 13-fold amount of water added. The two liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 86

450 g Radix Panacis Quinquefolii, 200 g *Ganoderma*, 90 g *Cordyceps*, and 600 g fermented *Cordyceps sinensis* powder (*Hirsutella sinensis* Liu, Guo, Yu et Zeng, sp. nov) were weighed out. The Radix Panacis Quinquefolii and *Ganoderma* were sliced, and the pulverized *Cordyceps* and the *Cordyceps sinensis* powder were put in separate cloth bags. All the drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 87

100 g Radix Et Rhizoma Ginseng, 800 g *Ganoderma*, 30 g *Cordyceps*, and 300 g fermented *Cordyceps sinensis* powder (*Gliocladium roseum* (link) Thom) were weighed out. The Radix Et Rhizoma Ginseng and *Ganoderma* were sliced, and the pulverized *Cordyceps* and the *Cordyceps sinensis* powder were put in separate cloth bags. All the drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 88

250 g Radix Panacis Quinquefolii, 300 g *Ganoderma*, 80 g *Cordyceps*, and 900 g fermented *Cordyceps sinensis* powder (*Mortierella* sp.) were weighed out. The Radix Panacis Quinquefolii and *Ganoderma* were sliced, and the pulverized *Cordyceps* and the *Cordyceps sinensis* powder were put in separate cloth bags. All the drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 89

300 g Radix Et Rhizoma Ginseng and/or 300 g Radix Codonopsis, 400 g *Ganoderma*, 20 g *Cordyceps*, and 33 g fermented *Cordyceps sinensis* powder (*Cephalosporium sinensis* Chen sp. nov) were weighed out. The Radix Et Rhizoma Ginseng and *Ganoderma* were sliced, and the pulverized *Cordyceps* and the *Cordyceps sinensis* powder were put in separate cloth bags. All the drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 90

100 g Radix Panacis Quinquefolii, 200 g *Ganoderma*, 30 g *Cordyceps*, 30 g fermented *Cordyceps sinensis* powder (*Mortierella* sp.), and 100 g Flos Rosae Rugosae were weighed out. The Radix Panacis Quinquefolii and *Ganoderma* were sliced, and the pulverized *Cordyceps* and the *Cordyceps sinensis* powder were put in separate cloth bags. All the drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 91

900 g Radix Et Rhizoma Ginseng, 900 g *Ganoderma*, 900 g *Cordyceps*, 900 g fermented *Cordyceps sinensis* powder (*Hirsutsua sinensis* Liu, Guo, Yu et Zeng, sp. nov), and 600 g Flos Rosae Rugosae were weighed out. The Radix Et Rhizoma Ginseng and *Ganoderma* were sliced, and the pulverized *Cordyceps* and the *Cordyceps sinensis* powder were put in separate cloth bags. All the drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 92

1,500 g Radix Panacis Quinquefolii and/or 2,000 g Radix Astragali, 1,600 g *Ganoderma*, 1,200 g *Cordyceps*, 900 g fermented *Cordyceps sinensis* powder (*Paecilongces hepialli* Chen et Dai, sp. nov), and 900 g Flos Rosae Rugosae were weighed out. The Radix Panacis Quinquefolii and/or Radix Astragali and the *Ganoderma* were sliced, and the pulverized *Cordyceps* and the *Cordyceps sinensis* powder were put in separate cloth bags. All the drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

Example 93

50 g Radix Panacis Quinquefolii, 50 g *Ganoderma*, 10 g *Cordyceps* and/or 10 g fermented *Cordyceps sinensis* powder (*Paecilongces hepialli* Chen et Dai, sp. nov), and 50 g Flos Rosae Rugosae were weighed out. The Radix Panacis Quinquefolii and *Ganoderma* were sliced, and the pulverized *Cordyceps* was put in a cloth bag. All the drugs were soaked in water for 0.5 h, and decocted by heating for 2 times. The first decoction lasted for 2 h for exaction with a 15-fold amount of water, and the second decoction lasted for 1 h with a 13-fold amount of water added. The two liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for pills were added thereto and uniformly mixed; and various types of pills were prepared by conventional processes for pills.

Example 94

300 g Radix Panacis Quinquefolii, 400 g *Ganoderma*, 67 g *Cordyceps*, 200 g fermented *Cordyceps sinensis* powder (*Hirsutella hepialid* Chen et Shen), and 300 g Flos Rosae Rugosae were weighed out. The Radix Panacis Quinquefolii and *Ganoderma* were sliced, and the pulverized *Cordyceps* and the *Cordyceps sinensis* powder were put in a cloth bag together. The above drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A clear paste was made by further concentration under reduced pressure, which was then turned into powder by spray drying to prepare a composite powder.

Example 95

300 g Radix Panacis Quinquefolii, 300 g *Ganoderma*, 67 g *Cordyceps* and/or 200 g fermented *Cordyceps sinensis* powder (*Paecilongces hepialli* Chen et Dai, sp. nov), and 300 g Flos Rosae Rugosae were weighed out. The Radix Panacis Quinquefolii and *Ganoderma* were sliced, and the pulverized *Cordyceps* and/or the *Cordyceps sinensis* powder were put in a cloth bag together. All the drugs were soaked in water for 1 h, and decocted by heating for 3 times. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for granules were added thereto and uniformly mixed; and granules were prepared by conventional processes for granules.

Example 96

300 g Radix Panacis Quinquefolii, 400 g *Ganoderma*, 67 g *Cordyceps*, 200 g fermented *Cordyceps sinensis* powder (*Synnematium sinensis* Yin & Shen), and 300 g Flos Rosae Rugosae were weighed out. The Radix Panacis Quinquefolii and *Ganoderma* were sliced, and the pulverized *Cordyceps* and/or the *Cordyceps sinensis* powder were put in a cloth bag together. The drugs were extracted under reflux once or twice upon addition of ethanol or methanol, with each extraction lasting for 1-2 h. Then the liquid extracts were combined, and ethanol or methanol was recovered to obtain the alcohol extract. The residual drugs were further decocted in water by heating for 1-3 times, with each decoction lasting for 1-2 h. The alcohol extract and the water extract were combined and filtered, the liquid filtrate was concentrated to an appropriate level, the liquid concentrate was left to cool down, and the impurities therein were then removed by ultracentrifuge to provide a ready-for-use state. The above drugs were soaked in water for 1 h, and decocted by heating for 3 times, in which the first decoction lasted for 2 h and the following decoctions each lasted for 1 h, with a 10-fold amount of water added for each decoction. The alcohol extract and the water extract were combined and filtered, the liquid filtrate was concentrated to an appropriate level, the liquid concentrate was left to cool down, and the impurities therein were then removed by ultracentrifuge. A paste was made by further concentration under reduced pressure, or powder was made by spray drying; auxiliary agents frequently used for capsules were added thereto and uniformly mixed; and capsules were prepared by conventional processes for capsules.

Example 97

300 g Radix Panacis Quinquefolii, 400 g *Ganoderma*, and 67 g *Cordyceps* were weighed out. The Radix Panacis Quinquefolii and *Ganoderma* were sliced, and the pulverized *Cordyceps* was put in a cloth bag. The drugs were extracted under reflux once or twice upon addition of ethanol, with each extraction lasting for 1-2 h. Then the liquid extracts were combined, and ethanol was recovered to obtain the alcohol extract. The residual drugs were further decocted in water by heating for 1-3 times, with each decoction lasting for 1-2 h. The alcohol extract and the water extract were combined and filtered, the liquid filtrate was concentrated to an appropriate level, the liquid concentrate was left to cool down, and the impurities therein were then removed by ultracentrifuge to provide a ready-for-use state. The above drugs were soaked in water for 1.5 h, and decocted by heating once, in which the first decoction lasted for 2 h and the following decoctions each lasted for 1 h, with a 10-fold amount of water added for each decoction. The alcohol extract and the water extract were combined and filtered, the liquid filtrate was concentrated to an appropriate level, the liquid concentrate was left to cool down, the impurities therein were then removed by ultracentrifuge, auxiliary agents frequently used for oral liquid were added thereto and uniformly mixed, and a 20,000 ml oral liquid was prepared by conventional processes for oral liquid.

The invention claimed is:

1. A method of resisting oxidation or enhancing anoxia endurance comprising the step of administering a composition to a subject, wherein the composition comprises raw materials of 10-50 parts by weight of Radix Panacis Quinquefolii, 10-50 parts by weight of *Ganoderma*, 10-40 parts by weight of Flos Rosae Rugosae, and 10-50 parts by weight of fermented *Cordyceps sinensis* powder, or water extracts of said raw materials, as active ingredients.

2. The method of claim 1, characterized in that the raw materials are 30 parts of Radix Panacis Quinquefolii, 40 parts of *Ganoderma*, and 20 parts of fermented *Cordyceps sinensis* powder.

3. The method of claim 2, characterized in that said raw materials further include 30 parts by weight of Flos Rosae Rugosae, or a water extract of 30 parts by weight of Flos Rosae Rugosae.

4. The method of claim 1, characterized in that the species to which the fermented *Cordyceps sinensis* powder belong is selected from the group consisting of *Paecilongces hepialli* Chen et Dai, sp. nov, Mortiscrslla hepialid C. T.&B. liu, *Synnematium sinensis* Yin & Shen, *Gliocladium roseum* (link) Thom, *Mortierella* sp., *Cephalosporium sinensis* Chen sp. nov, and *Hirsutella sinensis* Liu, Guo, Yu et Zeng, sp. nov.

5. The method of claim 1, characterized in that said raw materials further include a material selected from the group consisting of 3-300 parts by weight of Radix Pseudostellariae, 1-120 parts by weight of Folium Ginseng, 3-160 parts by weight of Radix Codonopsis, 3-200 parts by weight of Radix Astragali, and 5-150 parts by weight of Semen Cuscutae, and any combination thereof.

6. A method of relieving physical fatigue comprising the step of administering a composition to a subject, wherein the composition comprises raw materials of 10-50 parts by weight of Radix Panacis Quinquefolii, 10-50 parts by weight of *Ganoderma*, 10-40 parts by weight of Flos Rosae Rugosae, and 10-50 parts by weight of fermented *Cordyceps sinensis* powder, or water extracts of said raw materials, as active ingredients.

7. A method of relieving physical fatigue, reducing blood lipids, resisting oxidation, or enhancing anoxia endurance comprising the step of administering a composition to a subject, wherein the composition is formulated with the following raw materials:

Radix Et Rhizoma Ginseng and/or Radix Panacis Quinquefolii of no less than 5 parts by weight and less than 10 parts by weight, or of more than 50 parts by weight and no more than 150 parts by weight;

*Ganoderma* of no less than 5 parts by weight and less than 10 parts by weight, or of more than 50 parts by weight and no more than 160 parts by weight;

Flos Rosae Rugosae of no less than 5 parts by weight and less than 10 parts by weight, or of more than 40 parts by weight and no more than 90 parts by weight; and fermented *Cordyceps sinensis* powder of no less than 1 parts by weight and less than 10 parts by weight, or of more than 50 parts by weight and no more than 90 parts by weight.

* * * * *